(12) United States Patent
Carayon et al.

(10) Patent No.: US 7,777,041 B2
(45) Date of Patent: Aug. 17, 2010

(54) 2-ACYLAMINO-4-PHENYLTHIAZOLE DERIVATIVES, PREPARATION THEREOF AND THERAPEUTIC APPLICATION THEREOF

(75) Inventors: Pierre Carayon, Montpellier (FR); Pierre Casellas, Montpellier (FR); Daniel Floutard, Combaillaux (FR); Pierre Fraisse, Juvignac (FR); Samir Jegham, Montferrier-sur-Lez (FR); Bernard Labeeuw, Montpellier (FR)

(73) Assignee: sanofi-aventis, Paris (FR)

( * ) Notice: Subject to any disclaimer, the term of this patent is extended or adjusted under 35 U.S.C. 154(b) by 0 days.

(21) Appl. No.: 12/360,568

(22) Filed: Jan. 27, 2009

(65) Prior Publication Data

US 2009/0156574 A1 Jun. 18, 2009

Related U.S. Application Data

(60) Division of application No. 11/253,998, filed on Oct. 19, 2005, now Pat. No. 7,504,511, which is a continuation of application No. PCT/FR2004/000981, filed on Apr. 22, 2004.

(30) Foreign Application Priority Data

Apr. 25, 2003 (FR) .................................. 03 05213

(51) Int. Cl.
C07D 405/00 (2006.01)
(52) U.S. Cl. .................................................... 546/207
(58) Field of Classification Search .................. 546/207
See application file for complete search history.

(56) References Cited

U.S. PATENT DOCUMENTS

| | | | |
|---|---|---|---|
| 4,225,610 | A | 9/1980 | Tarayre et al. |
| 5,314,889 | A | 5/1994 | Boigegrain et al. |
| 5,656,642 | A | 8/1997 | Fujioka et al. |
| 2002/0119980 | A1 | 8/2002 | Ko et al. |
| 2004/0048891 | A1 | 3/2004 | Kato et al. |
| 2007/0179126 | A1 | 8/2007 | Casellas et al. |
| 2007/0259847 | A1 | 11/2007 | Casellas et al. |
| 2009/0018117 | A1 | 1/2009 | Casellas et al. |

FOREIGN PATENT DOCUMENTS

| | | | |
|---|---|---|---|
| CA | 2129374 | | 2/1995 |
| DE | 55 034 | | 4/1967 |
| DE | 2706269 | A * | 8/1978 |
| EP | 0 001 727 | | 5/1979 |
| EP | 0519449 | | 12/1992 |
| EP | 0 638 553 | | 2/1995 |
| EP | 0518731 | | 8/1998 |
| EP | 1 344 525 | A1 | 9/2003 |
| FR | 2 296 497 | | 12/1974 |
| JP | 2004-256429 | | 9/2004 |
| WO | WO 93/00342 | | 1/1993 |
| WO | WO 02/18335 | | 3/2002 |
| WO | WO 02/051397 | | 7/2002 |
| WO | WO 02/066460 | | 8/2002 |
| WO | WO 02/081449 | | 10/2002 |
| WO | WO 03/015778 | | 2/2003 |
| WO | WO 03/088908 | A2 | 10/2003 |
| WO | WO 2006/016039 | A1 | 2/2006 |
| WO | WO 2006/042954 | A1 | 4/2006 |
| WO | WO 2007/077394 | | 7/2007 |

OTHER PUBLICATIONS

Allen et al, Discovery And SAR Of Trisubstituted Thiazolidinones As CCR4 Antagonists, Bioorganic & Medicinal Chemistry Letters, Apr. 2004, 14:1619-1624.
Baker et al., Candidate Active-Site-Directed Irreversible Inhibitors of Dihydrofolic Reductase VI. Derivatives of Hydrophobically Bonded p-Alkyl and p-Aralkyl Benzoic Acids, J. Pharm. Sci., (1967), vol. 56, pp. 38-42.
Blicke et al., Basic-Alkyl Esters of p-(Aminoalkyl)-Benzoic Acids, J. Amer. Chem. Soc., (1943), vol. 65, No. 12, pp. 2281-2284.
Byrn et al, Hydrates and Solvates, Solid-State Chemistry of Drugs, Second Edition, 1999, pp. 233-247.
Lombardino et al., Potent Antiinflammatory N-Heterocyclic 3-Carboxamides of 4-Hydroxy-2-methyl-2H-1,2-benzothiazine 1,1-Dioxide, J. Med. Chem., 16 (5) pp. 493-496 (1973).
Pearson et al., Preparation of Functionalized RHO-Phenylenediamine Derivatives Using Arene-Iron Chemistry, J. Org. Chem., (1996), vol. 61, pp. 1297-1305.
Sagi et al., Rational Design, Synthesis, and Structure-Activity Relationship of Novel Factor Xa Inhibitors: (2-Substituted-4-amidinophenyl)pyruvic and propionic Acids, J. Med. Chem, (2003), vol. 46, pp. 1845-1857.
Sall et al., Diamino Benzo[b]thiophene Derivatives as a Novel Class of Active Site Directed Thrombin Inhibitors. 5. Potency, Efficacy, and Pharmacokinetic Properties of Modified C-3 Side Chain Derivatives, J. Med. Chem., (2000), vol. 43, No. 4, pp. 649-663.

* cited by examiner

Primary Examiner—Janet L Andres
Assistant Examiner—John Mabry
(74) Attorney, Agent, or Firm—Kelly L. Bender; Paul R. Darkes

(57) ABSTRACT

The invention relates to 2-acylamino-4-phenylthiazole derivatives of general formula (I):

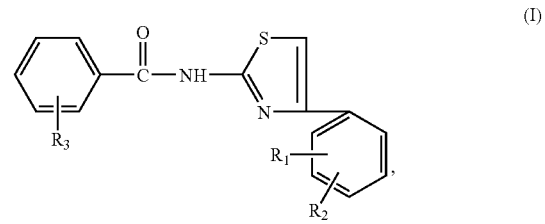

pharmaceutically acceptable acid-addition salts thereof, hydrates or solvates of such derivatives or such pharmaceutically acceptable acid addition salts, intermediates thereto, processes for the preparation thereof, and therapeutic application thereof.

2 Claims, No Drawings

2-ACYLAMINO-4-PHENYLTHIAZOLE DERIVATIVES, PREPARATION THEREOF AND THERAPEUTIC APPLICATION THEREOF

The present invention relates to 2-acylamino-4-phenylthiazole derivatives, to their preparation and to their therapeutic application.

The present invention relates to compounds corresponding to formula (I):

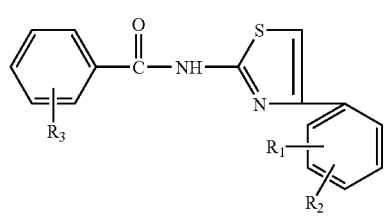

(I)

in which:
  $R_1$ represents a hydrogen or halogen atom or a $(C_1-C_4)$ alkyl, trifluoroethyl, hydroxyl, $(C_1-C_4)$ alkoxy, trifluoromethoxy, trifluoroethoxy, $(C_3-C_8)$cycloalkyloxy, allyloxy, cyclopropylmethoxy or $(C_1-C_4)$alkylthio group;
  $R_2$ represents a hydrogen or halogen atom or a $(C_1-C_8)$ alkyl, trifluoroethyl, perfluoro$(C_1-C_4)$alkyl, $(C_3-C_{10})$cycloalkyl, phenyl, $(C_1-C_8)$alkoxy, trifluoromethoxy, trifluoroethoxy, allyloxy, $(C_3-C_8)$cycloalkylmethoxy, $(C_3-C_8)$cycloalkyloxy or $(C_3-C_8)$ cycloalkylmethyl group;
  $R_3$ represents a group chosen from:
   a) a1) —O—$(C_2-C_4)$alk-A;
   a2) —O—$(C_1-C_4)$alk-B;
   a3) —O-E;
   b) —$(C_1-C_4)$alk-A;
   c) —B;
   d) d1) —$(C_1-C_4)$alk-NR$_4$—$(C_2-C_3)$alk-A;
   d2) —$(C_1-C_4)$alk-NR$_4$—$(C_1-C_3)$alk-B;
   e) e1) —CONR$_4$—$(C_2-C_4)$alk-A;
   e2) —CONR$_4$—$(C_1-C_4)$alk-B;
   e3) —CONR$_4$-E;
   f) f1) —CO-D-$(C_1-C_2)$alk-A;
   f2) —CO-G-A;

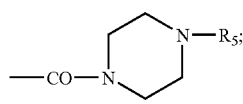
(f3)

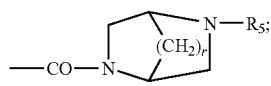
(f4)

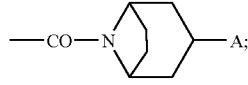
(f5)

(f6)

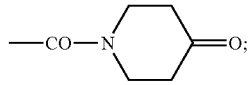
(f7)

$R_4$ represents a hydrogen atom or a $(C_1-C_4)$alkyl group;
A represents a group $NR_5R_6$;
B represents a group

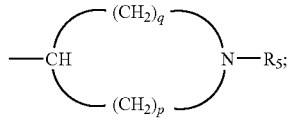

D represents a group

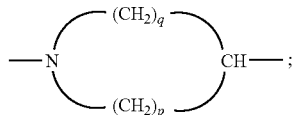

E represents a group

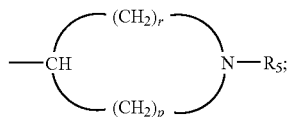

G represents a group

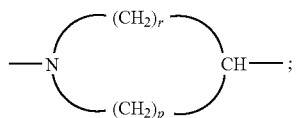

$R_5$ and $R_6$ each represent, independently of each other, a hydrogen atom or a $(C_1-C_6)$alkyl, allyl, $(C_2-C_4)$alk-O—$(C_1-C_4)$alkyl, $(C_2-C_4)$alk-OH, $(C_1-C_3)$alk-CON$(R_4)_2$, $(C_2-C_3)$ alk-NHCO—$(C_1-C_4)$alkyl, $(C_3-C_7)$cycloalkyl, $(C_3-C_7)$cycloalkylmethyl, —CO—$(C_1-C_4)$alkyl, pyrrolidinyl optionally substituted with a —CO—$(C_1-C_4)$ alkyl group, benzyl, tetrahydropyranyl, tetrahydropyranylmethyl, dimethyltetrahydropyranyl, tetrahydrofuryl or tetrahydrofurylmethyl group;
or $R_5$ and $R_6$, together with the nitrogen atom to which they are attached, constitute a heterocyclic radical chosen from: aziridinyl, azetidinyl, pyrrolidinyl, piperidinyl, perhydroazepinyl, morpholinyl, piperazinyl, tropanyl, quinuclidinyl, 2-azabicyclo[2,2,1]heptanyl, 2-azabicyclo[2,2,2]octanyl, the said heterocyclic radicals being unsubstituted or substituted with a phenyl, halophenyl, trifluoromethylphenyl, trifluoromethyl, hydroxyl, methoxy, hydroxymethyl, methoxymethyl, formamido or trifluoroacetylamino group, a group —NR$_4$R$_7$, tetrahydropyran-4-ylamino, —CON$(R_4)_2$, —CONR$_4$R'$_4$, —CH$_2$CON$(R_4)_2$, $(C_1-C_4)$alkyl-CONR$_4$—, $(C_3-C_8)$cycloalkyl-CONR$_4$—, $(C_1-C_4)$ alkyl-OCONR$_4$—, $(C_3$-

$C_8$) cycloalkyl-OCONR$_4$—, ((C$_1$-C$_4$)alkyl-OCO)$_2$N— or (C$_1$-C$_4$)alkyl-COO—; or substituted with one or more methyl groups;

R'$_4$ represents a group (CH$_2$)$_s$ linked to the carbon atom bearing —CONR$_4$R'$_4$;

R$_7$ represents a hydrogen atom, a (C$_1$-C$_4$)alkyl or an —SO$_2$CH$_3$ group or R$_4$ and R$_7$, together with the nitrogen atom to which they are attached, constitute a pyrrolidinyl or piperidinyl radical;

p represents 1, 2, 3, 4 or 5;

q represents 0, 1 or 2;

r represents 1 or 2;

s represents 2 or 3;

p+q being less than or equal to 5;

p+r being less than or equal to 5;

alk represents an alkylene;

with the condition that R$_1$ and R$_2$ are not simultaneously a hydrogen atom.

The compounds of formula (I) may comprise one or more asymmetric carbon atoms. They may thus exist in the form of enantiomers or diastereoisomers. These enantiomers and diastereoisomers, and also the mixtures thereof, including racemic mixtures, form part of the invention. Similarly, the axial and equatorial, endo and exo stereoisomers and also mixtures thereof form part of the invention.

The compounds of formula (I) may exist in the form of bases or of acid-addition salts. Such addition salts form part of the invention.

These salts are advantageously prepared with pharmaceutically acceptable acids, but the salts of other acids that are useful, for example, for purifying or isolating the compounds of formula (I) also form part of the invention.

The compounds of formula (I) may also exist in the form of hydrates or solvates, i.e. in the form of associations or combinations with one or more molecules of water or with a solvent. Such hydrates and solvates also form part of the invention.

In the context of the present invention, the following terms have the meanings given below:

a halogen atom: a fluorine, a chlorine, a bromine or an iodine;

an alkyl group: a linear or branched monovalent saturated aliphatic group containing 1 to 4 carbon atoms or, where appropriate, 1 to 8 carbon atoms. Examples that may be mentioned include methyl, ethyl, propyl, isopropyl, butyl, isobutyl, tert-butyl, pentyl, neopentyl, tert-pentyl, etc. groups;

a cycloalkyl group: a cyclic alkyl group containing 3 to 8 carbon atoms or, where appropriate, 3 to 10 carbon atoms, which is optionally bridged. Examples that may be mentioned include cyclopropyl, cyclobutyl, cyclopentyl, cyclohexyl, cycloheptyl, cyclooctyl and adamantyl groups;

an alkoxy group: a radical —O-alkyl in which the alkyl group is as defined above;

an alkylene group: a linear or branched divalent saturated aliphatic group containing 1 to 3 carbon atoms or, where appropriate, 2 to 3 or 2 to 4 carbon atoms.

Among the compounds of formula (I) that are subjects of the invention, mention may be made of a first sub-group of compounds corresponding to the general formula (I'):

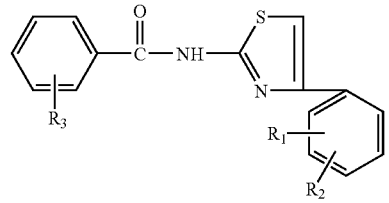

in which:

R$_1$ represents a hydrogen or halogen atom or a (C$_1$-C$_4$) alkyl, trifluoroethyl, hydroxyl, (C$_1$-C$_4$) alkoxy, trifluoromethoxy, trifluoroethoxy, (C$_3$-C$_8$)cycloalkyloxy, allyloxy, cyclopropylmethoxy or (C$_1$-C$_4$)alkylthio group;

R$_2$ represents a hydrogen or halogen atom or a (C$_1$-C$_8$) alkyl, trifluoroethyl, perfluoro(C$_1$-C$_4$)alkyl, (C$_3$-C$_{10}$)cycloalkyl, phenyl, (C$_1$-C$_8$)alkoxy, trifluoromethoxy, trifluoroethoxy, allyloxy, (C$_3$-C$_8$)cycloalkylmethoxy, (C$_3$-C$_8$)cycloalkyloxy or (C$_3$-C$_8$) cycloalkylmethyl group;

R$_3$ represents a group chosen from:
a) a1) —O— (C$_2$-C$_4$) alk-A;
a2) —O— (C$_1$-C$_4$) alk-B;
a3) —O-E;
b) —(C$_1$-C$_4$)alk-A;
c) —B;
d) d1) —(C$_1$-C$_4$)alk-NR$_4$—(C$_2$-C$_3$)alk-A;
d2) —(C$_1$-C$_4$)alk-NR$_4$—(C$_1$-C$_3$)alk-B;
e) e1) —CONR$_4$—(C$_2$-C$_4$)alk-A;
e2) —CONR$_4$—(C$_1$-C$_4$)alk-B;
e3) —CONR$_4$-E;
f) f1) —CO-D-(C$_1$-C$_2$)alk-A;
f2) —CO-G-A;

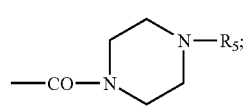

f3)

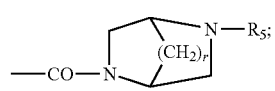

f4)

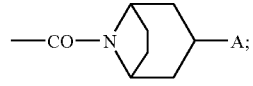

f5)

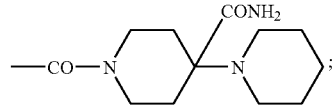

f6)

R$_4$ represents a hydrogen atom or a (C$_1$-C$_4$)alkyl group;
A represents a group NR$_5$R$_6$;
B represents a group

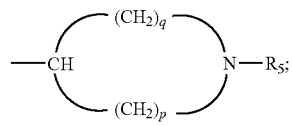

D represents a group

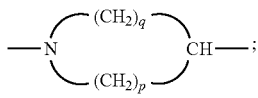

E represents a group

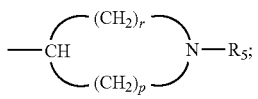

G represents a group

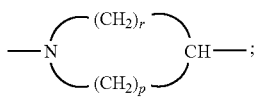

R₅ and R₆ each represent, independently of each other, a hydrogen atom or a $(C_1-C_6)$alkyl, allyl, $(C_2-C_4)$alk-O—$(C_1-C_4)$alkyl, $(C_2-C_4)$alk-OH, $(C_1-C_3)$alk-CON$(R_4)_2$, $(C_2-C_3)$alk-NHCO—$(C_1-C_4)$alkyl, $(C_3-C_7)$cycloalkyl, $(C_3-C_7)$cycloalkylmethyl, benzyl, tetrahydropyranyl, tetrahydropyranylmethyl, dimethyltetrahydropyranyl, tetrahydrofuryl or tetrahydrofurylmethyl group;

or R₅ and R₆, together with the nitrogen atom to which they are attached, constitute a heterocyclic radical chosen from: aziridinyl, azetidinyl, pyrrolidinyl, piperidinyl, perhydroazepinyl, morpholinyl, piperazinyl, tropanyl, quinuclidinyl, 2-azabicyclo[2,2,1]heptanyl, 2-azabicyclo[2,2,2]octanyl, the said heterocyclic radicals being unsubstituted or substituted with a phenyl, halophenyl, trifluoromethylphenyl, trifluoromethyl, hydroxyl, methoxy, hydroxymethyl, methoxymethyl, formamido or trifluoroacetylamino group, a group —NR₄R₇, tetrahydropyran-4-ylamino, —CON$(R_4)_2$, —CONR₄R'₄, —CH₂CON$(R_4)_2$, $(C_1-C_4)$alkyl-CONR₄—, $(C_1-C_4)$alkyl-OCONR₄— or $(C_1-C_4)$alkyl-COO—; or substituted with one or more methyl groups;

R'₄ represents a group (CH₂), linked to the carbon atom bearing —CONR₄R'₄;

R₇ represents a hydrogen atom or a $(C_1-C_4)$alkyl, or R₄ and R₇, together with the nitrogen atom to which they are attached, constitute a pyrrolidinyl or piperidinyl radical;

p represents 1, 2, 3, 4 or 5;
q represents 0, 1 or 2;
r represents 1 or 2;
s represents 2 or 3;
p+q being less than or equal to 5;
p+r being less than or equal to 5;
alk represents an alkylene;

with the condition that R₁ and R₂ are not simultaneously a hydrogen atom.

Among the compounds of formula (I) that are subjects of the invention, mention may be made of a second sub-group of compounds, which are defined as follows:

R₁ is in position –2 of the phenyl and/or R₂ is in position –5 and/or R₃ is in position –4 of the other phenyl; thus more particularly, mention may be made of the compounds of formula:

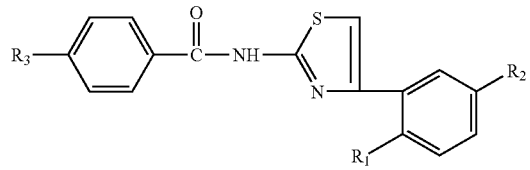

in which R₁, R₂ and R₃ are as defined for (I).

Among these compounds, another sub-group of compounds of formula (Ia) are those in which:

R₁ represents a halogen atom or a $(C_1-C_4)$alkyl, hydroxyl, $(C_1-C_4)$ alkoxy, $(C_3-C_8)$ cycloalkyloxy, allyloxy, cyclopropylmethoxy or $(C_1-C_4)$alkylthio group; and/or R₂ represents a halogen atom or a $(C_1-C_8)$alkyl, trifluoromethyl, $(C_3-C_{10})$cycloalkyl, phenyl, $(C_1-C_8)$alkoxy, allyloxy, $(C_3-C_8)$cycloalkylmethoxy, $(C_3-C_8)$cycloalkyloxy or $(C_3-C_8)$ cycloalkylmethyl group; and/or R₃ represents a group chosen from groups a), b), c), d), e) and f) as defined above for (I).

More particularly, among these compounds, mention may be made of the compounds in which:

R₁ represents a $(C_1-C_4)$alkoxy, cyclopropylmethoxy or $(C_1-C_4)$alkylthio group; and/or R₂ represents a halogen atom or a $(C_1-C_8)$alkyl, trifluoromethyl, $(C_3-C_{10})$cycloalkyl or $(C_1-C_8)$alkoxy group; and/or R₃ represents a group f2 or e2.

Among the compounds of formula (I) of the invention, mention may be made especially of the following compounds:

4-((4-[3-(R)-(acetylamino)pyrrolidin-1-yl]piperidin-1-yl)carbonyl)-N-[4-(5-butyl-2-methoxyphenyl)-1,3-thiazol-2-yl]benzamide;

ethyl (1-(1-(4-(4-(5-butyl-2-methoxyphenyl)thiazol-2-ylcarbamoyl)piperidin-4-yl)carbamate;

N-(4-(5-butyl-2-methoxyphenyl)thiazol-2-yl)-4-(4-(3-(R)-acetylaminopyrrolidin-1-yl)piperidine-1-carbonyl)benzamide;

N-(4-(5-butyl-2-methoxyphenyl)thiazol-2-yl)-4-(4-(tetrahydropyran-4-ylamino)piperidine-1-carbonyl)benzamide;

N-(4-(5-cyclohexyl-2-methoxyphenyl)thiazol-2-yl)-4-(2-(tetrahydropyran-4-ylamino)ethoxy)benzamide;

N-(4-(5-ethyl-2-methoxyphenyl)thiazol-2-yl)-4-(3-(tetrahydropyran-4-ylamino)propyl)benzamide;

N-(4-(5-cyclohexyl-2-ethoxyphenyl)thiazol-2-yl)-4-(4-(pyrrolidin-1-yl)piperidine-1-carbonyl)benzamide;

N-(4-(5-cyclohexyl-2-methoxyphenyl)thiazol-2-yl)-N'-pyrrolidin-2-ylmethylterephthalamide;

N-(4-(5-butyl-2-methoxyphenyl)thiazol-2-yl)-4-(4-(3-(R)-(cyclopropanecarbonylamino)pyrrolidin-1-yl)piperidine-1-carbonyl)benzamide;

N-(4-(5-butyl-2-methoxyphenyl)thiazol-2-yl)-4-(4-(3-(R)-isobutyrylaminopyrrolidin-1-yl)piperidine-1-carbonyl)benzamide;

N-(4-(5-cyclohexyl-2-methoxyphenyl)thiazol-2-yl)-4-(4-(pyrrolidin-1-yl)piperidine-1-carbonyl)benzamide;

N-(4-(5-butyl-2-methoxyphenyl)thiazol-2-yl)-4-(4-(3-(R)-hydroxypyrrolidin-1-yl)piperidine-1-carbonyl)benzamide;

N-(4-(5-butyl-2-methoxyphenyl)thiazol-2-yl)-N'-((S)-(1-ethylpyrrolidin-2-yl)methyl)terephthalamide;

N-(4-(5-butyl-2-methoxyphenyl)thiazol-2-yl)-4-(4-(3-hydroxyazetidin-1-yl)piperidine-1-carbonyl)benzamide;
N-(4-(5-butyl-2-methoxyphenyl)thiazol-2-yl)-4-(4-(3-(S)-acetylaminopyrrolidin-1-yl)piperidine-1-carbonyl)benzamide;
N-(4-(5-ethyl-2-ethoxyphenyl)thiazol-2-yl)-N'-piperidin-3-ylterephthalamide;
N-(4-(5-ethyl-2-ethoxyphenyl)thiazol-2-yl)-4-(4-(3-(R)-hydroxypyrrolidin-1-yl)piperidine-1-carbonyl)benzamide;
N-(4-(5-ethyl-2-ethoxyphenyl)thiazol-2-yl)-N'-((S)-(1-ethylpyrrolidin-2-yl)methyl)terephthalamide;
N-(4-(5-cyclohexyl-2-ethoxyphenyl)thiazol-2-yl)-N'-((S)-(1-ethylpyrrolidin-2-yl)methyl)terephthalamide;
N-(4-(5-cyclohexyl-2-methoxyphenyl)thiazol-2-yl)-N'-((S)-(1-ethylpyrrolidin-2-yl)methyl)terephthalamide;
N-(4-(5-cyclopentyl-2-methoxyphenyl)thiazol-2-yl)-4-(4-(tetrahydropyran-4-ylamino)piperidine-1-carbonyl)benzamide;
N-(4-(5-hexyl-2-methoxyphenyl)thiazol-2-yl)-4-(4-(tetrahydropyran-4-ylamino)piperidine-1-carbonyl)benzamide;
N-(4-(5-cyclohexyl-2-methoxyphenyl)thiazol-2-yl)-4-(4-(3-(R)-acetylaminopyrrolidin-1-yl)piperidine-1-carbonyl)benzamide;
N-(4-(5-butyl-2-methoxyphenyl)thiazol-2-yl)-4-(4-(3-(R)-formylaminopyrrolidin-1-yl)piperidine-1-carbonyl)benzamide;
N-(4-(5-cyclohexyl-2-methoxyphenyl)thiazol-2-yl)-4-(4-(3-(S)-hydroxymethylpyrrolidin-1-yl)piperidine-1-carbonyl)benzamide;
N-(4-(5-propyl-2-methoxyphenyl)thiazol-2-yl)-4-(4-(3-(R)-acetylaminopyrrolidin-1-yl)piperidine-1-carbonyl)benzamide;
N-(4-(5-cyclopentyl-2-methoxyphenyl)thiazol-2-yl)-4-(4-(3-(R)-acetylaminopyrrolidin-1-yl)piperidine-1-carbonyl)benzamide;
ethyl 1-(1-(4-(4-(5-butyl-2-methoxyphenyl)thiazol-2-ylcarbamoyl)benzoyl)piperidin-4-yl)pyrrolidin-3-(R)-yl-propionate;
N-(4-(5-cyclohexyl-2-methoxyphenyl)thiazol-2-yl)-4-(4-(3-(R)-propionylaminopyrrolidin-1-yl)piperidine-1-carbonyl)benzamide;
N-(4-(5-cyclohexyl-2-methoxyphenyl)thiazol-2-yl)-4-(4-(3-(R)-butyrylaminopyrrolidin-1-yl)piperidine-1-carbonyl)benzamide;
N-(4-(5-cyclohexyl-2-ethoxyphenyl)thiazol-2-yl)-4-(4-(3-(R)-acetylaminopyrrolidin-1-yl)piperidine-1-carbonyl)benzamide;
N-(4-(5-ethyl-2-ethoxyphenyl)thiazol-2-yl)-4-(4-(pyrrolidin-1-yl)piperidine-1-carbonyl)benzamide;
N-(4-(5-ethyl-2-ethoxyphenyl)thiazol-2-yl)-N'-((R)-(1-ethylpyrrolidin-2-yl)methyl)terephthalamide;
methyl 1-(1-(4-(4-(5-butyl-2-methoxyphenyl)thiazol-2-ylcarbamoyl)piperidin-4-yl)pyrrolidin-3-yl)carbamate;
N-(4-(5-cyclopentyl-2-methoxyphenyl)thiazol-2-yl)-4-(4-(3-(R)-propionylaminopyrrolidin-1-yl)piperidine-1-carbonyl)benzamide;
N-(4-(5-butyl-2-ethoxyphenyl)thiazol-2-yl)-4-(4-(3-(R)-propionylaminopyrrolidin-1-yl)piperidine-1-carbonyl)benzamide;
N-(4-(5-cyclopentyl-2-ethoxyphenyl)thiazol-2-yl)-4-(4-(3-(R)-propionylaminopyrrolidin-1-yl)piperidine-1-carbonyl)benzamide;
ethyl 1-(1-(4-(4-(5-cyclopentyl-2-ethoxyphenyl)thiazol-2-ylcarbamoyl)piperidin-4-yl)pyrrolidin-3-yl)carbamate.

Some of the compounds of formula (I) may also serve as intermediates for the preparation of other compounds of formula (I), as will be seen in the examples given later.

In the text hereinbelow, the term "protecting group Pg" means a group that firstly allows a reactive function such as a hydroxyl or an amine to be protected during a synthesis, and secondly allows the intact reactive function to be regenerated at the end of the synthesis. Examples of protecting groups and of protection and deprotection methods are given in "Protective Groups in Organic Synthesis", Green et al., $2^{nd}$ Edition (John Wiley & Sons, Inc., New York).

In the text hereinbelow, the term "leaving group" means a group that can be readily cleaved from a molecule by breaking a heterolytic bond, with loss of an electron pair. This group may thus be readily replaced with another group during a substitution reaction, for example. Such leaving groups are, for example, halogens or an activated hydroxyl group such as a mesyl, tosyl, triflate, acetyl, etc. Examples of leaving groups and references for preparing them are given in "Advanced Organic Chemistry", J. March, $3^{rd}$ Edition, Wiley Interscience, pp. 310-316.

In accordance with the invention, the compounds of general formula (I) may be prepared by the process that follows. This process is characterized in that:

a functional derivative of an acid of formula:

in which $R'_3$ represents $R_3$ as defined above for (I) or a precursor of $R_3$, is treated with a 2-aminothiazole derivative of formula:

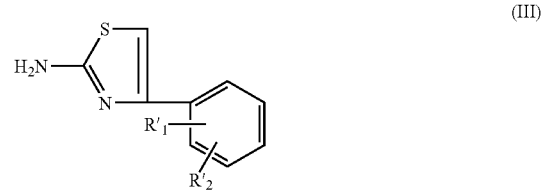

in which $R'_1$ and $R'_2$ represent, respectively, $R_1$ and $R_2$ or precursors of $R_1$ and $R_2$ as defined for (I);

and then, where appropriate, the compound thus obtained of formula:

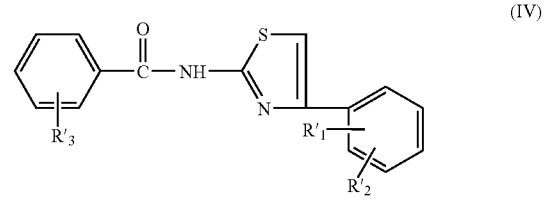

in which $R'_1$, $R'_2$ and $R'_3$ are, respectively, $R_1$, $R_2$ or $R_3$, or precursors of $R_1$, $R_2$ and $R_3$, is converted into a compound of formula (I).

The expression "precursor of $R_1$, $R_2$ or $R_3$" means a substituent that may be converted into $R_1$, $R_2$ or $R_3$ via one or more chemical reactions.

The expression "functional derivative of an acid of formula (II)" means an acid chloride, a mixed or symmetrical anhydride, or the acid suitably activated, for example, with benzotriazol-1-yloxytris(dimethylamino)phosphonium hexafluorophosphate (BOP) or O-benzotriazol-1-yl-N,N,N',N'-tetramethyluronium hexafluorophosphate (HBTU) or O-benzotriazol-1-yl-N,N,N',N'-tetramethyluronium tetrafluoroborate (TBTU), for example.

The first step is performed in an aprotic solvent such as dichloromethane, acetonitrile, THF or DMF, in basic medium.

The compounds of formula (II) are prepared via known methods that vary depending on the value of the substituent $R_3$ or $R'_3$ of the compound of formula (II).

In the schemes that follow, it is considered that the groups $R'_1$ and $R'_2$ which represent $R_1$ and $R_2$ or a precursor of $R_1$ and $R_2$, respectively, may be converted in a subsequent step using reactions known to those skilled in the art.

When one or more substituents $R'_1$, $R'_2$ and/or $R'_3$ represent a group containing an amine or hydroxyl function, these functions may be intermediately protected: an amine function may be protected with an alkanoyl, benzyl, tert-butoxycarbonyl (Boc), benzyloxycarbonyl or 9-fluorenylmethoxycarbonyl (Fmoc) group, for example; a hydroxyl function may be protected in ether or ester form, for example.

To prepare a compound of formula (I) in which $R_3$ represents a group a) as defined above for (I), a compound of formula (II) may be prepared in which $R_3$ represents a group a) by performing the reaction Scheme below, illustrated for a1), followed by using the process according to the invention.

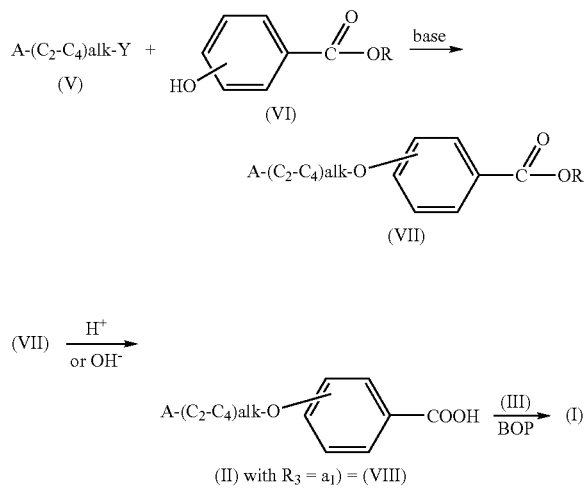

Y=leaving group

R=$(C_1-C_4)$alkyl.

The process may also be performed according to Scheme 1, but replacing in the compound of formula (V) the leaving group Y with a hydroxyl group, according to the Mitsunobu reaction, Bull. Chem. Soc. Japan, 1967, 40, 2380.

Alternatively, to prepare a compound of formula (I) in which $R_3$ represents a group a), a compound of formula (IV) containing a group $R'_3$ that is a precursor of $R_3$ may be prepared, and may then be converted in a subsequent step into the group $R_3$ according to the following reaction Scheme:

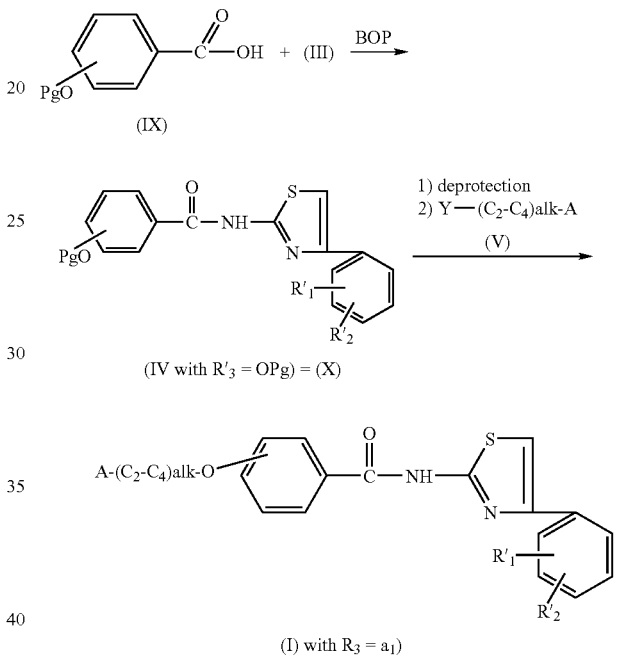

Y: leaving group.

Pg: protecting group for oxygen, such as tert-butyl, benzoyl or arylsulphonyl, for example.

By replacing the compound of formula (V) with a compound of formula Y-E in which E is as described above, the substituent $R_5$ being optionally replaced with a protecting group for nitrogen, a compound of formula (I) in which $R_3$=a3) is obtained.

A compound of formula (I) in which $R_3$ represents a) may also be prepared starting with a compound comprising a group $R'_3$, which is a precursor of $R_3$, according to the reaction Scheme below:

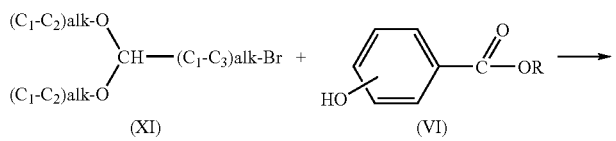

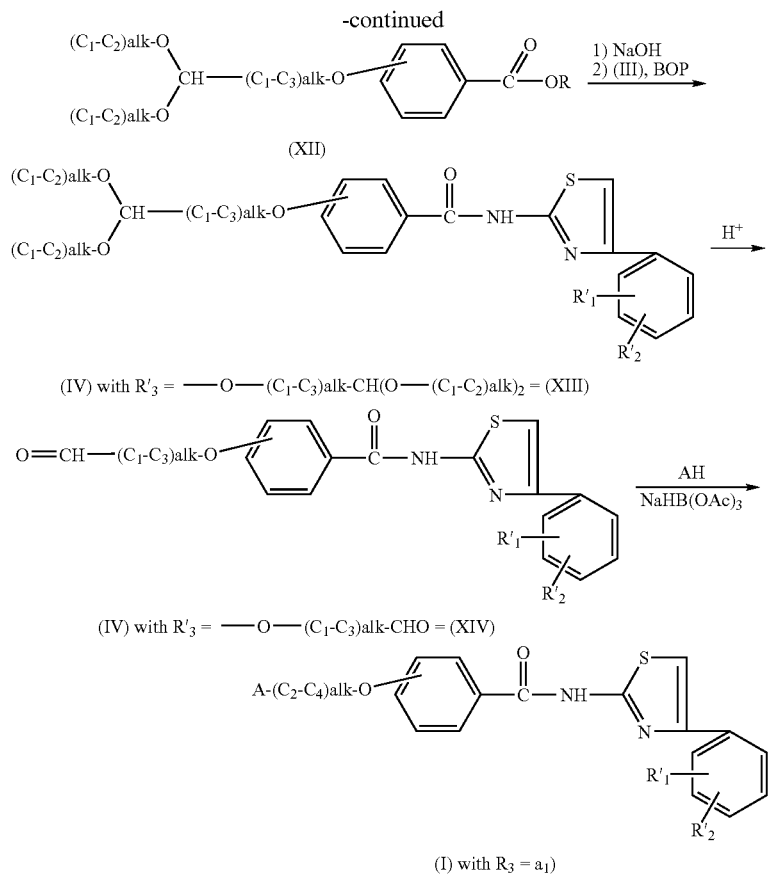
In the final step, the addition of the amine is performed according to Synth. Commun., 1998, 28 (10), 1897-1905, J. Org. Chem., 1992, 57 (11), 3218-3225, J. Org. Chem., 1996, 61, 3849-3862, Tetrahedron Lett., 1990, 31, 5595-5598.
Another way of preparing a compound of formula (I) in which $R_3$ represents a group a), from a compound of formula (IV) containing $R'_3$, which is a precursor of $R_3$, is shown in the reaction Scheme below:
SCHEME 4
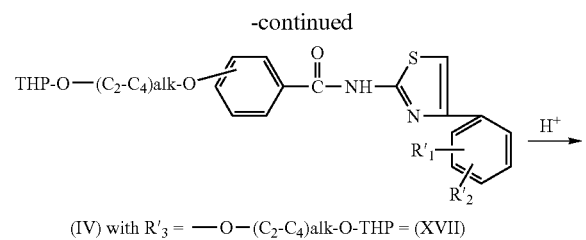
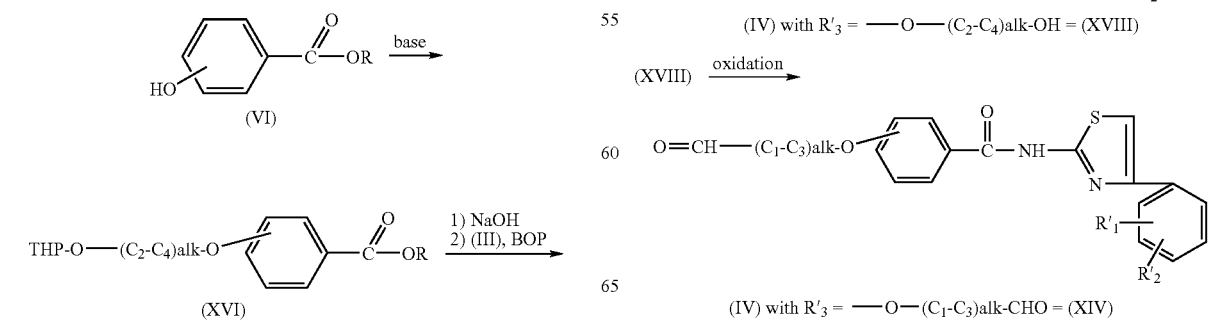

-continued (XVIII) $\xrightarrow{R'SO_2Cl}{base}$

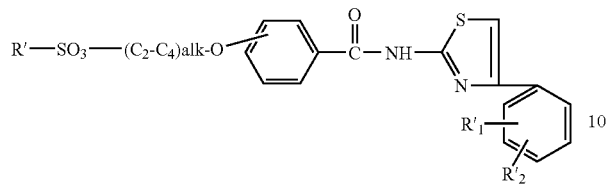

(IV) with R'$_3$ = —O—(C$_2$-C$_4$)alk-SO$_3$—R' = (XIX)

(XIX) $\xrightarrow{AH}$

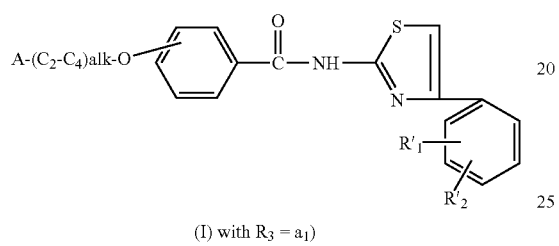

(I) with R$_3$ = a$_1$)

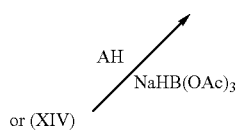

or (XIV)

R'=methyl or tolyl
THP=tetrahydropyran-2-yl.

The conversion of the compound of formula (XVIII) by oxidation may be performed via a Swern oxidation, for example.

An example of the preparation of a compound of formula (II) in which R'$_3$=a1) is described below:

SCHEME 5

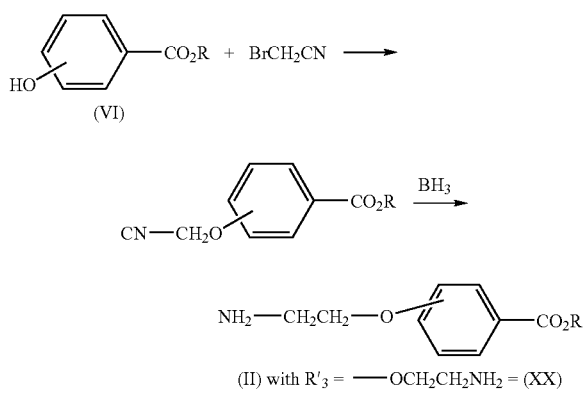

(II) with R'$_3$ = —OCH$_2$CH$_2$NH$_2$ = (XX)

Starting with compound (XX) thus obtained, various compounds (II) may then be prepared by suitably substituting the primary amine.

To prepare a compound of formula (I) in which R$_3$ is a group a2) or a3), the process may also be performed via the action of a compound of formula (II) in which R$_3$=a2) or a3)

on a compound of formula (III); the compound of formula (II) being prepared according to the following reaction Scheme illustrated for a2):

B—(C$_1$-C$_4$)alk-OH + CH$_3$SO$_2$Cl ⟶

B—(C$_1$-C$_4$)alk-O—SO$_2$CH$_3$
(XXI)

(XXI) + HO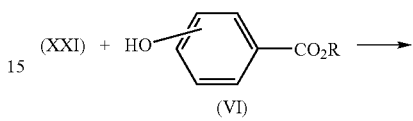—CO$_2$R ⟶

(VI)

B—(C$_1$-C$_4$)alk-O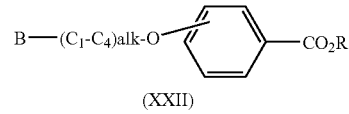—CO$_2$R
(XXII)

(XXII) $\xrightarrow[\text{or OH}^-]{H^+}$ (II) with R$_3$ = a$_2$)

The acids of formula:

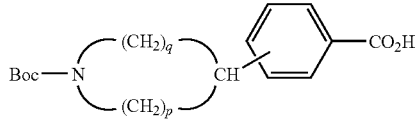

allow the preparation of compounds of formula (IV) in which R'$_3$=c), via action on an aminothiazole of formula (III).

To prepare a compound of formula (I) in which R$_3$ is a group b), the process may be performed via the action of a compound of formula (II) in which R$_3$=b) on a compound of formula (III); the compound of formula (II) or the ester thereof being prepared according to the following reaction Scheme:

SCHEME 6

O=CH—(C$_1$-C$_3$)alk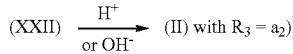—CO$_2$R $\xrightarrow{AH}{NaHB(OAc)_3}$ (XXIII)

A-(C$_1$-C$_4$)alk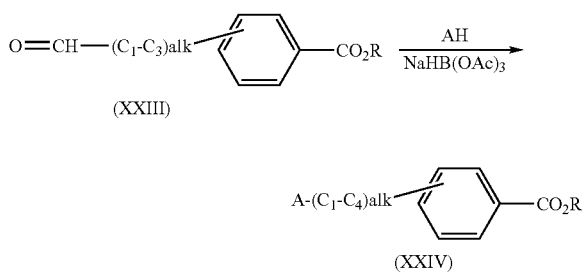—CO$_2$R (XXIV)

A compound of formula (I) in which R$_3$ is a group b) may also be prepared by performing the process according to the following reaction Scheme, which repeats the steps of Scheme 3, while adapting them to the present case:

SCHEME 7

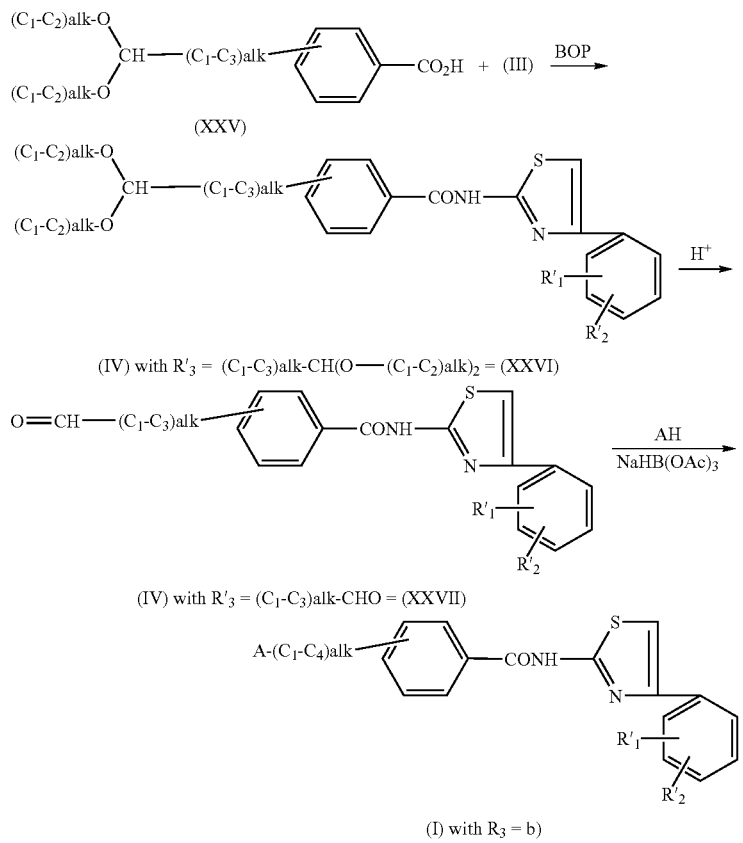

In the particular case in which a compound of formula (I) is prepared in which $R_3$ represents a group b), with $(C_1-C_4)$alk= $(CH_2)_3$, a compound of formula (IV) in which $R'_3$ is a precursor of b) may be converted into a compound of formula (I) according to the following reaction Scheme:

SCHEME 8

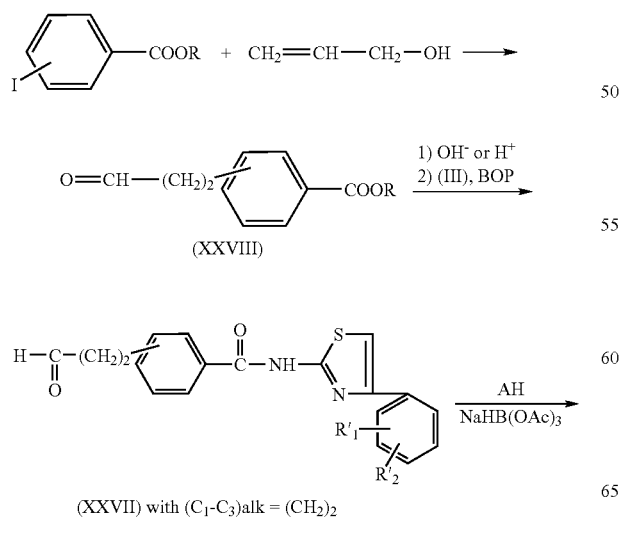

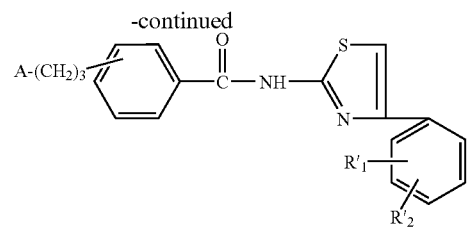

The compound of formula (XXVII) may also be obtained via the action of iodobenzoic acid on a compound of formula (III), followed by the action of 2-propen-1-ol on the compound thus obtained of formula (XXVIIa):

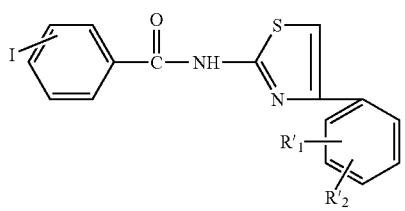

A compound of formula (I) in which $R_3$ is b) may also be prepared according to the following reaction Scheme:

SCHEME 9

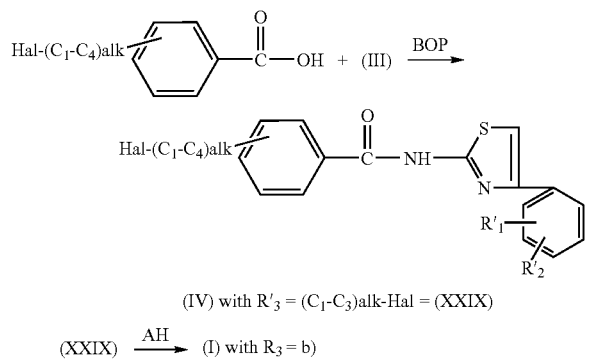

(IV) with R'$_3$ = (C$_1$-C$_3$)alk-Hal = (XXIX)

(XXIX) $\xrightarrow{AH}$ (I) with R$_3$ = b)

Hal: halogen atom, preferably chlorine.

Similarly, a compound of formula (I) in which R$_3$=b) may also be prepared from a compound of formula (II) prepared according to the following Scheme:

SCHEME 10

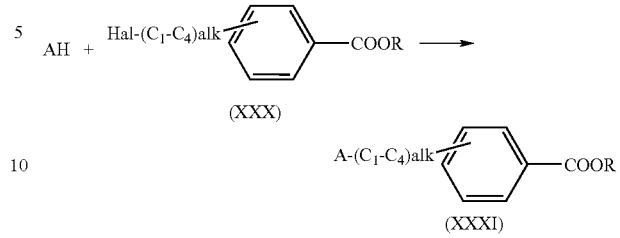

The compounds of formula (II) in which R$_3$=c) may be prepared according to Syn. Lett., 1998, 4, 379-380.

The processes for preparing the compounds of formula (I) in which R$_3$ is a group d) are performed in a manner similar to those described for the preparation of the compounds (I) in which R$_3$=b).

To prepare a compound of formula (I) in which R$_3$ is a substituted amide group (groups e) and f)), the process may be performed according to either of Schemes 11 and 12 below, which illustrate the case in which R$_3$=e1):

SCHEME 11

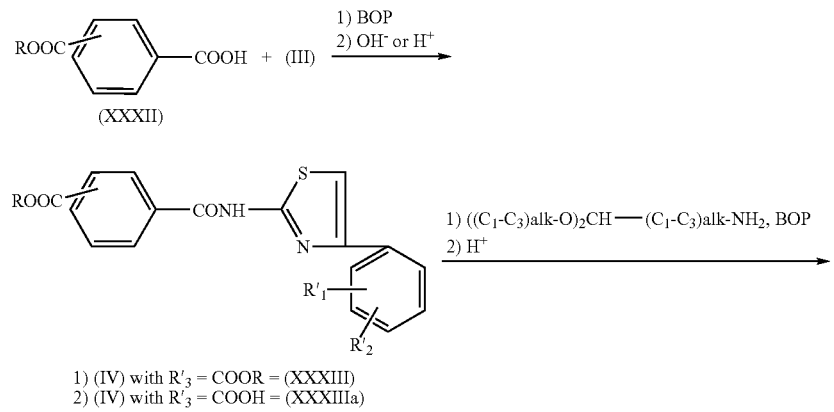

1) (IV) with R'$_3$ = COOR = (XXXIII)
2) (IV) with R'$_3$ = COOH = (XXXIIIa)

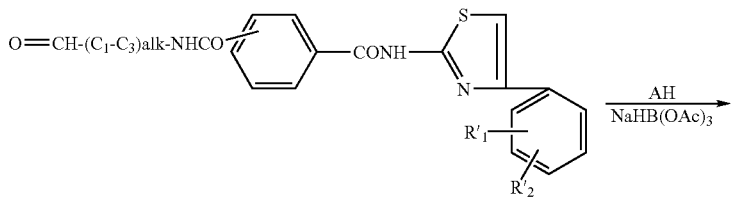

1) (IV) with R'$_3$ = —CONH—(C$_1$-C$_3$)alk-CH(O-(C$_1$-C$_2$)alk)$_2$ = (XXXIV)
2) (IV) with R'$_3$ = —CONH—(C$_1$-C$_3$)alk-CHO = (XXXIVa)

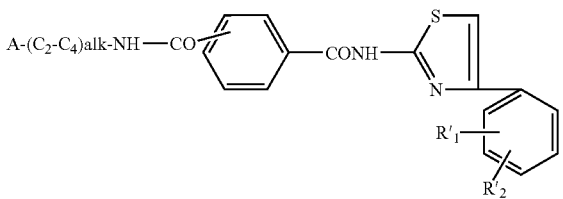

(I) with R$_3$ = e$_1$)

R = (C$_1$-C$_4$)alkyl

SCHEME 12

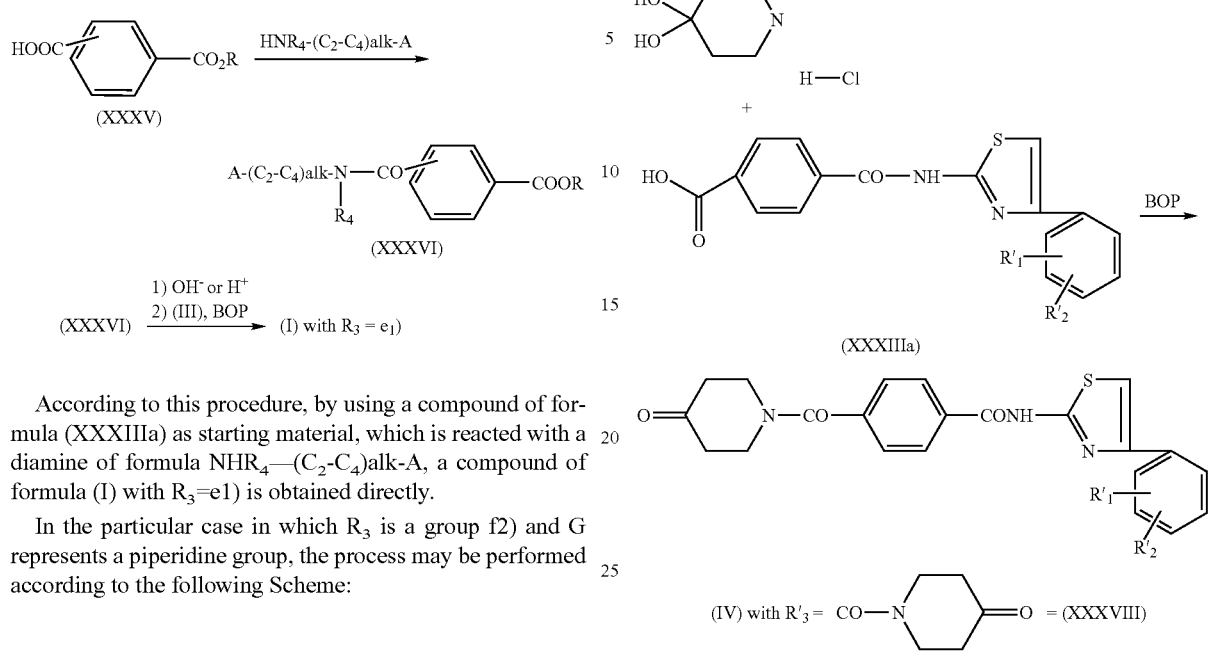

According to this procedure, by using a compound of formula (XXXIIIa) as starting material, which is reacted with a diamine of formula $NHR_4$—$(C_2$-$C_4)$alk-A, a compound of formula (I) with $R_3$=e1) is obtained directly.

In the particular case in which $R_3$ is a group f2) and G represents a piperidine group, the process may be performed according to the following Scheme:

SCHEME 13

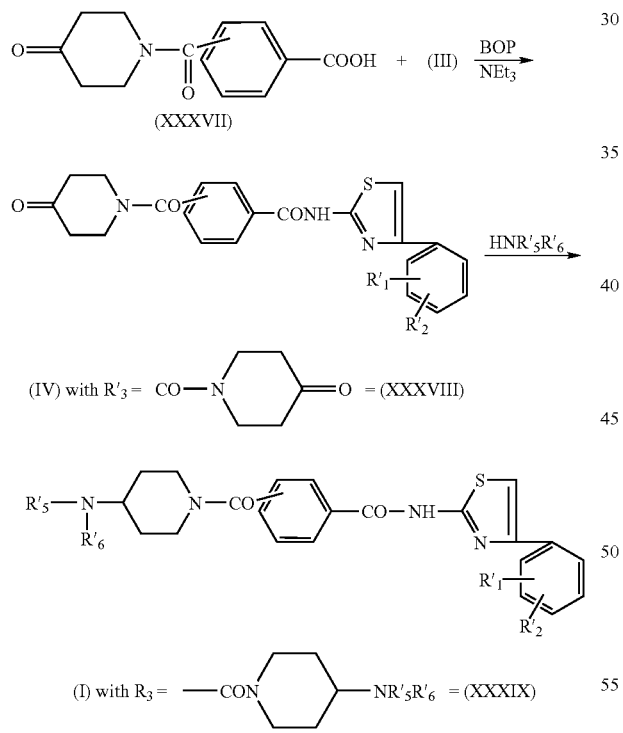

The compounds thus obtained may then be converted into compounds in which $NR_5R_6$ is as defined in the general formula (I) by deprotection and functionalization of the amine $NR'_5R'_6$, according to the methods known to those skilled in the art.

The compounds of formula (XXXVIII) may also be prepared from the compounds of formula (XXXIIIa) according to the following scheme:

To prepare a compound of formula (I) in which $R_3$ is a group f2) and G represents a piperidinyl radical, the process may also be performed according to the following Scheme:

SCHEME 14

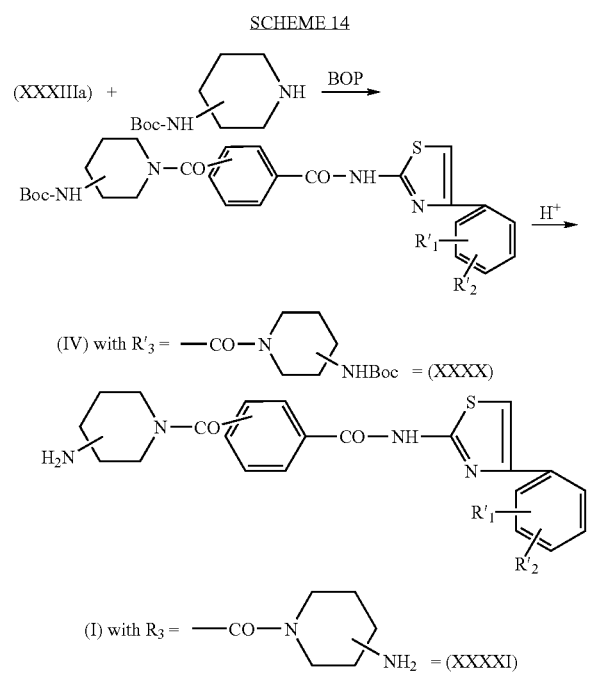

Starting with the compound (XXXXI) thus obtained, various compounds of formula (I) in which $R_3$=f2) may then be prepared by suitably substituting the primary amine function.

For example, via the action of tetrahydropyran-4-one, a compound of formula (I) is prepared in which $R_3$ is a group:

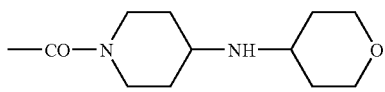

To prepare a compound of formula (I) in which $R_3$=e) or f), the process may be performed according to the scheme below which illustrates the case where $R_3$=f2) and G represents a piperidine:

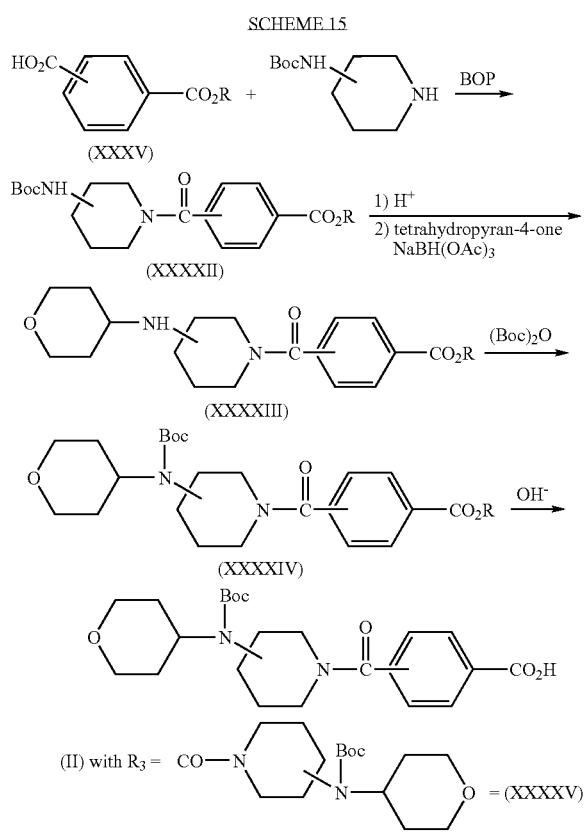

or, by inverting the first steps, the process is performed according to the following scheme:

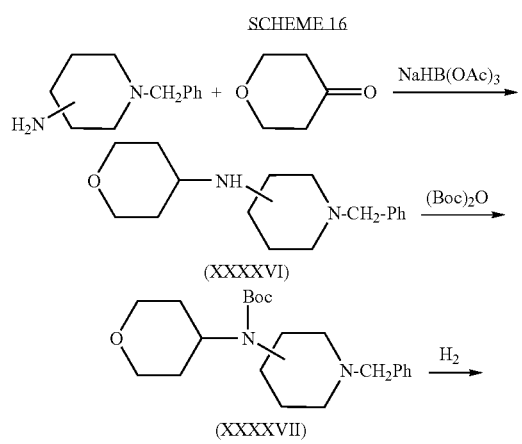

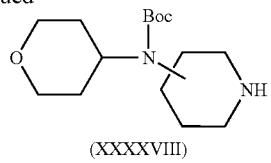

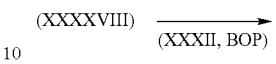

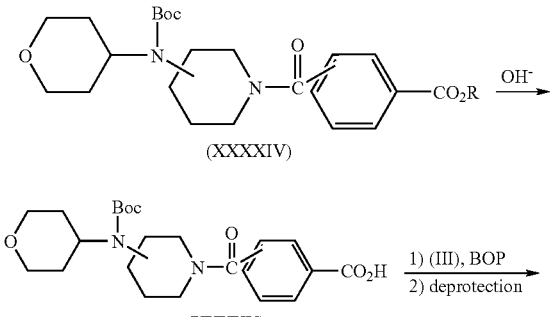

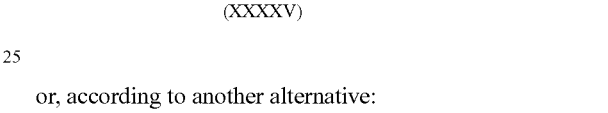

or, according to another alternative:

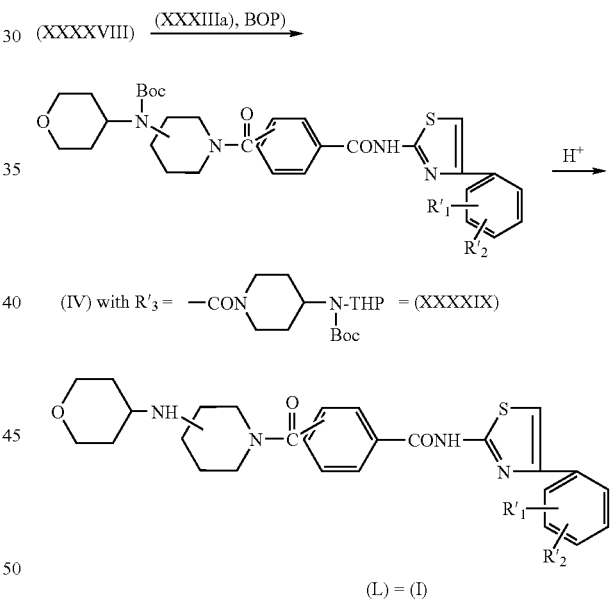

Ph=phenyl
THP=tetrahydropyran-4-yl.

In the processes represented in Schemes 14, 15 and 16, a protecting group for nitrogen that may be used is Boc, as shown, or any other suitable protecting group Gp, for example an alkanoyl group such as formyl or acetyl, a benzyl group, a 9-fluorenylmethoxycarbonyl (Fmoc) group or a benzyloxycarbonyl or tert-butoxycarbonyl (Boc) group.

The aminothiazoles of formula (III) are prepared by known methods such as those described in documents EP 518 731, EP 611 766 and WO 99/15525.

In general, thiourea is reacted with a halo ketone of formula 4 according to the following reaction scheme:

SCHEME 17

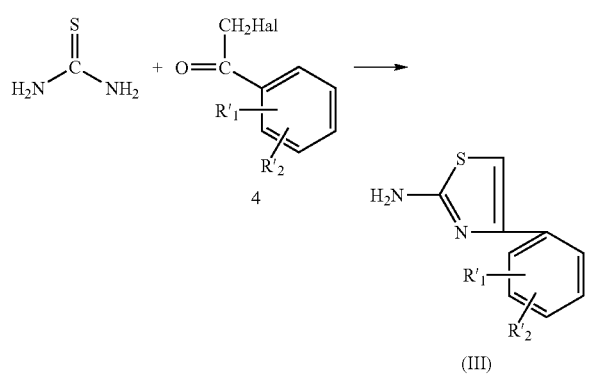

The substituents R'$_1$ and R'$_2$ have the values indicated above, i.e. R'$_1$ and R'$_2$ represent R$_1$ and R$_2$, respectively, as defined for (I) or precursor groups of R$_1$ and R$_2$; Hal represents a halogen atom, preferably bromine, chlorine or iodine.

The halo ketones of formula 4 may be prepared via processes known to those skilled in the art. For example, the bromo ketones may be obtained by the action of bromine, cupric bromide or phenyltrimethylammonium tribromide (PTT) on an acetophenone derivative of formula:

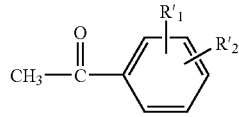

5 in which R'$_1$ and R'$_2$ have the values indicated above, in an organic solvent such as ethyl acetate, a chlorinated solvent or a mixture thereof, or alternatively an alcohol.

When the acetophenone derivative of formula 5 is not commercially available, it may be prepared via various methods:
- a Friedel-Crafts reaction on the benzene substituted with R'$_1$ and R'$_2$, which is reacted with acetyl chloride or acetic anhydride, in the presence of a Lewis acid, for instance AlCl$_3$ or TiCl$_4$;
- the action of acetyl chloride in the presence of palladium on the benzene substituted with R'$_1$ and R'$_2$ after deprotonation of the benzene, for example via the action of butyllithium, followed by addition of zinc chloride or manganese iodide. This procedure may be used to prepare an acetophenone derivative of formula 5 in which R'$_2$=R$_2$=(C$_1$-C$_4$) perfluoroalkyl;
- Fries rearrangement: starting with an acetoxybenzene derivative of formula:

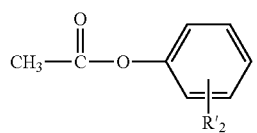

6 via the action of a Lewis acid, a hydroxyacetophenone derivative is obtained, of formula:

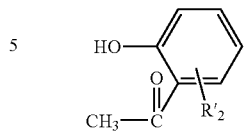

7

The hydroxyl function corresponds to a group R'$_1$ that may be converted in a subsequent step into a group —O-Z such as (C$_1$-C$_8$)alkoxy, trifluoromethoxy, trifluoroethoxy, allyloxy, (C$_3$-C$_8$) cycloalkylmethoxy or (C$_3$-C$_8$) cycloalkyloxy.

The conversion of R'$_1$ into R$_1$ may be performed either on the aminothiazole of formula (III) or on a compound of formula (I).

The benzene derivatives substituted with R'$_1$ and R'$_2$ are commercially available or may be prepared via methods known to those skilled in the art.

For example, to prepare a compound in which R$_1$ is a group —O—Z as defined above, the process is performed in the following manner:

SCHEME 18

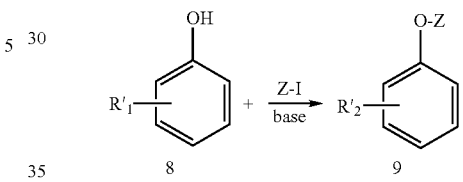

A halobenzene derivative may also be substituted according to the scheme below:

SCHEME 19

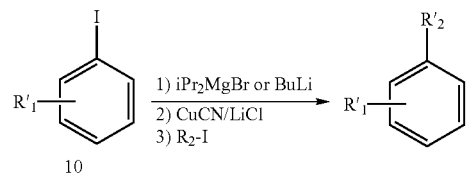

In the particular case in which R$_2$ represents a (C$_1$-C$_4$) perfluoroalkyl, the process may also be performed according to the reaction scheme below:

SCHEME 20

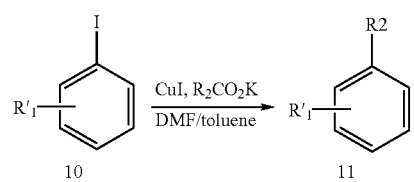

Acids of formula (II) in which R'$_3$ represents R$_3$, which is an ether group as defined for (I) by a), are described especially in Arch. Pharm., 1962, 295, 292-304; Eur. J. Med. Chem., 1994, 26 (9), 675-686; J. Med. Chem., 2002, 45 (16), 3406-3417; and in documents: WO-02/53534; WO-01/00206; WO-96/21656; WO-00/39087; EP-A-62504; EP-A-393 607; EP-A-997 465.

The acids of formula (II) in which R'$_3$ represents R$_3$ which is a group b) or c) as defined for (I) are generally novel. The 4-((1-methylpiperidin-4-yl)methylbenzoic and 4-((1-ethylpiperidin-4-yl)methylbenzoic acid esters are described in Pesticide Sciences, 1995, 44 (1), 96-102.

Thus, a subject of the present invention is also compounds of formula:

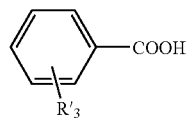

(IIb)

in which R'$_3$ represents R$_3$ chosen from:

a group b): (C$_1$-C$_4$) alk-A or c): B in which the groups A and B are as defined for (I), on condition that when (C$_1$-C$_4$)alk represents a methylene, B is other than piperidinyl; or R'$_3$ represents a precursor of R$_3$, especially a group in which the amine and/or hydroxyl functions that may be present are protected.

The esters, especially the (C$_1$-C$_4$) aliphatic esters or benzyl esters which are unsubstituted or substituted on the phenyl with a methoxy group, of the acids of formula (IIb) are also novel and form part of the invention.

The acids of formula (II) in which R'$_3$ represents R$_3$ which is a group e) or f) as defined for (I) are generally novel. Compounds of formula (II) in which R$_3$ represents a group e1) are described in documents WO-98/56760 and U.S. Pat. No. 5,411,984.

Thus, a subject of the present invention is also compounds of formula:

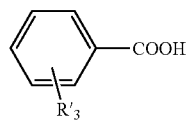

(IIe)

in which R'$_3$ represents R$_3$ chosen from a group e2), e3), f1), f2), f3), f4), f5) and f6) as defined for (I); or R'$_3$ represents a group that is a precursor of R$_3$, especially a group in which the amine and/or hydroxyl functions that may be present are protected.

The esters, especially the (C$_1$-C$_4$) aliphatic esters or benzyl esters which are unsubstituted or substituted on the phenyl with a methoxy group, of the acids of formula (IIe) are also novel and form part of the invention.

In particular, the acids of formula:

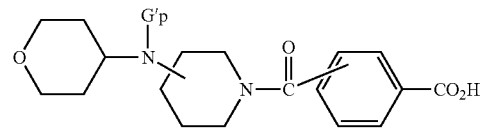

(XXXXV) or (XXXXIII)

in which G'p represents hydrogen or a protecting group for nitrogen such as: Boc, Fmoc, benzyloxycarbonyl, benzyl or (C$_1$-C$_4$) alkanoyl, and also the (C$_1$-C$_4$)alkyl esters thereof of formula (XXXXIV) or the benzyl esters thereof which are unsubstituted or substituted on the phenyl with a methoxy group, are novel and constitute a specific subject of the present invention.

The intermediate compounds of formulae (XXXXVI), (XXXXVII) and (XXXXVIII) that are useful for preparing compounds of formula (XXXXV) are also novel.

Thus, a subject of the present invention is also a compound of formula:

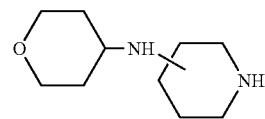

(XXXXVIIIa)

in which the amine functions are free or protected with a protecting group, for instance an Fmoc, benzyl, tert-butoxycarbonyl, benzyloxycarbonyl or (C$_1$-C$_4$)alkanoyl group.

The 2-aminothiazoles of formula (III) are generally known, especially from the following documents: EP-A-819 681, EP-A-44442 or Indian J. Chem., section B, 1987, 26B (3), 287-289.

The intermediate compounds of formula (IV), i.e. the compounds of formulae X, XIII, XIV, XVII, XVIII, XIX, XXVI, XXVII, XXVIIa, XXIX, XXXIII, XXXIIIa, XXXIV, XXXIVa, XXXVIII, XXXX and XXXXIX are novel and constitute a further subject of the present invention.

Moreover, the intermediate compounds of formula (IV) in which the group R'$_3$ comprises a protected amine function, i.e. a group —NGp in place of a group —NR$_5$, are also novel.

A subject of the invention is also the compounds of formula:

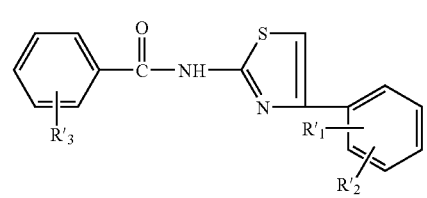

(IV)

in which:

R'$_1$ and R'$_2$ represent, respectively, R$_1$ or R$_2$ or precursors of R$_1$ and R$_2$ as defined for the compounds of formula (I); more particularly, R'$_1$ and R'$_2$ represent, respectively, R$_1$ and R$_2$;

R'$_3$ represents a group chosen from:
- —OPg, Pg being a protecting group such as tert-butyl, benzoyl or arylsulphonyl (phenylsulphonyl, tolylsulphonyl or naphthylsulphonyl);
- —O—(C$_1$-C$_3$)alk-Q, Q being a dimethoxymethyl, diethoxymethyl or formyl group;
- —O—(C$_2$-C$_4$)alk-OX, X representing a hydrogen atom, a tetrahydropyranyl group or a group SO$_2$R', R' being a methyl or tolyl group;
- —(C$_1$-C$_3$)alk-Q;
- —(C$_1$-C$_4$)alk-Hal, Hal representing a halogen atom;
- —I;
- —COOH; —COOR with R representing a hydrogen atom, a (C$_1$-C$_4$)alkyl or a benzyl which is unsubstituted or substituted on the phenyl with a methoxy group;
- —CONH—(C$_1$-C$_3$)alk-Q;

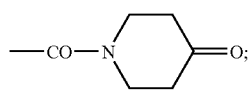

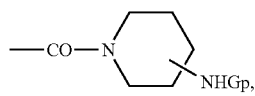

Gp representing a protecting group for nitrogen, such as Fmoc, (C$_1$-C$_4$)alkanoyl, benzyl, benzyloxycarbonyl or tert-butoxycarbonyl;

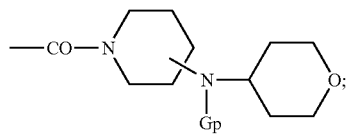

a) a1) —O—(C$_2$-C$_4$)alk-A';
   a2) —O—(C$_1$-C$_4$)alk-B';
   a3) —O-E';
b) —(C$_1$-C$_4$)alk-A';
c) —B';
d) d1) —(C$_1$-C$_4$)alk-NR$_4$—(C$_2$-C$_3$) alk-A';
   d2) —(C$_1$-C$_4$) alk-NR$_4$—(C$_1$-C$_3$)alk-B';
e) e1) —CONR$_4$—(C$_2$-C$_4$)alk-A';
   e2) —CONR$_4$—(C$_1$-C$_4$)alk-B';
   e3) —CONR$_4$-E';
f) f1) —CO-D-(C$_1$-C$_2$)alk-A';
   f2) —CO-G-A';

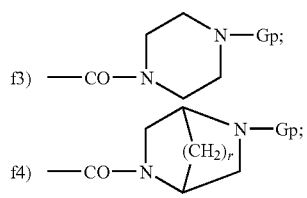

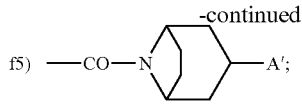

in which:
A', B' and E' represent, respectively, the groups A, B and E as defined for (I) in which R$_5$ is replaced with Gp;
Gp represents a protecting group for nitrogen such as:
Boc, Fmoc, (C$_1$-C$_4$)alkanoyl, benzyloxycarbonyl or benzyl.

More particularly, the present invention relates to the compounds of formula (IV) in which:
R'$_1$ is in position –2 of the phenyl and is such as R$_1$, defined for (I);
R'$_2$ is in position –5 of the phenyl and is such as R$_2$ defined for (I);
R'$_3$ is in position –4 of the other phenyl group and is as defined above.

The preparations and examples that follow illustrate the preparation of certain compounds in accordance with the invention. These examples are not limiting and merely illustrate the present invention. The numbers of the compounds illustrated refer to those given in the tables later. In the description, the following abbreviations are used:
RT: room temperature
dec.: decomposition
DCM: dichloromethane
DMF: dimethylformamide
Et$_3$N: triethylamine
BOP: benzotriazol-1-yl-oxytris(dimethyl-amino)phosphonium hexafluorophosphate
Boc: tert-butyloxycarbonyl
ether: ethyl ether
MTBE: methyl tert-butyl ether
Me: methyl
Et: ethyl
Pr: propyl
Bu: butyl
Pn: pentyl
Hex: hexyl
DIPEA: diisopropylethylamine
THP: tetrahydropyran-4-yl.

The compounds are characterized by:
The proton magnetic resonance ($^1$H NMR) spectra are recorded at 200 MHz in DMSO-d$_6$, using the DMSO-d$_6$ peak as reference. The chemical displacements δ are expressed in parts per million (ppm). The signals observed are expressed as follows: s: singlet; bs: broad singlet; d: doublet; dd: doubled doublet; t: triplet; dt: doubled triplet; q: quartet; m: unresolved peak; mt: multiplet.

For all the compounds synthesized in the Preparations and Examples that follow, it is checked that the NMR spectra recorded are in accordance with the expected structure.

The compounds according to the invention are analyzed by LC/UV/MS (liquid chromatography/UV detection/mass spectrometry) coupling. The molecular peak (MH$^+$) and the retention time (t) are measured.

A machine sold by Waters and a column of 2.1×50 mm are used, with 3.5 μm particles, at room temperature, with a flow rate of 0.4 ml/minute.

The eluent is made up as follows:
solvent A: 0.005% trifluoroacetic acid (TFA) in water
solvent B: 0.005% TFA in acetonitrile.

|  | Time (minutes) | % B |
|---|---|---|
| Gradient | 0 | 0 |
|  | 10 | 90 |
|  | 15 | 90 |
|  | 15.5 | 0 |
|  | 20 | 0 |

The UV detection is performed at 210±8 nm and the mass detection is performed after electronic ionization (electrospray ionization or ESI) in positive mode.

Preparation of the Intermediates of Formula (III)

Preparation 1.1

4-(2-Methoxy-5-propoxyphenyl)-1,3-thiazol-2-amine

A) 1-(2-Hydroxy-5-propoxyphenyl)ethanone 10 g of 2,5-dihydroxyacetophenone suspended in 100 ml of acetone are placed in a 500 ml round-bottomed flask and 9.14 g of anhydrous $K_2CO_3$ are added, followed by addition of 12.4 g of propyl iodide. The reaction medium is refluxed for 30 hours. After cooling to room temperature, the medium is filtered through Celite® and then concentrated. The brown oil obtained is taken up in EtOAc, filtered, washed with water, with 2M HCl solution and then with saturated NaCl solution. The organic phase is evaporated to give a black paste. The paste is taken up in chloroform and filtered. The medium is concentrated to give 11.4 g of a black solid. This solid is taken up in absolute ethanol. The solution is placed in a freezer for 10 minutes; a solid precipitates out, and is collected by filtration. The filtrate is concentrated, taken up in ethanol, cooled in a freezer and then filtered again. This operation is repeated four more times to give 8.35 g of the expected compound in the form of a powder.

B) 1-(2-Methoxy-5-propoxyphenyl)ethanone 49.8 g of $K_2CO_3$ are added to a solution of 35 g of the above solid in 350 ml of DMF, followed by addition of 22.4 ml of methyl iodide. The reaction medium is heated for 12 hours at 60° C. After cooling to room temperature, the medium is filtered through Celite®, diluted with ether and washed with 2M HCl solution. The aqueous phase is extracted twice with ether. The combined organic phases are washed with dilute sodium hydroxide solution and then washed twice with water and with saturated NaCl solution. The organic phase is dried over $MgSO_4$ and then evaporated to give 35.55 g of a brown oil. The oil is distilled under reduced pressure at 115° C. to give 32.8 g of the expected compound in the form of an oil.

C)
2-Bromo-1-(2-methoxy-5-propoxyphenyl)ethanone 4.8 ml of bromine are added dropwise to a solution of 16.4 g of the oil obtained in the preceding step in 100 ml of methanol. The medium is stirred for 30 minutes at room temperature and then evaporated. The oil obtained is taken up in dichloromethane, washed three times with water and then dried over $MgSO_4$ and then evaporated to give 24.5 g of a brown oil.

D) 4-(2-Methoxy-5-propoxyphenyl)-1,3-thiazol-2-amine 24.5 g of thiourea are added to a solution of 42 g of the bromo ketone prepared in the preceding step in 200 ml of ethanol. The medium is refluxed for 1 hour 30 minutes. The medium is then placed in a refrigerator for 12 hours, and then filtered. The solid thus collected is rinsed with a small amount of cold ethanol and then with ether. 25 g of hydrobromide are recovered.

The solid is suspended in a water/dichloromethane mixture and the base is restored by adding sodium hydroxide. The aqueous phase is extracted twice with dichloromethane. The combined organic phases are dried over $MgSO_4$ and then evaporated. The oil obtained is chromatographed on silica gel to give 12 g of the expected product in the form of powder. m.p.=76° C.

Preparation 1.2

4-(5-Butyl-2-methoxyphenyl)-1,3-thiazol-2-amine

A) 4-Butylphenyl acetate

A solution of 10 g of 4-n-butylphenol, 10 ml of $Ac_2O$ and 8 ml of pyridine is stirred at reflux in 10 ml of dichloromethane. After 2 hours, the medium is cooled to room temperature, diluted with dichloromethane, washed with water, washed with 1M HCl solution, washed with saturated $CuSO_4$ solution, washed with water and dried over $MgSO_4$. After evaporation, 10.8 g of the expected compound are recovered in the form of an oil.

B) 1-(5-Butyl-2-hydroxyphenyl)ethanone 3.22 g of $AlCl_3$ are added portionwise to 5 g of the preceding oil in a 100 ml round-bottomed flask. The medium is heated at 130° C. for one hour. After cooling to room temperature, a solution of ice-cold water acidified with 35% HCl is poured onto the crude reaction product. The medium is placed in an ultrasonication bath. EtOAc is added to obtain, after 15 minutes, dissolution of the medium. The aqueous phase is extracted 3 times with EtOAc and the organic phases are washed with water and then with saturated NaCl solution. After drying over $MgSO_4$ and evaporation, 4.5 g of a yellow oil are obtained.

C) 1-(5-Butyl-2-methoxyphenyl)ethanone 1.44 g of $K_2CO_3$ and then 0.648 ml of methyl iodide are added to a solution of 1 g of the preceding oil in 10 ml of DMF. The medium is heated at 60° C. overnight. After cooling to room temperature, the medium is filtered through Celite®, diluted with ether and washed with 2M HCl solution. The aqueous phase is extracted twice with ether. The combined organic phases are washed with dilute sodium hydroxide solution and then washed twice with water and with saturated NaCl solution. The organic phase is dried over $MgSO_4$ and then evaporated to give 1.27 g of a brown oil. The oil is purified by chromatography to give 0.66 g of the expected compound.

D) 4-(5-Butyl-2-methoxyphenyl)-1,3-thiazol-2-amine 0.19 ml of bromine is added to a solution of 0.66 g of the product from the preceding step in 10 ml of methanol. The medium is stirred for 10 minutes and then evaporated and taken up in dichloromethane. The organic phase is washed 3 times with water and then dried over MgSO$_4$. 0.79 g of the expected product is recovered after evaporation. This compound is dissolved in 5 ml of ethanol in the presence of 0.46 g of thiourea and the medium is refluxed for 2 hours 30 minutes. A solid precipitates during cooling to room temperature. The solid thus collected is rinsed with a small amount of cold ethanol and then with ether. 0.6 g of the hydrobromide is thus recovered.

The solid is suspended in a water/dichloromethane mixture and the base is restored by addition of sodium hydroxide. The aqueous phase is extracted twice with dichloromethane. The combined organic phases are dried over MgSO$_4$ and then evaporated to give 0.34 g of a yellow oil, which crystallizes slowly. The mother liquors are evaporated and then stirred in a water/dichloromethane mixture and the base is restored by addition of sodium hydroxide. The aqueous phase is extracted twice with dichloromethane. The combined organic phases are dried over MgSO$_4$ and then evaporated. The oil obtained is chromatographed on silica gel to give 0.18 g of the expected compound; m.p.=48° C.

Preparation 1.3

4-(5-Cyclohexyl-2-methoxyphenyl)-1,3-thiazol-2-amino-1-cyclohexyl-4-methoxybenzene A) 7.84 g of K$_2$CO$_3$ are added to a solution of 5 g of 4-cyclohexylphenol in 60 ml of DMF, followed by addition of 3.53 ml of methyl iodide. The medium is heated at 60° C. overnight. After cooling to room temperature, the medium is filtered through Celite® and then diluted with ether and hydrolyzed with water. The aqueous phase is acidified and then extracted with 3×50 ml of ether. The combined organic phases are washed with dilute sodium hydroxide solution and then washed twice with water and with saturated NaCl solution. The organic phase is dried over MgSO$_4$ and then evaporated to give 4.31 g of the expected compound in the form of a solid. m.p.=67° C.

B) 1-(5-Cyclohexyl-2-methoxyphenyl)ethanone

A suspension of 5.6 g of AlCl$_3$ in 40 ml of dichloromethane is cooled to –10° C. 3 ml of AcCl and 4 g of the compound from the preceding step are added. The medium is stirred for one hour at –10° C. and then poured into a beaker containing ice mixed with 35% HCl. After separation of the phases by settling, the combined organic phases are dried over MgSO$_4$ and then evaporated to give 4.54 g of the expected product.

C) 4-(5-Cyclohexyl-2-methoxyphenyl)-1,3-thiazol-2-amine 1.16 ml of bromine are added dropwise to a solution of 4.5 g of the product from the preceding step in 25 ml of methanol. The medium is stirred for 30 minutes at room temperature and then becomes very viscous. A further 5 ml of methanol are added, followed by addition of 3.23 g of thiourea. The medium is refluxed for 2 hours. After cooling to room temperature, a solid precipitates out. The solid is collected and then rinsed with a small amount of cold methanol. The solid is suspended in a water/dichloromethane mixture and the base is restored by addition of sodium hydroxide. The aqueous phase is extracted twice with dichloromethane. The combined organic phases are dried over MgSO$_4$ and then evaporated to give 3.33 g of the expected compound in the form of a solid. m.p.=113° C.

Preparation 1.24

4-(5-Pentafluoroethyl-2-methoxyphenyl)thiazol-2-ylamine

A) 1-Methoxy-4-pentafluoroethylbenzene 8.3 g of potassium pentafluoropropionate and 9.8 g of CuI are introduced into a 500 ml three-necked flask equipped with Dean-Stark apparatus and a condenser, under an inert atmosphere. 90 ml of DMF and 110 ml of toluene are added. The medium is heated to 140° C. under nitrogen and 80 ml of toluene are distilled off. The medium is then cooled to RT and then deoxygenated by sparging with nitrogen. 6 g of iodoanisole are then added, followed by heating at 155° C. for 20 hours. After cooling to RT, the medium is diluted with 200 ml of a water/ethyl ether mixture. The medium is then filtered through Celite®. The organic phase is washed 3 times with water, dried over MgSO$_4$ and then evaporated to give 4.3 g of a brown oil.

B) 1-(2-Methoxy-5-pentafluoroethylphenyl)ethanone 7.4 ml of BuLi at 2.5M in hexane are added, at –70° C., to a solution of 3.5 g of 1-methoxy-4-pentafluoroethylbenzene in 50 ml of anhydrous THF. The medium is stirred for 30 minutes at –70° C. and then for 45 minutes at 0° C. 15.5 ml of a 1M solution of zinc chloride in ether are then added. After stirring for 10 minutes at 0° C., 1.33 ml of acetyl chloride are added. The medium is then deoxygenated with nitrogen and 332 mg of benzyl(chloro)bis(triphenylphosphine)palladium in 5 ml of anhydrous THF are introduced. The medium is stirred for 2 hours 30 minutes at 0° C. and then for 72 hours at RT. The medium is poured onto 2.5M HCl solution and then extracted with ether. The organic phase is washed with 5% NaHCO$_3$ in water, with water and then with saturated NaCl solution. After drying over MgSO$_4$ and evaporation, the crude product is purifed by flash chromatography on silica to give 2.25 g of a white solid. m.p.=47° C.

C) 4-(2-Methoxy-5-pentafluoroethylphenyl)thiazol-2-ylamine 0.5 ml of bromine dissolved in 8 ml of methanol is added to a solution of 2.25 g of the product obtained from the preceding step in 10 ml of methanol. The medium is stirred for 10 minutes and then evaporated and taken up in dichloromethane. The organic phase is washed 3 times with water and then dried over MgSO$_4$. 2.63 g of the brominated product are recovered after evaporation. This compound is dissolved in 15 ml of methanol in the presence of 1.25 g of thiourea and the medium is refluxed for 2 hours. A solid precipitates during cooling to RT. The solid thus collected is rinsed with ethyl ether. The solid is suspended in a water/dichloromethane mixture and the base is restored by addition of sodium hydroxide. The aqueous phase is extracted twice with dichloromethane. The combined organic phases are dried over MgSO$_4$ and then evaporated to give 1.63 g of a yellow solid. m.p.=125° C.

By working according to the above procedures, the compounds of formula (III) described in the table below are prepared.

TABLE 1

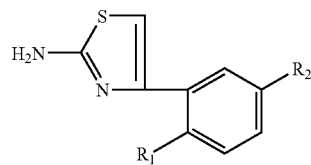

(III)

| Preparation No. | R₁ | R₂ | Salt | Characterization |
|---|---|---|---|---|
| 1.1 | -OMe | -OPr | — | m.p. = 76° C. |
| 1.2 | -OMe | -nBu | — | m.p. = 48° C. |
| 1.2a | -OMe | -nBu | HBr | m.p. = 186° C. |
| 1.3 | -OMe | cyclohexyl | — | m.p. = 113° C. |
| 1.4 | -OMe | -nPr | — | m.p. = 85° C. |
| 1.5 | -OEt | -Et | — | m.p. = 83° C. |
| 1.6 | -OMe | -Et | — | m.p. = 100° C. |
| 1.7 | -OEt | cyclohexyl | — | m.p. = 110° C. |
| 1.8 | -OMe | cyclopentyl | — | m.p. = 110° C. |
| 1.9 | -OEt | -nBu | — | m.p. = 65° C. |
| 1.10 | -OMe | CF₃ | — | m.p. = 144° C. |
| 1.11 | -OMe | -iPr | — | m.p. = 109° C. |
| 1.12 | -OMe | Me | — | m.p. = 121° C. |
| 1.13 | —O—CH₂-cyclopropyl | -nBu | — | m.p. = 59° C. |
| 1.14 | -OMe | —CH(CH₂—CH₃)(CH₂—CH₃) | — | m.p. = 91-93° C. |
| 1.15 | -OMe | Phenyl | — | m.p. = 116° C. |
| 1.16 | —Cl | CF₃ | — | m.p. = 110° C. |
| 1.17 | -OEt | Me | — | m.p. = 124° C. |
| 1.18 | —SO₂Et | -nBu | — | m.p. = 121° C. |
| 1.19 | -OMe | —CH(nPr)₂ | HCl | MH⁺ = 305.4 t = 7.61 |
| 1.20 | -OnPr | -nBu | — | m.p. = 63° C. |
| 1.21 | -OMe | -nHex | — | m.p. = 43° C. |
| 1.22 | -OMe | Adamantyl | — | m.p. = 81-82° C. |

TABLE 1-continued

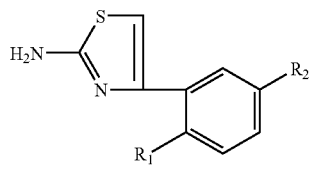

(III)

| Preparation No. | R₁ | R₂ | Salt | Characterization |
|---|---|---|---|---|
| 1.23 | -OEt | -nHex | — | m.p. = 75° C. |
| 1.24 | -OMe | CF₃CF₂ | — | m.p. = 125° C. |
| 1.25 | -OEt | CF₃CF₂ | — | MH⁺ = 338 T = 7.88 |
| 1.26 | -OEt | -nPr | — | m.p. = 87° C. |
| 1.27 | -OEt | cyclopentyl | — | m.p. = 128° C. |

Preparation 2.1

N-(Boc),N-(tetrahydro-2H-pyran-4-yl)piperidin-4-amine

A) 1-Benzyl-N-(tetrahydro-2H-pyran-4-yl)piperidin-4-amine (XXXXVI)

19 g of 4-amino-1-benzylpiperidine are placed in 50 ml of 1,2-dichloroethane under dry nitrogen and 10 g of tetrahydropyran-4-one in 20 ml of 1,2-dichloroethane are added; after stirring for 10 minutes, 29.6 g of NaBH(OAc)₃ are added and the mixture is then stirred for one day. 10% Na₂CO₃ solution and EtOAc are added to the reaction medium and the phases are then separated by settling. The organic phase is washed with 10% Na₂CO₃ solution and then with saturated NaCl solution, and then dried over MgSO₄ and evaporated under vacuum. 23.4 g of the expected compound are obtained. m.p.=60° C.

B) 1-Benzyl-N-Boc, —N-(tetrahydro-2H-pyran-4-yl)piperidin-4-amine 14.92 g of the compound obtained in the preceding step are placed in 100 ml of EtOAc, the solution is then cooled in an icebath and 12.46 g of (Boc)₂O in 30 ml of EtOAc are added. This mixture is heated at 50° C. for 4 days and then stirred for 2 days at room temperature. The reaction medium is washed with water (3 times), dried over MgSO₄ and then evaporated. The oil obtained crystallizes, and the solid is triturated from pentane, filtered off and dried at 60° C. over P₂O₅. 15.9 g of the expected compound are obtained, m.p.=104° C.

C) N-(Boc),N-(tetrahydro-2H-pyran-4-yl)piperidin-4-amine 15.8 g of the compound from the preceding step are placed in 100 ml of MeOH with 1 g of 10% palladium-on-charcoal, and the mixture is hydrogenated under atmospheric pressure at 30° C. for one day. The medium is filtered through Celite® and then rinsed with MeOH. After evaporating the filtrate, 11.15 g of the expected compound, which crystallizes, are obtained. m.p.=125° C.

Preparation of the Intermediates of Formula (II)

Preparation 3.1

4-(2,2-Diethoxyethoxy)benzoic acid (II): $R_3'$=4—$OCH_2CH(OEt)_2$

A) Methyl 4-(2,2-diethoxyethoxy)benzoate

A mixture containing 10 g of methyl 4-hydroxybenzoate and 22.71 g of $K_2CO_3$ in 100 ml of THF is heated at 100° C. for 5 min and cooled to room temperature, 15.54 g of 2-bromo-1,1-diethoxyethane are added and the mixture is stirred for 2 hours at room temperature and then for 32 hours at 100° C., and is allowed to return to room temperature. The inorganic material is filtered off and then rinsed with DMF. The filtrate is evaporated and then taken up in DCM, washed with water (3 times) and then with saturated NaCl solution, dried over $MgSO_4$ and evaporated. 16.68 g of the expected compound (greater than the theoretical mass) are obtained.

B) 4-(2,2-Diethoxyethoxy)benzoic acid 8.08 g of the ester obtained in the preceding step are placed in 50 ml of methanol with 16 ml of 5N NaOH and stirred for 6 hours. After evaporation of the solvent, the residue is taken up in water and 1.2M HCl is then added to pH=3; this mixture is filtered and rinsed with water to obtain a precipitate, which is dried under vacuum. The filtrate is extracted twice with DCM and then dried over $MgSO_4$. 7.29 g in total of the expected compound are obtained.

Preparation 3.2

4-((4-(N-Boc)tetrahydro-2H-pyran-4-yl)amino)piperidin-1-yl)carbonyl)benzoic acid, triethylamine salt

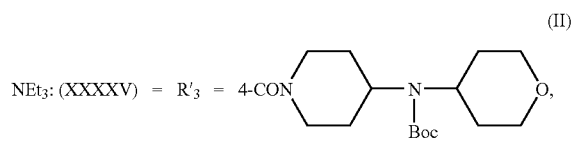

A) Methyl 4-((4-N-Bocamino)piperidin-1-ylcarbonyl)benzoate

A mixture containing 5.39 g of the monomethyl ester of terephthalic acid, 40 ml of $CH_3CN$, 6 ml of $Et_3N$, 14.8 g of BOP and 5 g of 4-(N-Bocamino)piperidine is stirred at room temperature for 4 days. The reaction medium is diluted with EtOAc and then washed 4 times with 10% $Na_2CO_3$ solution and then 4 times with water. The resulting solution is dried over $MgSO_4$ and then concentrated to dryness and then taken up in an $Et_2O$/cyclohexane mixture. The resulting solution is filtered and then dried to give 6.66 g of the expected compound. m.p.=128-130° C.

B) Methyl 4-((4-aminopiperidin-1-yl)carbonyl)benzoate hydrochloride 17.66 g of the compound from the preceding step are placed in 120 ml of a 4M solution of HCl in dioxane, with stirring at room temperature for 2 hours. Ether is added and the stirring is continued for a further one hour. The mixture is filtered, washed with ether and then dried to give 15 g of the expected compound. m.p.=236-238° C.

C) Methyl 4-((4-(tetrahydro-2H-pyran-4-ylamino) piperidin-1-yl)carbonyl)benzoate.

A mixture containing 15 g of the compound from the preceding step in 50 ml of DMF, 5 g of tetrahydro-4H-pyran-4-one and 4 ml of $Et_3N$ is stirred overnight. 1.36 ml of AcOH, 12.7 g of $NaBH(OAc)_3$ and 50 ml of DMF are added and stirring is continued for 3 hours. The reaction medium is concentrated to dryness and then taken up in DCM and washed with 10% $Na_2CO_3$ solution. The phases are separated by settling and the organic phase is then washed with water (3 times), dried over $MgSO_4$ and concentrated to dryness. 9.5 g of the expected compound are obtained in the form of a solid. m.p.=129° C.

D) Methyl 4-((4-((N-Boc)tetrahydro-2H-pyran-4-ylamino)piperidin-1-yl)carbonyl)benzoate A mixture containing 3.16 g of the compound from the preceding step in 12 ml of DCM is refluxed for 10 hours in the presence of 4.5 g of $Boc_2O$ and 1.65 ml of $Et_3N$. After cooling the reaction medium, it is washed with a buffer solution at pH=2 (3 times) and then with water (3 times). The organic phase is dried over $MgSO_4$ and then concentrated to dryness to give 4.63 g of the expected compound.

E) 4-((4-(N-Boc)tetrahydro-2H-pyran-4-yl)amino) piperidin-1-yl)carbonyl)benzoic acid, $Et_3N$ salt 4 g of the compound from the preceding step are stirred for 48 hours in 100 ml of 5N NaOH in methanol. The MeOH is removed by evaporation, the crude product is taken up in water and the aqueous phase is washed with DCM and then acidified with HCl to pH=3. The resulting phase is filtered and washed with ether, and the solid obtained is then taken up in DCM/water/$Et_3N$. The aqueous phase is extracted with DCM and then dried over $MgSO_4$ and concentrated to dryness to give 700 mg of the expected compound in solid form. $MH^+$=433.3; t=6.71.

The corresponding free acid is prepared: m.p.=190° C., $MH^+$=433.3; t=6.70.

Preparation 3.3

4-(4-((R)-3-(N-Boc)-pyrrolidin-1-yl)piperidine-1-carbonyl)benzoic acid

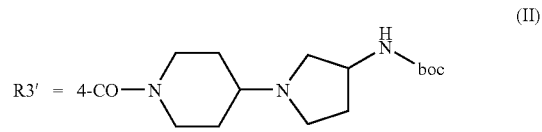

A) tert-butyl (1-(benzylpiperidin-4-yl)pyrrolidin-3-yl)carbamate 4.66 g of 1-benzyl-4-piperidone in 6 ml of dichloroethane are added to a solution of 4.6 g of (3R)-(3-tert-butoxycarbonylamino)pyrrolidine in 5 ml of dichloroethane. After 20 minutes at RT, 7.31 g of NaBH(OAc)$_3$ are added, while keeping the medium at a temperature below 20° C., followed by addition of 20 ml of dichloroethane to dissolve the medium, which sets to a solid. The medium is stirred at RT for 24 hours, hydrolyzed by addition of aqueous 10% Na$_2$CO$_3$ solution and diluted with ethyl acetate. After separation of the phases by settling, the organic phase is washed with aqueous 10% Na$_2$CO$_3$ solution, then with saturated NaCl solution and then dried over MgSO$_4$ and evaporated. The crude product is triturated from ether, filtered, rinsed with ether and then dried to give 7.38 g of a white solid.

m.p.=118° C.

B) (tert-Butyl 1-piperidin-4-ylpyrrolidin-3-yl)carbamate

A solution of 7.37 g of the compound described above in 50 ml of methanol is hydrogenated at atmospheric pressure and at RT in the presence of 1 g of 10% Pd/C for 12 hours. The medium is filtered through Celite® and the solid is rinsed with methanol. After evaporating off the filtrate, 5.2 g of an oil which solidifies after trituration are obtained, and is used without further purification for the following step.

C) Methyl 4-(4-((R)-3-(N-Boc)pyrrolidin-1-yl)piperidin-1-carbonyl)benzoate 3.8 g of terephthalic acid monomethyl ester are added to a solution of 4.75 g of the compound obtained in the preceding step in 35 ml of acetonitrile, followed by addition of 9.4 g of BOP and then 2.2 g of triethylamine. The medium is stirred at RT for 24 hours and then concentrated. The crude product is taken up in ethyl acetate, washed twice with water and then twice with aqueous 10% Na$_2$CO$_3$ solution, and then with saturated NaCl solution. After drying the organic phase over MgSO$_4$ and evaporation, 8.62 g of crude product are recovered and are triturated from an ether/ethyl acetate mixture. After filtration, 5.28 g of the expected product are collected.

D) 4-(4-((R)-3-(N-Boc)pyrrolidin-1-yl)piperidine-1-carbonyl)benzoic acid 1.17 g of sodium hydroxide are added to a solution of 5.05 g of the ester obtained in the preceding step in 20 ml of methanol. The medium is stirred at RT for 12 hours and then evaporated and taken up in water. The aqueous phase is washed with ether and then acidified to pH=5 and extracted twice with ethyl acetate. The organic phase is dried over MgSO$_4$ and then concentrated. The aqueous phase is evaporated and then dried by azeotropic distillation with ethanol. The residue is taken up in ethanol and filtered through Celite®, and the filtrate is evaporated. The two crude products are combined to give 3.65 g of the expected acid.

MH$^+$=418 at t=4.7 minutes

Preparation of the Intermediates of Formula (IV)

Preparation 4.1.1

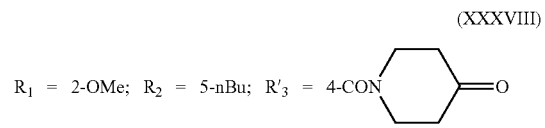

(XXXVIII)

R$_1$ = 2-OMe; R$_2$ = 5-nBu; R'$_3$ = 4-CON

N-(4-(5-Butyl-2-methoxyphenyl)-1,3-thiazol-2-yl)-4-((4-oxopiperidin-1-yl)carbonyl)benzamide A suspension containing 0.86 g of the aminothiazole from Preparation 1.2, 1 g of 4-((4-oxopiperidin-1-yl)carbonyl)benzoic acid and 0.6 ml of Et$_3$N in 8 ml of acetonitrile is stirred at RT for 3 days and 1.9 g of BOP are added. The precipitate formed is filtered off and then washed with 0.3 ml of CH$_3$CN and then with 1 ml of ether, to give 0.85 g of the expected compound.

m.p.=184° C.

Compound (XXXVIII) may also be prepared according to the following method.

4.7 g of 4-piperidone hydrochloride monohydrate are added to a solution of 10.4 g of the acid prepared via the method described in 4.2.1 in 50 ml of acetonitrile, followed by addition of 15.7 g of BOP. At 0° C., 13.3 ml of DIPEA are added and the temperature is allowed to return to RT. After stirring for 24 hours at RT, the reaction medium is filtered, the solid is rinsed with acetonitrile and the filtrate is then concentrated and taken up in dichloromethane. The organic phase is washed with 10% Na$_2$CO$_3$, then with 0.5M HCl and then with saturated NaCl solution. After drying the organic phase over MgSO$_4$, 11.33 g of the expected product are recovered.

By working in a similar manner, the compounds described in the table below were prepared.

TABLE 2

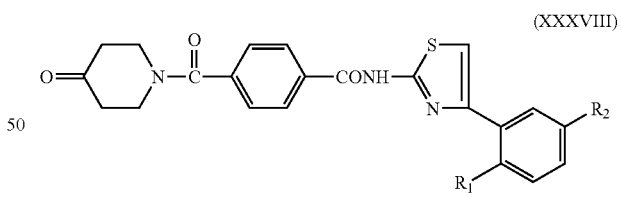

(XXXVIII)

| Preparation | R$_1$ | R$_2$ | Characterization |
|---|---|---|---|
| 4.1.1 | MeO | nBu | m.p. = 184° C. |
| 4.1.2 (compound 242) | MeO | nPrO | m.p. = 196° C. |
| 4.1.3 | MeO | Me | m.p. = 183° C. |
| 4.1.4 | MeO | Et | m.p. = 180° C. |
| 4.1.5 | MeO | nPr | m.p. = 172° C. |
| 4.1.6 (compound 243) | MeO | Cyclohexyl | m.p. = 186° C. dec. |
| 4.1.7 (compound 244) | EtO | Cyclohexyl | m.p. = 236° C. |
| 4.1.8 | EtO | Et | m.p. = 160° C. |
| 4.1.9 | MeO | Cyclopentyl | MH$^+$ = 504.5 t = 10.55 |
| 4.1.10 | -OEt | -nBu | MH$^+$ = 506 t = 10.3 |

Preparation 4.2.1

4-(((4-(5-Butyl-2-methoxyphenyl)-1,3-thiazol-2-yl)amino)carbonyl)benzoic acid (XXXIIIa): $R_1$=2-OMe; $R_2$=5-nBu; $R'_3$=4-COOH 5 g of aminothiazole from Preparation 1.2, 4.12 g of methyl 4-carboxybenzoate and then 1.85 ml of $Et_3N$, 25 ml of $CH_3CN$ and 10.13 g of BOP are mixed together and stirred for 4 days at room temperature. The precipitate formed is filtered off and then washed with acetonitrile. The precipitate is then taken up in a mixture of EtOAc and saturated $Na_2CO_3$ solution. After separation of the phases by settling, the aqueous phase is extracted with DCM. The combined organic phases are dried over $MgSO_4$ and concentrated. 3.18 g of the expected compound are obtained in the form of a methyl ester. This ester is suspended in 34 ml of MeOH and 5.3 ml of 5N sodium hydroxide are then added. After stirring for 5 days at room temperature, the reaction medium is concentrated to dryness. The solid obtained is dissolved in 5 ml of water and then washed twice with 50 ml of EtOAc. The aqueous phase is acidified with 1M HCl to pH=2 and the precipitate formed is filtered off and then washed with ether. After drying, 2.78 g of the expected compound are obtained in the form of a gum. m.p.=160° C.

By working as described for the above preparation, the intermediate compounds described in the table below were prepared.

TABLE 3

(XXXIII) and (XXXIIIa)

$RO_2C$—⟨phenyl⟩—CONH—⟨thiazole⟩—⟨phenyl with $R_1$, $R_2$⟩

| Preparation | $R_1$ | $R_2$ | R | Salt | Characterization |
|---|---|---|---|---|---|
| 4.2.1 | MeO- | nBu | H | — | $MH^+$ = 410<br>t = 21.53 |
| 4.2.2 | MeO- | nPrO | Me | — | m.p. = 180° C. |
| 4.2.3 | MeO- | nPrO | H | HCl | $MH^+$ = 412<br>t = 6.11 |
| 4.2.4 | MeO- | nBu | Me | — | $MH^+$ = 424<br>t = 21.35 |
| 4.2.5 | MeO- | nPr | Me | — | — |
| 4.2.6 | MeO- | nPr | H | — | $MH^+$ = 396<br>t = 8.17 |
| 4.2.7 | EtO- | Et | H | TFA | $MH^+$ = 396<br>t = 14.45<br>m.p. = 250° C. |
| 4.2.8 | EtO- | Et | tBu | — | NMR |
| 4.2.9 | MeO- | Cyclohexyl | Me | — | $MH^+$ = 440<br>t = 8.11 |
| 4.2.10 | MeO- | Cyclohexyl | H | — | $MH^+$ = 436<br>t = 10.49<br>m.p. > 260° C. |
| 4.2.11 | EtO- | Cyclohexyl | Me | — | — |
| 4.2.12 | EtO- | Cyclohexyl | H | — | $MH^+$ = 450<br>t = 11.05 |
| 4.2.13 | MeO- | Et | Me | — | NMR |
| 4.2.14 | MeO- | Et | H | — | NMR |
| 4.2.15 | MeO- | nHex | Me | — | $MH^+$ = 453<br>t = 11.9 |
| 4.2.16 | MeO- | nHex | H | — | $MH^+$ = 439<br>t = 11.0 |
| 4.2.17 | EtO- | nBu | Me | — | $MH^+$ = 439<br>t = 12.1 |
| 4.2.18 | EtO- | nBu | H | — | $MH^+$ = 425<br>t = 8.6 |

NMR: Preparation 4.2.8.: 1.2 ppm:t:3H, 1.6 ppm:t:3H; 1.7 ppm:s:9H, 2.7 ppm:m:2H, 4.2 ppm:q:2H, 7.0-7.2 ppm:m:2H; 7.8 ppm:s:1H; 8.0-8.3 ppm:m:5H, 12.9 ppm:bs:1H.

NMR: Preparation 4.2.13.: 1.2 ppm:t:3H, 2.6 ppm:q:2H; 3.9 ppm:s:6H, 7.0-7.2 ppm:m:2H, 7.7 ppm:s:1H; 8.0-8.4 ppm:m:5H; 12.8 ppm:bs:1H.

NMR: Preparation 4.2.14.: 1.2 ppm:t:3H, 2.7 ppm:q:2H; 3.9 ppm:s:3H, 7.0-7.2 ppm:m:2H, 7.7 ppm:s:1H; 8.0-8.4 ppm:m:5H; 12.6-13 ppm:bs:1H; 13.2-13.5 ppm:bs:1H.

Preparation 4.3.1

N-(4-(5-Butyl-2-methoxyphenyl)-1,3-thiazol-2-yl)-4-(2-chloroethyl)benzamide.

(XXIX): $R_1$=2-OMe; $R_2$=5-nBu; $R'_3$=4-$(CH_2)_2$Cl

A mixture containing 3 g of aminothiazole from Preparation 1.2, 10 ml of $CH_3CN$, 2.54 g of 4-(2-chloro-ethyl)benzoic acid, 1.11 ml of $Et_3N$ and 6.1 g of BOP is prepared and stirred for 48 hours. The reaction medium is diluted with EtOAc and then washed with saturated $Na_2CO_3$ solution (twice) and with saturated NaCl solution, and then dried over $MgSO_4$ and concentrated to dryness. After trituration from EtOH, the insoluble material formed is removed by filtration and the filtrate is then concentrated to dryness to give 7.7 g of the expected compound. This compound is purified by chromatography on silica, eluting with a toluene/cyclohexane gradient (9/1; v/v) up to pure toluene.

By working as described above, the compounds of formula (XXIX) described in the table below are prepared.

TABLE 4

(XXIX)

$Cl(CH_2)_n$—⟨phenyl⟩—CONH—⟨thiazole⟩—⟨phenyl with $R_1$, $R_2$⟩

| Preparation | n | $R_1$ | $R_2$ | Characterization |
|---|---|---|---|---|
| 4.3.1 | 2 | MeO- | nBu | NMR |
| 4.3.2 | 2 | MeO- | Et | NMR |
| 4.3.3 | 2 | MeO- | nPrO | $MH^+$ = 431.2<br>t = 9.91 |
| 4.3.4 | 1 | MeO- | nBu | — |
| 4.3.5 | 1 | MeO- | Et | m.p. = 141° C. |

NMR: Preparation 4.3.1.: 0.85 ppm:t:3H, 1.05-1.6 ppm:m: 4H, 2.5-2.6 ppm:m:2H, 3.0 ppm:m:2H, 3.8-4.0 ppm:m:5H; 7.0 ppm:m:2H, 7.4-7.6 ppm:d:2H, 7.7 ppm:s:1H; 8.0 ppm: m:3H; 12.6 ppm:bs:1H.

NMR: Preparation 4.3.2.: 1.2 ppm:t:3H, 2.7 ppm:q:2H; 3.2 ppm:t:2H, 4.0 ppm:m:5H, 7.0-7.2 ppm:m:2H, 7.6 ppm:d:2H; 7.8 ppm:s:1H; 8.0-8.3 ppm:m:3H, 12.7 ppm:bs:1H.

Preparation 4.4.1

N-(4-(5-Butyl-2-methoxyphenyl)-1,3-thiazol-2-yl)-4-(3-oxopropyl)benzamide $R_1$=2-OMe; $R_2$=5-nBu; $R'_3$=4-(CH$_2$)$_2$CHO A) N-(-4-(5-Butyl-2-methoxyphenyl)-1,3-thiazol-2-yl)-4-iodobenzamide A mixture containing 6.62 g of aminothiazole from Preparation 1.2, 75 ml of CH$_3$CN, 7.53 g of 4-iodobenzoic acid, 4.2 ml of Et$_3$N and 13.45 g of BOP is stirred at room temperature for 8 hours. The product formed is filtered off and then rinsed with CH$_3$CN. The precipitate is redissolved in DCM, washed with 7% NaOH solution (twice) and then dried over MgSO$_4$ and evaporated. In parallel, the filtrate in CH$_3$CN is evaporated, taken up in DCM and then washed 4 times with 7% NaOH solution and dried over MgSO$_4$. A total of 16.81 g of expected compound are thus obtained. MH$^+$=492; t=12.01 minutes.

B) N-(4-(5-Butyl-2-methoxyphenyl)-1,3-thiazol-2-yl)-4-(3-oxopropyl)benzamide 2 g of the compound from the preceding step are placed in 15 ml of DMF with 0.79 g of 4 Å molecular sieves, 0.42 ml of allyl alcohol, 1.31 g of dried tetra(n-butyl)ammonium bromide and 0.85 g of dried NaHCO$_3$. After stirring for 2 hours at room temperature, 50 mg of Pd(OAc)$_2$ are added and stirring is continued at room temperature for 20 hours, under dry nitrogen. The resulting mixture is filtered through Celite® and rinsed with DMF, and then water and ether are added. After separation of the phases by settling, the aqueous phase is extracted a further 3 times with ether. The combined organic phases are dried over MgSO$_4$ and evaporated under vacuum. 2 g of the expected compound are obtained.

By working as described above, the compounds of formula (XXVII) and the iodo precursors thereof as described in step A of the above preparation are prepared.

TABLE 5

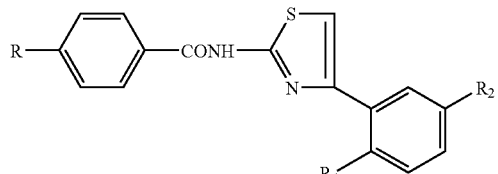

(XXVII): R = (CH$_2$)$_2$CHO
(XXVIIa): R = I

| Preparation No. | $R_1$ | $R_2$ | R | Characterization |
|---|---|---|---|---|
|  | OMe | nBu | I | MH$^+$ = 493.2 t = 12.01 |
| 4.4.1 | OMe | nBu | —(CH$_2$)$_2$CHO | — |
|  | OEt | Et | I | m.p. = 180° C. |

TABLE 5-continued

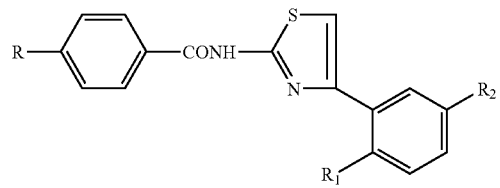

(XXVII): R = (CH$_2$)$_2$CHO
(XXVIIa): R = I

| Preparation No. | $R_1$ | $R_2$ | R | Characterization |
|---|---|---|---|---|
| 4.4.2 | OEt | Et | —(CH$_2$)$_2$CHO | — |
|  | OMe | Et | I | MH$^+$ = 465.1 t = 11.35 |
| 4.4.3 | OMe | Et | —(CH$_2$)$_2$CHO | — |

Preparation 4.5

N-(4-(2-Methoxy-5-propoxyphenyl)-1,3-thiazol-2-yl)-N'-(2-oxoethyl)terephthalamide hydrochloride (XXXIVa), HCl: $R_1$=2-OMe; $R_2$=5-OnPr; $R'_3$=4-CONHCH$_2$CHO A) N-(2,2-Dimethoxyethyl)-N'-(4-(2-methoxy-5-propoxyphenyl)-1,3-thiazol-2-yl)terephthalamide A mixture containing 2.6 g of the compound from Preparation 4.2.3, 30 ml of CH$_3$CN, 1.61 ml of Et$_3$N, 0.53 ml of aminoacetaldehyde dimethyl acetal and 2.56 g of BOP is stirred at room temperature for three and a half hours. After filtration, the filtercake is washed with CH$_3$CN and then with DCM. The filtrate is evaporated and the residue is triturated with CH$_3$CN and filtered to give 2 g of the expected compound.

B) N-(4-(2-Methoxy-5-propoxyphenyl)-1,3-thiazol-2-yl)-N'-(2-oxoethyl)terephthalamide hydrochloride 0.2 g of the compound obtained in the preceding step are placed in 2 ml of dioxane under dry nitrogen, the mixture is heated to reflux for dissolution and cooled to RT, followed by addition of 3 ml of 4M HCl in dioxane, and this mixture is stirred for 7 hours. The precipitate formed is filtered off under nitrogen to give 0.15 g of the expected compound.

Preparation 4.6

4-(2-Hydroxyethoxy)-N-(4-(2-methoxy-5-propoxyphenyl)-1,3-thiazol-2-yl)benzamide (XVIII): $R_1$=2-OMe; $R_2$=5-OnPr; $R'_3$=4-O(CH$_2$)$_2$OH.

A) Methyl 4-(2-(tetrahydro-2H-pyran-2-yloxy)ethoxy)benzoate.

A mixture containing 40 g of methyl 4-hydroxybenzoate and 90.84 g of K$_2$CO$_3$ in 400 ml of DMF is heated to 100° C.

and 71.47 g of 2-(2-bromoethoxy)tetrahydro-2H-pyran are added slowly, with continued heating for 8 hours. The inorganic material is filtered off and rinsed with DMF. The filtrate is evaporated under vacuum and then taken up in DCM, washed 3 times with water, dried over $MgSO_4$ and then evaporated. 77.66 g of the expected compound are obtained.

B) 4-(2-(Tetrahydro-2H-pyran-2-yloxy)ethoxy)benzoic acid

A mixture containing 77.66 g of the product from the preceding step in 400 ml of MeOH and 135 ml of 5M NaOH is stirred at RT, under dry nitrogen, for one day. The reaction medium is evaporated and then taken up in water and acidified to pH=5 by addition of HCl. The resulting mixture is filtered and then rinsed with water. The filtrate is extracted twice with DCM and then dried over $MgSO_4$ and evaporated. 72 g of the expected compound are obtained.

C) N-(4-(2-Methoxy-5-propoxyphenyl)-1,3-thiazol-2-yl)-4-(tetrahydro-2H-pyran-2-yloxy)ethoxy)benzamide (XVII): $R'_3$=4-$O(CH_2)_2$—OTHP.

A mixture containing 3.83 g of the compound from Preparation 1.1, 30 ml of $CH_3CN$, 4.63 g of acid obtained from the preceding step, 7.69 g of BOP and 2.4 ml of $Et_3N$ is stirred at RT for 4 days. The precipitate formed is filtered off, rinsed with $CH_3CN$ and dried over $P_2O_5$ at 60° C. 5.5 g of the expected compound are obtained, m.p.=114° C.

D) 4-(2-Hydroxyethoxy)-N-(4-(2-methoxy-5-propoxyphenyl)-1,3-thiazol-2-yl)benzamide 5.41 g of the compound from the preceding step are placed in 25 ml of 4M HCl in dioxane and are stirred for 30 minutes. The precipitate formed is filtered off and then rinsed with dioxane and with ether and dried over $P_2O_5$ at 60° C. 4.6 g of the expected compound are obtained.

Preparation 4.7

N-(4-(2-Methoxy-5-propoxyphenyl)-1,3-thiazol-2-yl)-4-(2-oxoethoxy)benzamide (XIV): $R_1$=OMe; $R_2$=OnPr; $R'_3$=4-$OCH_2CHO$.

A) 4-(2,2-Diethoxyethoxy)-N-(4-(2-methoxy-5-propoxyphenyl)-1,3-thiazol-2-yl)benzamide A mixture containing 4.56 g of the compound from Preparation 1.1 and 5.26 g of the benzoic acid derivative from Preparation 3.1 in 40 ml of $CH_3CN$ is stirred for 3 days with 9.16 g of BOP and 2.9 ml of $Et_3N$. After evaporation, the residue is taken up in DCM and then washed 3 times with water, dried over $MgSO_4$ and evaporated. The product obtained is chromatographed on silica, eluting with a toluene/EtOAc mixture (95/5; v/v). The product is taken up in ether, filtered off, rinsed and then dried at 60° C. over $P_2O_5$ to give 6.12 g of the expected compound. m.p.=107° C.

B) N-(4-(2-Methoxy-5-propoxyphenyl)-1,3-thiazol-2-yl)-4-(2-oxoethoxy)benzamide 1.52 g of the compound from the preceding step are placed in 3.8 ml of formic acid and heated at 50° C. for 3 hours. After cooling to room temperature, water is added and the mixture is then filtered, rinsed with water and dried at 60° C. over $P_2O_5$. 1.25 g of the expected compound are obtained.

Preparation 4.7a

N-(4-(2-Methoxy-5-propoxyphenyl)-1,3-thiazol-2-yl)-4-(2-oxoethoxy)benzamide

A mixture containing 0.4 g of the compound from Preparation 4.6 in 0.36 ml of DMSO and 5 ml of DCM is cooled to −60° C. under dry nitrogen and stirred for 2 hours. 0.83 ml of $Et_3N$ is added and the temperature is allowed to return to RT. The inorganic material is filtered off and then rinsed with DCM. The filtrate is washed with water, with 10% $Na_2CO_3$ solution and then twice with saturated NaCl solution. The resulting solution is dried over $MgSO_4$ and evaporated. 0.39 g of the expected compound is obtained.

Preparation 4.8

2-(4-(((4-(2-Methoxy-5-propoxyphenyl)-1,3-thiazol-2-yl)amino)carbonyl)phenoxy)ethylmethanesulphonate.

A mixture containing 0.4 g of the compound from Preparation 4.6 in 5 ml of DCM, 0.28 ml of $Et_3N$ and 120 μl of $CH_3SO_2Cl$ is prepared. This mixture is stirred for one and a half hours while cooling in an ice bath. The insoluble material is filtered off and rinsed with DCM. The filtrate is washed 3 times with water. The organic phase is dried over $MgSO_4$, filtered, rinsed with DCM and evaporated to give 0.38 g of the expected compound.

EXAMPLE 1

Compound 65

N-[4-(5-Butyl-2-methoxyphenyl)-1,3-thiazol-2-yl]-4((4-[2-(S)-(hydroxymethyl)pyrrolidin-1-yl]piperidin-1-yl)carbonyl)benzamide

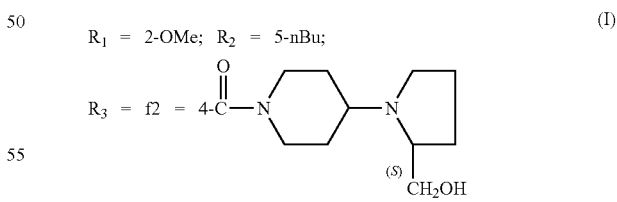

A solution containing 82 mg of the compound of Preparation 4.1.1 and 45 mg of (S)-prolinol in 2 ml of DCM and 5 drops of $CH_3CO_2H$ is stirred for 30 minutes, 100 mg of $NaBH(OAc)_3$ are then added and the mixture is stirred for 12 hours. The medium is diluted with 200 ml of EtOAc and then washed twice with $Na_2CO_3$, dried over $MgSO_4$ and evaporated. The product obtained is ultrasonicated in the presence of 5 ml of ether and then filtered to give 70 mg of the expected compound. m.p.=199° C.

NMR spectrum: 0.85 ppm:t:3H, 1.1-2 ppm:m:12H, 2.2-4.6 ppm:m:15H, 6.8-7.2 ppm:dd:2H, 7.45 ppm:d:2H, 7.65 ppm: s:1H; 7.95 ppm:s:1H; 8.1 ppm:d:2H, 12.6 ppm:bs:1H.

EXAMPLE 2

Compound 120

4-((4-[3-(R)-(Acetylamino)pyrrolidin-1-yl]piperidin-1-yl)carbonyl)-N-[4-(5-butyl-2-methoxyphenyl)-1,3-thiazol-2-yl]benzamide $R_1$ = 2-OMe; $R_2$ = 5-nBu;  (I)

$R_3$ = f2 = 4-CON

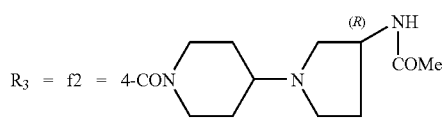

A mixture containing 0.25 g of the compound of Preparation 4.1.1, 0.13 g of (3R)-3-acetamidopyrrolidine and 2 ml of DCM is placed under dry nitrogen and stirred for 15 minutes, followed by addition of 0.22 g of NaBH(OAc)$_3$ and 8 drops of AcOH, and stirring is continued at room temperature for 3 hours 50 minutes. 10% Na$_2$CO$_3$ solution and EtOAc are added. After separation of the phases by settling, the organic phase is washed with 10% Na$_2$CO$_3$ and then dried over MgSO$_4$ and then evaporated. The residue is triturated in ether and then filtered, rinsed with ether and dried at 60° C. over P$_2$O$_5$. 0.25 g of the expected compound is obtained. m.p.>200° C. dec.

NMR spectrum: 0.85 ppm:t:3H; 1-2.1 ppm:m:13H, 2.1-4.5 ppm:m:15H, 6.8-7.2 ppm:dd:1H; 7.45 ppm:d:2H, 7.65 ppm: s:1H; 7.85 ppm:d:1H; 8.15 ppm:d:2H, 12.65 ppm:bs:1H.

EXAMPLE 3

Compound 107

N-[4-(5-Butyl-2-methoxyphenyl)-1,3-thiazol-2-yl]-4-((4-pyrrolidin-1-ylpiperidin-1-yl)carbonyl)benzamide dihydrochloride 2HCl: $R_1$ = 2-OMe; $R_2$ = 5-nBu;  (I)

$R_3$ = f2 = 4-CON

A mixture containing 0.6 g of the compound of Preparation 4.2.1, 6 ml of CH$_3$CN, 0.31 ml of ethyldiiso-propylamine, 0.27 g of 4-(pyrrolidin-1-yl)piperidine in 2 ml of CH$_3$CN and 0.78 g of BOP is stirred at room temperature for 9 days. After evaporating off the solvents, the medium is taken up in EtOAc and then washed with aqueous 10% Na$_2$CO$_3$ solution (3 times), then with saturated NaCl solution and then dried over MgSO$_4$ and evaporated under vacuum. The residue is chromatographed on silica, eluting with DCM/MeOH (100/3; v/v) to give 0.43 g of base, m.p.=128° C., MH$^+$=547.4; t=6.83.

The base obtained is taken up in DCM, followed by addition of hydrochloric ether. 0.44 g of the expected compound is obtained after filtration and drying.

NMR spectrum: 0.85 ppm:t:3H, 1.05-2 ppm:m:12H, 2.25 ppm:m:1H; 2.5 ppm:t:2H, 2.8-4.40 ppm:m:12H, 6.95 ppm: d:1H; 7.05 ppm:dd:1H; 7.5 ppm:d:2H, 7.65 ppm:s:1H; 7.95 ppm:d:1H; 8.15 ppm:d:1H; 12.55 ppm:bs:1H.

EXAMPLE 4

Compound 68

N-[4-(5-Butyl-2-methoxyphenyl)-1,3-thiazol-2-yl]-4-((4-(tetrahydro-2H-pyran-4-ylamino)piperidin-1-yl)carbonyl)benzamide dihydrochloride

A)

2HCl: $R_1$ = 2-OMe; $R_2$ = 5-nBu;  (I)

$R_3$ = f2 = 4-CON

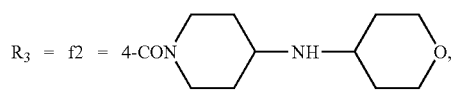

$R_1$ = 2-OMe; $R_2$ = 5-nBu;  (IV)

$R'_3$ = 4-CON

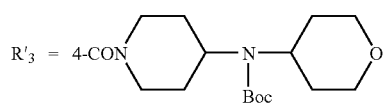

0.3 g of the compound of Preparation 4.2.1 is placed in 3 ml of CH$_3$CN, and 153 μl of ethyldiisopropylamine, 0.25 g of amine from Preparation 2.1 and 0.39 g of BOP are added. The mixture is stirred at room temperature overnight and then filtered, rinsed with ether and dried over P$_2$O$_5$ at 60° C. 0.36 g of the expected compound is obtained. m.p.=152° C.

B)

0.35 g of the compound from the preceding step is placed in 3 ml of 4M HCl in dioxane and stirred for 35 minutes at room temperature. Ether is added and the mixture is filtered, washed with ether and then dried over P$_2$O$_5$ at 60° C. 0.32 g of the expected compound is obtained. m.p.=181° C.

NMR spectrum: 0.85 ppm:t:3H, 1.25 ppm:sext:2H, 1.15-1.90 ppm:m:10H, 2.5 ppm:t:2H, 2.65-4.70 ppm:m:15H, 6.95 ppm:d:1H; 7.05 ppm:dd:1H; 7.45 ppm:d:2H, 7.65 ppm:s:1H; 7.95 ppm:d:1H; 8.1 ppm:d:2H, 9.3 ppm:bs:1H; 12.65 ppm: bs:1H.

Starting with the intermediate compounds described in the table below, the process is performed according to Example 4, step B by treatment in acidic medium, to prepare compounds of formula (I) according to the invention.

TABLE 6

(IV)

[Structure: R'₃-C₆H₄-CONH-thiazole(S,N)-C₆H₃(R₂)(OMe)]

| Preparation | R₂ | R'₃ | Characterization |
|---|---|---|---|
| 5.1 | -nBu | 4-(N-Boc-tetrahydropyran-4-yl-amino)piperidin-1-yl-CO— | m.p. = 152° C. |
| 5.2 | -Et | Boc-NH—(CH₂)₂—NHCO— | m.p. = 221° C. |
| 5.3 | -OnPr | (R)-1-Boc-pyrrolidin-3-yl-NHCO— | MH⁺ = 581.4<br>t = 10.12 |
| 5.4 | -OnPr | (R,S)-3-(Boc-NH)-pyrrolidin-1-yl-CO— | MH⁺ = 581.4<br>t = 9.74 |
| 5.5 | -nBu | (R,S)-1-Boc-3-methoxy-piperidine | MH⁺ = 566.4<br>t = 12.11 |
| 5.6 | -nBu | (S)-1-Boc-3-methoxy-pyrrolidine | MH⁺ = 552.5<br>t = 11.84 |
| 5.7 | -nBu | (S)-1-Boc-2-(methoxymethyl)-pyrrolidine | MH⁺ = 566.5<br>t = 12.37 |
| 5.8 | -nBu | (1S,4S)-5-Boc-2,5-diazabicyclo[2.2.1]heptane-2-carbonyl | MH⁺ = 591.4<br>t = 10.63<br>m.p. = 115° C. |
| 5.9 | -nBu | (R,S)-1-Boc-2-(acetamidomethyl)-pyrrolidine | m.p. = 98° C. |
| 5.10 | Cyclopentyl | 4-(N-Boc-tetrahydropyran-4-yl-amino)piperidin-1-yl-CO— | m.p. = 180° C. |

TABLE 6-continued (IV)

| Preparation | R₂ | R'₃ | Characterization |
|---|---|---|---|
| 5.11 | -nBu | Boc-N—⟨piperidine⟩— | m.p. = 82° C. |
| 5.12 | -nPr | ⟨tetrahydropyran⟩—N(Boc)—(CH₂)₂—O— | MH⁺ = 596.3<br>t = 10.74 |
| 5.13 | -nBu | —CONH—⟨pyrrolidine⟩—N-Boc (R) | MH⁺ = 579<br>t = 10.6 |
| 5.14 | -nBu | —CONH—⟨pyrrolidine⟩—N-Boc (S) | MH⁺ = 579<br>t = 10.6 |

EXAMPLE 4a

Compound 68

N-[4-(5-Butyl-2-methoxyphenyl)-1,3-thiazol-2-yl]-4-((4-(tetrahydro-2H-pyran-4-ylamino)piperidin-1-yl)carbonyl)benzamide dihydrochloride 2HCl: $R_1$ = 2-OMe; $R_2$ = 5-nBu; (I)

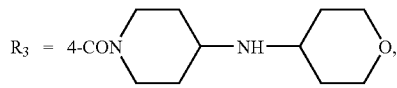

$R_3$ = 4-CON⟨piperidine⟩—NH—⟨tetrahydropyran⟩O,

A)

A mixture containing 370 mg of the compound from Preparation 1.2, 3 ml of CH₃CN, 378 mg of BOP and 151 mg of the compound from Preparation 3.2 is stirred at room temperature for 48 hours. The reaction medium is diluted with EtOAc and then washed 3 times with aqueous 10% Na₂CO₃ solution and then 3 times with aqueous NaCl solution. The organic phase is dried over MgSO₄ and then concentrated to dryness. The residue is taken up in isopropyl ether and then filtered and dried to give 325 mg of the expected compound. m.p.=152° C.

B)

320 mg of the compound from the preceding step in 3 ml of 4M HCl in dioxane are stirred for one hour. Ether is added, the mixture is filtered and the solid is then washed with ether and dried to give 259 mg of the expected compound. m.p.=181° C.

EXAMPLE 5

Compound 161

4-[3-(3-(Acetylamino)pyrrolidin-1-yl)propanoyl]-N-[4-(5-butyl-2-methoxyphenyl)-1,3-thiazol-2-yl]benzamide.

$R_1$ = 2-OCH₃; $R_2$ = 5-nBu; (I)

$R_3$ = b = 4-(CH₂)₂—N⟨pyrrolidine-NHCOMe⟩ (R,S)

A mixture containing 0.3 g of the compound from Preparation 4.3.1, 0.12 g of KI, 0.06 g of NaHCO₃ in 3 ml of DMF and 897.3 mg of pyrrolidine-3-acetamide is stirred at 50° C. for 2 days. The medium is concentrated to dryness and then taken up in DCM. The organic phase is washed twice with saturated NaCl solution and then dried over MgSO₄ and concentrated to dryness. The product crystallizes out in the presence of MTBE. After filtration and drying, 0.02 g of the expected compound is obtained, m.p.=112° C.

EXAMPLE 6

Compound 185

N-[4-(5-Ethyl-2-methoxyphenyl)-1,3-thiazol-2-yl]-4-[N-((1-ethylpyrrolidin-2-yl)methyl)glycyl]benzamide trihydrochloride 3HCl: $R_1$ = 2-OMe; $R_2$ = 5-Et;   (I)

$R_3$ = d2 = 4-CH$_2$NHCH$_2$— 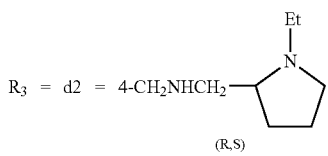
(R,S)

A mixture containing 0.25 g of the compound from Preparation 4.3.5 in 3 ml of CH$_3$CN and 0.21 g of 2-aminomethyl-1-ethylpyrrolidine in 1 ml of CH$_3$CN is refluxed for five and a half hours. After stirring overnight at room temperature, the mixture is evaporated and the residue is taken up in DCM and then washed 3 times with water, dried over MgSO$_4$ and evaporated. The product obtained is chromatographed on silica, eluting with DCM/MeOH (100/5; v/v).

The compound obtained is taken up in DCM, hydrochloric ether is added and the precipitate formed is then filtered off and rinsed with ether. It is dried over P$_2$O$_5$ at 60° C. to give 0.17 g of the expected compound, m.p.=163° C. (dec).

EXAMPLE 7

Compound 182

N-[4-(5-Butyl-2-methoxyphenyl)-1,3-thiazol-2-yl]-4-[3-(tetrahydro-2H-pyran-4-ylamino)propyl]benzamide $R_1$ = 2-OMe; $R_2$ = 5-nBu;   (I)

$R_3$ = b = 4-(CH$_2$)$_3$—NH— 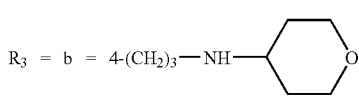

A mixture containing 0.38 g of the compound from Preparation 4.4.1 in 3 ml of DCM and 0.15 g of 4-aminotetrahydropyran in 1 ml of DCM is placed under nitrogen. After stirring for 15 minutes, 0.31 g of NaBH(OAc)$_3$ is added and stirring is continued for 6 hours. 10% Na$_2$CO$_3$ solution and EtOAc are added, the phases are then separated by settling and the organic phase is washed with 10% Na$_2$CO$_3$ solution and then dried over Na$_2$SO$_4$ and evaporated. The product obtained is chromatographed on silica, eluting with DCM/MeOH (100/4; v/v). 0.11 g of the expected compound is obtained.

EXAMPLE 8

Compound 95

N-[4-(5-Ethyl-2-methoxyphenyl)-1,3-thiazol-2-yl]-N'-(2-pyrrolidin-1-ylethyl)terephthalamide $R_1$ = 2-OMe; $R_2$ = 5-Et;   (I)

$R_3$ = e1 = 4-CONH(CH$_2$)$_2$—N 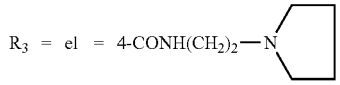

A mixture containing 0.3 g of the compound from Preparation 4.2.14, 3 ml of CH$_3$CN, 0.25 ml of ethyldiisopropylamine, 98 mg of 1-(2-aminoethyl)pyrrolidine in 2 ml of CH$_3$CN, 0.38 g of BOP and 1 ml of DMF is stirred at room temperature for 2 days. The product is filtered off, rinsed with CH$_3$CN and then dried at 60° C. over P$_2$O$_5$. 0.22 g of the expected compound is obtained. m.p.=170° C.

EXAMPLE 9

Compound 9

4-[2-(2-(S)-(Hydroxymethyl)pyrrolidin-1-yl)ethoxy]-N-[4-(2-methoxy-5-propoxyphenyl)-1,3-thiazol-2-yl]benzamide $R_1$ = 2-OMe; $R_2$ = 5-OnPr;   (I)

$R_3$ = a1 = 4-O—(CH$_2$)$_2$—N 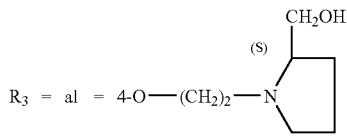

A mixture containing 0.2 g of Preparation 4.7, 3 ml of DCM, 112 µl of (S)-(+)-2-pyrrolidinemethanol, 0.2 g of NaBH(OAc)$_3$ and 5 drops of CH$_3$CO$_2$H is stirred for 18 hours. Saturated Na$_2$CO$_3$ solution, water and DCM are added to the reaction medium and the phases are then separated by settling. The organic phase is washed with water and then dried over MgSO$_4$ and evaporated. The residue is purified by chromatography on silica, eluting with a DCM/MeOH mixture (100/2, v/v). 100 mg of the expected compound are obtained. MH$^+$=511; t=5.72 minutes $[\alpha]_D^{20}$=−11.2° (c=0.848, DMSO)

EXAMPLE 10

Compound 183

N-[4-(5-Butyl-2-methoxyphenyl)-1,3-thiazol-2-yl]-4-[(4-tetrahydro-2H-pyran-4-ylamino)piperidin-1-yl)methyl]benzamide.

$R_1$ = 2-OMe; $R_2$ = 5-nBu;   (I)

$R_3$ = b = 4-CH$_2$—N 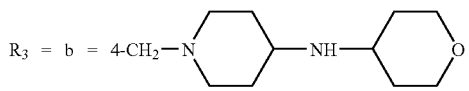 —NH—

-continued

A)

$R_1 = 2\text{-OMe}; R_2 = 5\text{-nBu};$  (IV)

$R'_3 = 4\text{-CH}_2-$

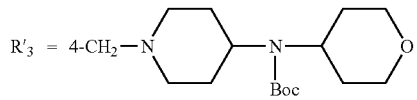

A mixture containing 0.25 g of the compound from Preparation 4.3.4 and 0.34 g of the compound from Preparation 2.1 in 1 ml of CH$_3$CN is refluxed for one hour. The product is filtered off, rinsed with CH$_3$CN and then with ether and dried at 60° C. over P$_2$O$_5$. 0.35 g of the expected compound is obtained.

B)

0.34 g of the compound obtained in the preceding step is placed in 3 ml of 4M HCl/dioxane and stirred for 5 hours at room temperature. Water is added and the product is filtered and then rinsed with ether and dried over P$_2$O$_5$ at 60° C. The resulting solid is taken up in an EtOAc/10% Na$_2$CO$_3$ mixture. After separation of the phases by settling, the organic phase is washed with 10% Na$_2$CO$_3$ and then with water, dried over MgSO$_4$ and then evaporated. The residue is purified by chromatography on silica, eluting with DCM/MeOH (90/3; v/v). 93 mg of the expected compound are obtained.

MH$^+$=562, t=5.8 minutes.

EXAMPLE 11

Compound 17

N-[2-(2-(S)-(Hydroxymethyl)pyrrolidin-1-yl)ethyl]-N'-[4-(2-methoxy-5-propoxyphenyl)-1,3-thiazol-2-yl]terephthalamide $R_1 = 2\text{-OMe}; R_2 = 5\text{-OnPr};$  n(I)

$R_3 = e_1 = 4\text{-CONH}-(CH_2)_2-$

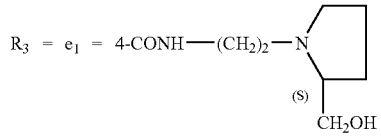

0.13 g of the compound from Preparation 4.5 in 2 ml of DCM is mixed with 54 mg of (S)-(+)-2-pyrrolidinemethanol, under dry nitrogen. After stirring for 15 minutes, 107 mg of NaBH(OAc)$_3$ and 5 drops of AcOH are added and stirring is continued for 4 hours. Saturated Na$_2$CO$_3$ solution, water and DCM are added to the reaction medium and the phases are then separated by settling. The aqueous phase is re-extracted with DCM and the extracts are washed twice with saturated NaCl solution. The organic phases are combined and dried over MgSO$_4$. After partial evaporation, CH$_3$CN and ether are added and the precipitate formed is filtered off and dried at 45° C. over P$_2$O$_5$. 57 mg of the expected compound are obtained in solid form. m.p.=168° C. (dec.).

EXAMPLE 12

Compound 14a

N-(4-(2-Methoxy-5-propoxyphenyl)-1,3-thiazol-2-yl)-4-(2-piperidin-1-ylethoxy)benzamide dihydrochloride 2HCl: $R_1 = 2\text{-OMe}; R_2 = 5\text{-OnPr};$  (I)

$R_3 = a_1 = 4\text{-O}-(CH_2)_2-$

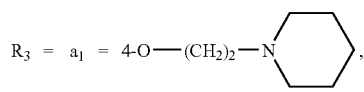

A mixture containing 0.19 g of the compound from Preparation 4.8, 62 mg of K$_2$CO$_3$ and 38 mg of piperidine in 3 ml of DMF is heated at 80° C. for 2 hours 40 minutes. The mixture is allowed to cool to RT and DCM and water are then added. The reaction medium is washed with water and then with dilute NaOH solution. The organic phase is dried over MgSO$_4$ and evaporated. The residue is chromatographed on silica, eluting with DCM/MeOH (100/2; v/v). The mixture is taken up in DCM followed by addition of hydrochloric ether, filtering and washing with ether. After drying over P$_2$O$_5$ at 60° C., 54 mg of the expected compound are obtained.

NMR spectrum: Compound 14a: 0.97 ppm:t:3H, 1.2-2.0 ppm:m:8H, 2.9-3.1 ppm:m:2H, 3.4-3.6 ppm:m:4H, 3.8-4.0 ppm:m:5H, 4.49 ppm:t:2H, 6.88 ppm:dd:1H; 7.02 ppm:d:1H; 7.13 ppm:d:2H, 7.74 ppm:s:1H; 7.77 ppm:d:1H; 8.17 ppm:d:2H, 10.4 ppm:bs:1H; 12.5 ppm:bs:1H.

EXAMPLE 13

Compound 186

Ethyl (1-(1-(4-(4-(5-butyl-2-methoxyphenyl)thiazol-2-ylcarbamoyl)piperidin-4-yl)pyrrolidin-3-yl)carbamate $R_1 = 2\text{-OMe}, R_2 = 5\text{-nBu},$  (I)

$R_3 = f2 =$

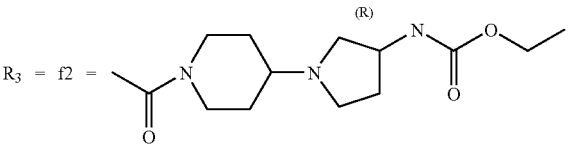

A) tert-Butyl (1-(1-(4-(4-(5-butyl-2-methoxyphenyl)thiazol-2-ylcarbamoyl)piperidin-4-yl)pyrrolidin-3-yl)carbamate 0.3 g of (3R)-3-(tert-butoxycarbonylamino)pyrrolidone is added to a solution of 0.4 g of the compound from Preparation 4.1.1 in 3 ml of dichloroethane, followed by addition of 0.35 g of NaHB(OAc)$_3$. 3 drops of acetic acid are added to the reaction medium, which is then stirred at RT for 2 hours. The medium is hydrolyzed by addition of water and then diluted with dichloromethane and washed 3 times with 1M sodium hydroxide. The organic phase is washed with saturated NaCl solution, dried over MgSO$_4$ and then evaporated to give 0.37 g of the expected compound. The crude product thus obtained may be used without further purification in the following step. m.p.=104° C. for a fraction of crude product purified by flash chromatography.

B) 4-(4-(3-Aminopyrrolidin-1-yl)piperidine-1-carbonyl)-N-(4-(5-butyl-2-methoxyphenyl)thiazol-2-yl)benzamide.

3 ml of trifluoroacetic acid are added, at 0° C., to a solution of 2.7 g of compound 151 dissolved in 9 ml of dichloromethane. The mixture is allowed to return to RT. After 2 hours at RT, the medium is evaporated and then taken up 3 times in dichloromethane and evaporated. The oil obtained is taken up in dichloromethane and then treated with 10% Na$_2$CO$_3$ solution. The organic phase is washed with 10% Na$_2$CO$_3$ solution and then with saturated NaCl solution, and then dried over MgSO$_4$ and evaporated to give 2.18 g of a beige-coloured solid. The free base is purified by trituration from a dichloro-methane/methanol mixture to give 1.9 g of the expected product. The hydrochloride is obtained by slow addition of a 2M solution of hydrogenchloride in ether to a solution of the free base in a chloroform/methanol mixture. The suspension is evaporated and then dried under vacuum to give 2 g of hydrochloride.

m.p.=188° C.

C) Ethyl (1-(1-(4-(4-(5-butyl-2-methoxyphenyl)thiazol-2-ylcarbamoyl)piperidin-4-yl)pyrrolidin-3-yl)carbamate 0.46 g of ethyl chloroformate is added to a solution of 2 g of compound 152 in its basic form in 7 ml of dichloromethane. The medium is cooled to 0° C. 0.7 g of diisopropylethylamine is then added dropwise. The medium is stirred until it has returned to RT. The medium is hydrolyzed with water and then diluted with dichloromethane. The organic phase is washed with molar sodium hydroxide solution, then with water and then with saturated NaCl solution. The organic phase is dried over MgSO$_4$ and then evaporated. The crude product is purified by flash chromatography to give 1.7 g of the expected product.

m.p.=126° C.

The solid obtained is dissolved in dichloromethane and then salified by slow addition of a 2M solution of hydrogen chloride in ether. After evaporation, 1.72 g of the hydrochloride are collected.

m.p.=178° C.

EXAMPLE 14

Compound 187

N-(4-(5-Butyl-2-methoxyphenyl)thiazol-2-yl)-4-(4-(3-methanesulphonylaminopyrrolidin-1-yl)piperidine-1-carbonyl)benzamide $R_1$ = 2-OMe, $R_2$ = 5-nBu,

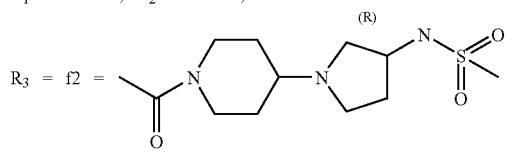

$R_3$ = f2 =

57 mg of methanesulphonyl chloride and 0.14 ml of triethylamine are added to a solution of 0.14 g of compound 152 in its basic form in 2 ml of a 1/1 mixture of ethyl acetate and DMF. After 24 hours at RT, the medium is filtered and then evaporated and taken up in ethyl acetate. The organic phase is washed twice with saturated NaCl solution, dried over MgSO$_4$ and evaporated. The crude product is purified by flash chromatography to give 65 mg of a white solid.

m.p.=125° C.

EXAMPLE 15

Compound 153

N-(4-(5-Butyl-2-methoxyphenyl)thiazol-2-yl)-4-(4-(3-propionylaminopyrrolidin-1-yl)piperidine-1-carbonyl)benzamide $R_1$ = 2-OMe, $R_2$ = 5-nBu,

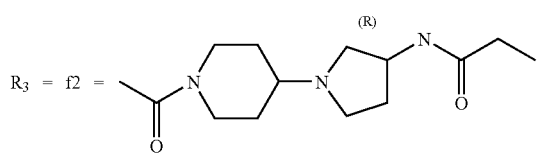

$R_3$ = f2 =

0.04 g of propionic anhydride and 0.05 ml of triethylamine are added to a solution of 0.1 g of compound 152 in its basic form in 0.5 ml of ethyl acetate. After 2 hours at RT, the medium is diluted in dichloromethane. The organic phase is washed with water and with saturated NaCl solution, dried over MgSO$_4$ and evaporated. The crude product is purified by flash chromatography to give 67 mg of a white solid.

m.p.=128° C.

EXAMPLE 16

Compound 188

1-(1-(4-(4-(5-Butyl-2-methoxyphenyl)thiazol-2-ylcarbamoyl)benzoyl)piperidin-4-yl)pyrrolidin-3-yl acetate $R_1$ = 2-OMe, $R_2$ = 5-nBu,

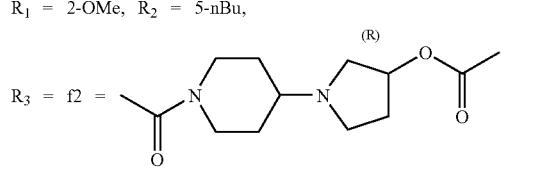

$R_3$ = f2 =

73 mg of acetic anhydride are added to a solution of 0.2 g of compound 66 dissolved in 1 ml of dichloromethane. After 2 hours at RT, a further 73 mg of acetic anhydride are added and the mixture is stirred for 12 hours at RT. The medium is diluted in dichloromethane. The organic phase is washed 3 times with 10% Na$_2$CO$_3$ solution, then with water and then with saturated NaCl solution, and then dried over MgSO$_4$ and evaporated to give 194 mg of a white solid.

m.p.=99° C.

EXAMPLE 17

Compound 189

4-(4-(1-Acetylpyrrolidin-3-ylamino)piperidine-1-carbonyl)-N-4-(5-butyl-2-methoxyphenyl)thiazol-2-yl)benzamide (I)

$R_1$ = 2-OMe, $R_2$ = 5-nBu, $R_3$ = f2 =

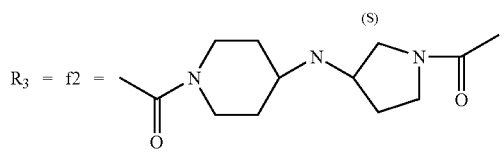

A) tert-Butyl 3-(1-(4-(4-(5-butyl-2-methoxyphenyl)thiazol-2-ylcarbamoyl)benzoyl)piperidin-4-ylamino)pyrrolidine-1-carboxylate A solution of 0.23 g of (S)-3-amino-1-N-Boc-pyrrolidine and 0.5 g of the compound from Preparation 4.1.1 in 2 ml of dichloromethane is stirred for 30 minutes at RT. 0.43 g of NaHB(OAc)$_3$ and 8 drops of acetic acid are added to the reaction mixture. The reaction medium is then stirred at RT for 4 hours. The medium is hydrolyzed by addition of water and then diluted with dichloromethane and washed 3 times with molar sodium hydroxide. The organic phase is washed with saturated NaCl solution, dried over MgSO$_4$ and then evaporated to give 0.65 g of the expected compound. The crude product thus obtained may be used without further purification in the following step.

MH$^+$=662 at t=7.3 minutes.

B) N-4-(5-Butyl-2-methoxyphenyl)thiazol-2-yl)-4-(4-(pyrrolidin-3-ylamino)piperidine-1-carbonyl)benzamide 2 ml of hydrochloric ether are added to a solution of 0.61 g of the compound obtained in the preceding step in 2 ml of dichloromethane. After 4 hours 30 minutes at RT, the medium is evaporated. The crude product is triturated from ether, filtered off, rinsed with ether and dried to give 0.51 g of the expected compound.

MH$^+$=562 at t=5.83 minutes.

C) 4-(4-(1-Acetylpyrrolidin-3-ylamino)piperidine-1-carbonyl)-N-4-(5-butyl-2-methoxyphenyl)thiazol-2-yl)benzamide A suspension of 0.5 g of the compound obtained in the preceding step in a dichloromethane/ethyl acetate mixture is treated with 10% Na$_2$CO$_3$ solution. After separation of the phases by settling, the aqueous phase is extracted with ethyl acetate and then with dichloromethane. The combined organic phases are dried over MgSO$_4$ and then evaporated.

0.37 g of free base is thus recovered, which is dissolved in 2 ml of dichloromethane. 0.062 ml of acetic anhydride is added and the mixture is stirred for 3 hours 30 minutes at RT. The medium is evaporated and then chromatographed on silica to give 0.3 g of the expected product.

MH$^+$=604 at 6.68 minutes.

The tables that follow illustrate the chemical structures and the physical properties of a few examples of compounds according to the invention. In these tables:

- in the "salt" column, "-" represents a compound in free base form, whereas "HCl" represents a compound in hydrochloride form;
- Me, Et, nPr, iPr, nBu, iBu, tBu and nHex represent, respectively, the methyl, ethyl, n-propyl, iso-propyl, n-butyl, iso-butyl, tert-butyl and n-hexyl groups;
- Ph and Bn represent, respectively, the phenyl and benzyl groups;
- THP represents tetrahydropyran-4-yl.

The compounds are characterized either by their nuclear magnetic resonance (NMR) spectrum, placed at the end of the table, or by their melting point (m.p.), or by their mass spectrum: MH$^+$ and retention time (t), expressed in minutes.

TABLE 7

(Ia)

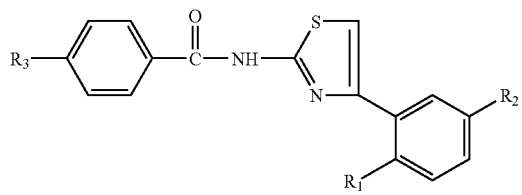

| Compound No. | $R_1$ | $R_2$ | $R_3$ | Salt | Characterization |
|---|---|---|---|---|---|
| 1 | -OMe | -OnPr | —O(CH$_2$)$_2$NEt$_2$ | 2HCl | NMR |
| 2 | -OMe | -OnPr | —O(CH$_2$)$_2$—N(morpholine) | 2HCl | MH$^+$ = 498.4<br>t = 6.64 |
| 3 | -OMe | -OnPr | —O(CH$_2$)$_2$NH(CH$_2$)$_2$OH | — | MH$^+$ = 472.4<br>t = 6.45 |
| 4 | -OMe | -OnPr | —O(CH$_2$)$_2$—N(pyrrolidine) | 2HCl | MH$^+$ = 482.3<br>t = 5.87 |

TABLE 7-continued (Ia)

[Structure: R₃-phenyl-C(=O)-NH-thiazole(with S, N)-phenyl substituted with R₂ and R₁]

| Compound No. | R₁ | R₂ | R₃ | Salt | Characterization |
|---|---|---|---|---|---|
| 5 | -OMe | -OnPr | —O(CH₂)₂NHiPr | 2HCl | MH⁺ = 470.2<br>t = 5.84 |
| 6 | -OMe | -OnPr | —O(CH₂)₂—N(piperidine-4-Ph) | 2HCl | MH⁺ = 572.5<br>t = 7.59 |
| 7 | -OMe | -OnPr | —O(CH₂)₂—N(azetidine) | — | MH⁺ = 468.4<br>t = 5.73 |
| 8 | -OMe | -OnPr | —O(CH₂)₂—N(piperidine-4-OH) | — | MH⁺ = 512.4<br>t = 5.64 |
| 9 | -OMe | -OnPr | —O(CH₂)₂—N(pyrrolidine-(S)-2-CH₂OH) | — | MH⁺ = 512.4<br>t = 5.72 |
| 10 | -OMe | -OnPr | —O(CH₂)₂—N(pyrrolidine-(R)-2-CH₂OH) | 2HCl | MH⁺ = 512.3<br>t = 5.71 |
| 11 | -OMe | -OnPr | —O(CH₂)₂NH-THP | 2HCl | MH⁺ = 512.3<br>t = 5.75 |
| 12 | -OEt | -OEt | —O(CH₂)₂NEt₂ | 2HCl | MH⁺ = 484.4<br>t = 5.94 |
| 13 | -OMe | -OnPr | —O(CH₂)₂—N(pyrrolidine-(S)-2-CH₂OMe) | 2HCl | m.p. = 122° C. (dec)<br>MH⁺ = 525.5<br>t = 6.84 |
| 14 | -SEt | -nBu | —O(CH₂)₂NEt₂ | 2HCl | MH⁺ = 512.5<br>t = 7.64 |
| 14a | -OMe | -OnPr | —O(CH₂)₂—N(piperidine) | 2HCl | NMR |
| 15 | -OMe | -OnPr | —CONH(CH₂)₂NEt₂ | — | m.p. = 204° C.<br>MH⁺ = 511.4<br>t = 5.70 |
| 16 | -OMe | -OnPr | —CONH(CH₂)₃NEt₂ | — | MH⁺ = 525.3<br>t = 5.73 |

TABLE 7-continued (Ia)

| Compound No. | R₁ | R₂ | R₃ | Salt | Characterization |
|---|---|---|---|---|---|
| 17 | -OMe | -OnPr | —CONH(CH₂)₂—N-pyrrolidinyl-(S)-CH₂OH | — | m.p. = 168° C.<br>MH⁺ = 539.3<br>t = 5.68 |
| 18 | -OMe | -OnPr | —CONHCH₂—(N-Et pyrrolidinyl) | — | m.p. = 166° C.<br>MH⁺ = 523.3<br>t = 5.86 |
| 19 | -OMe | -OnPr | —CONH(CH₂)₂—N-morpholinyl | 2HCl | MH⁺ = 525.5<br>t = 6.55 |
| 20 | -OMe | -OnPr | —CONH(CH₂)₃—N-morpholinyl | 2HCl | MH⁺ = 539.5<br>t = 6.55 |
| 21 | -OMe | -OnPr | —CON(piperidinyl-4-NMe₂) | — | MH⁺ = 523.3<br>t = 5.56 |
| 22 | -OMe | -OnPr | —CON(pyrrolidinyl-3-NH₂) | 2CF₃—CO₂H | MH⁺ = 481.5<br>t = 6.28 |
| 23 | -OMe | -OnPr | —CON(piperidinyl-4-NH-THP) | — | m.p. = 153° C.<br>MH⁺ = 579.5<br>t = 6.32 |
| 24 | -OMe | -OnPr | —CON(piperidinyl-4-(S)-pyrrolidinyl-CH₂OH) | — | m.p. = 205° C.<br>MH⁺ = 579.5<br>t = 6.31 |
| 25 | -OMe | -OnPr | —CON(piperidinyl-4-morpholinyl) | — | m.p. = 205° C. |
| 26 | -OMe | -OnPr | —CO—N(pyrrolidinyl-3-(S)-NMe₂) | — | m.p. = 178° C. |

TABLE 7-continued (Ia)

[Structure: R₃-substituted benzamide linked via C(=O)NH to a thiazole ring bearing a phenyl group with R₁ and R₂ substituents]

| Compound No. | R₁ | R₂ | R₃ | Salt | Characterization |
|---|---|---|---|---|---|
| 27 | -OMe | -OnPr | —CO—N(pyrrolidine with (S) NH₂ at 3-position) | 2CF₃—CO₂H | MH⁺ = 481.2<br>t = 6.30 |
| 28 | -OMe | -OnPr | —CONHCH₂—(2-(S)-pyrrolidinyl, N-Et) | — | m.p. = 152° C.<br>MH⁺ = 523.4<br>t = 6.52 |
| 29 | -OMe | -OnPr | —CONHCH₂—(2-(S)-pyrrolidinyl, N-Et) | 2HCl | MH⁺ = 523.3<br>t = 6.58 |
| 30 | -OMe | -OnPr | —CONHCH₂—(2-(R)-pyrrolidinyl, N-Et) | — | m.p. = 150° C.<br>MH⁺ = 523.4<br>t = 6.52 |
| 31 | -OMe | -OnPr | —CO—N(pyrrolidine with (R) NH₂ at 3-position) | 2CF₃—CO₂H | MH⁺ = 481.5<br>t = 6.10 |
| 32 | -OMe | -OnPr | —CONH—(3-(S)-pyrrolidinyl, NH) | — | MH⁺ = 481.4<br>t = 6.25 |
| 33 | -OMe | -OnPr | —(CH₂)₂—NEt₂ | 2(HO₂C—CO₂H) | NMR |
| 34 | -OMe | -OnPr | —CH(Me)NH(CH₂)₂—N(morpholine) | — | m.p. = 141° C. |
| 35 | -OMe | -nBu | —O(CH₂)₂NEt₂ | 2HCl | MH⁺ = 482.4<br>t = 6.46 |
| 36 | -OMe | -nPr | —O(CH₂)₂NEt₂ | 2HCl | MH⁺ = 468.3<br>t = 6.17 |
| 37 | -OMe | -OEt | —O(CH₂)₂NEt₂ | 2HCl | MH⁺ = 454.2<br>t = 5.84 |
| 38 | -OMe | -nPr | —O(CH₂)₂—N(pyrrolidine) | — | MH⁺ = 466.3<br>t = 6.12 |

TABLE 7-continued (Ia)

Structure: $R_3$-phenyl-C(=O)-NH-thiazole-[4-(phenyl with $R_1$ and $R_2$)]

| Compound No. | R₁ | R₂ | R₃ | Salt | Characterization |
|---|---|---|---|---|---|
| 39 | -OMe | -nPr | —O(CH₂)₂NH-THP | 2CF₃—CO₂H | MH⁺ = 496.3<br>t = 6.03 |
| 40 | -OMe | -nPr | —O(CH₂)₂NMe-THP | — | MH⁺ = 510.4<br>t = 6.13 |
| 41 | -OMe | -iPr | —O(CH₂)₂NEt₂ | 2HCl | MH⁺ = 468.4<br>t = 6.16 |
| 42 | -OMe | -Ph | —O(CH₂)₂NEt₂ | 2HCl | MH⁺ = 502.2<br>t = 7.16 |
| 43 | -OMe | cyclohexyl | —O(CH₂)₂NEt₂ | 2HCl | MH⁺ = 508.5<br>t = 7.41 |
| 44 | -OMe | -Et | —O(CH₂)₂NEt₂ | 2HCl | MH⁺ = 468.4<br>t = 6.89 |
| 45 | -OMe | —CF₃ | —O(CH₂)₂NEt₂ | 2HCl | MH⁺ = 494.5<br>t = 6.68 |
| 46 | -OMe | -nBu | —O(CH₂)₂-N-pyrrolidinyl-(S)-2-CH₂OH | — | MH⁺ = 510.4<br>t = 7.11 |
| 47 | -OMe | cyclohexyl | —O(CH₂)₂NH-THP | 2HCl | MH⁺ = 536.4<br>t = 7.31 |
| 48 | -OEt | tert-Pentyl | —O(CH₂)₂NEt₂ | — | m.p. = 116° C.<br>MH⁺ = 510.5<br>t = 7.60 |
| 49 | -OMe | -secBu | —O(CH₂)₂NEt₂ | 2HCl | m.p. = 150-156° C.<br>MH⁺ = 482.5<br>t = 7.24 |
| 50 | -OMe | -tertBu | —O(CH₂)₂NEt₂ | 2HCl | m.p. = 149-151° C.<br>MH⁺ = 482.4<br>t = 6.05 |
| 51 | -OMe | -nBu | —O—CH₂-(S)-pyrrolidin-2-yl (NH) | 2HCl | MH⁺ = 466.3<br>t = 7.09 |
| 52 | -OMe | -nBu | —O-(S)-pyrrolidin-3-yl (NH) | 2HCl | MH⁺ = 452.4<br>t = 7.01 |
| 53 | -OMe | cyclopentyl | —(CH₂)₂NEt₂ | 2HCl | MH⁺ = 494.4<br>t = 7.23 |
| 54 | -OMe | -nBu | —O-piperidin-3-yl (R,S) (NH) | 2HCl | MH⁺ = 466.4<br>t = 7.12 |

TABLE 7-continued (Ia)

[Structure: R₃-C₆H₄-C(=O)-NH-thiazole(N,S)-C₆H₃(R₁)(R₂)]

| Compound No. | R₁ | R₂ | R₃ | Salt | Characterization |
|---|---|---|---|---|---|
| 55 | -OMe | —OCHEt₂ | —(CH₂)₂NEt₂ | 2HCl | MH⁺ = 496.4<br>t = 7.29 |
| 56 | -OMe | -nBu | —O-(R)-pyrrolidin-3-yl (NH) | 2HCl | MH⁺ = 452.4<br>t = 6.98 |
| 57 | -OMe | cyclohexyl | —O—CH₂-(S)-pyrrolidin-2-yl (NH) | 2HCl | MH⁺ = 492.4<br>t = 7.33 |
| 58 | -OMe | —CH-(nPr)₂ | —O(CH₂)₂NEt₂ | 2HCl | MH⁺ = 524.4<br>t = 7.84 |
| 59 | —O—CH₂-cyclopropyl | -nBu | —O(CH₂)₂NEt₂ | 2HCl | MH⁺ = 522.4<br>t = 7.81 |
| 60 | -OEt | cyclohexyl | —OCH₂-(S)-pyrrolidin-2-yl (NH) | 2HCl | MH⁺ = 506.3<br>t = 7.53 |
| 61 | -OMe | -nBu | —OCH₂-(R)-pyrrolidin-2-yl (NH) | 2HCl | MH⁺ = 466.3<br>t = 6.93 |
| 62 | -OEt | -nBu | —O(CH₂)₂NEt₂ | 2HCl | MH⁺ = 496.3<br>t = 7.56 |
| 63 | -OMe | -nBu | —O(CH₂)₂NEt₂ | 2HCl | MH⁺ = 510.3<br>t = 7.90 |
| 64 | -OnPr | -nBu | —CONH(CH₂)₂-morpholine | — | MH⁺ = 523.3<br>t = 6.22 |
| 65 | -OMe | -nBu | —CO-N(piperidine)-4-[(S)-2-(CH₂OH)-pyrrolidin-1-yl] | — | m.p. = 199° C. MH⁺ = 577.5<br>t = 6.83 |
| 66 | -OMe | -nBu | —CO-N(piperidine)-4-[(R)-3-OH-pyrrolidin-1-yl] | — | MH⁺ = 563.3<br>t = 6.84 |
| 67 | -OMe | -nBu | —CO-N(piperidine)-4-NH-THP | -NMR | 160° C. dec<br>MH⁺ = 577.5<br>t = 6.84;<br>NMR |
| 68 | -OMe | -nBu | —CO-N(piperidine)-4-NH-THP | 2HCl | m.p. = 181-189° C.<br>MH⁺ = 577.5<br>t = 6.80 |

TABLE 7-continued

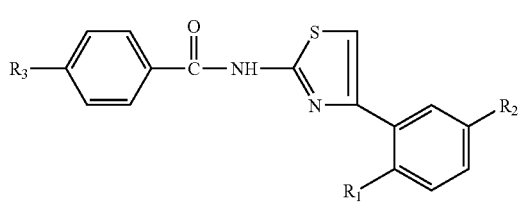
(Ia)

| Compound No. | R₁ | R₂ | R₃ | Salt | Characterization |
|---|---|---|---|---|---|
| 69 | -OMe | -Et | —CON(piperidine-4-yl)-N-morpholine | — | NMR |
| 70 | -OMe | -Et | —CON(piperidine-4-yl)-NH-THP | — | NMR |
| 71 | -OMe | -Et | —CONH(CH₂)₂-N-morpholine | — | m.p. = 208° C.<br>MH⁺ = 494<br>t = 6.39 |
| 72 | -OMe | -Et | —CON(piperidine-4-yl)-N-pyrrolidine-(R)-CH₂OH | — | MH⁺ = 549.5<br>t = 6.35 |
| 73 | -OMe | -Et | —CON(piperidine-4-yl)-N-pyrrolidine-(S)-CH₂OH | — | MH⁺ = 549.5<br>t = 6.35 |
| 74 | -OMe | -nBu | —CON(piperidine-4-yl)-N-pyrrolidine-(R)-CH₂OH | — | m.p. = 190° C.<br>MH⁺ = 577.5<br>t = 6.98 |
| 75 | -OMe | -Et | —CON(piperidine-4-yl)-N-pyrrolidine-(S)-OH | — | m.p. ≅ 140° C.<br>MH⁺ = 535.4<br>t = 6.27 |
| 76 | -OMe | -Et | —CONHCH₂-(S)-pyrrolidine-N-Et | — | m.p. = 90° C.<br>MH⁺ = 493.4<br>t = 6.45 |
| 77 | -OMe | -Et | —CON(piperidine-4-yl)-N-pyrrolidine-(R)-OH | — | m.p. ≅ 143° C.<br>MH⁺ = 535.4<br>t = 6.22 |

TABLE 7-continued (Ia)

| Compound No. | R₁ | R₂ | R₃ | Salt | Characterization |
|---|---|---|---|---|---|
| 78 | -OMe | -Et | —CON(piperidine-4-yl)-N(pyrrolidine), (S)-MeCO—NH substituent | — | m.p. = 225° C.<br>MH⁺ = 576.4<br>t = 6.16 |
| 79 | -OMe | -Et | —CON(piperidine-4-yl)-N(pyrrolidine), (S)-MeOCH₂ substituent | — | m.p. = 165° C.<br>MH⁺ = 563.4<br>t = 6.42 |
| 80 | -OMe | -nBu | —CON(piperidine-4-yl)-N(pyrrolidine), (S)-OH substituent | — | m.p. ≅ 129° C.<br>MH⁺ = 563.5<br>t = 6.68 |
| 81 | -OMe | -nBu | —CON(piperidine-4-yl)-NH—(CH₂)₃OH | — | m.p. = 140° C.<br>MH⁺ = 551.5<br>t = 6.73 |
| 82 | -OMe | -Me | —CON(piperidine-4-yl)-N(pyrrolidine), (R)-OH substituent | — | m.p. ≅ 155° C.<br>MH⁺ = 521.4<br>t = 5.87 |
| 83 | -OMe | -nBu | —CONHCH₂-(pyrrolidine, (R,S)), N-Et | — | m.p. ≅ 76° C.<br>MH⁺ = 521.4<br>t = 7.13 |
| 84 | -OMe | -Me | —CON(piperidine-4-yl)-NH-THP | — | m.p. = 198° C.<br>MH⁺ = 535.5<br>t = 5.96 |
| 85 | -OMe | -Me | —CON(piperidine-4-yl)-N(pyrrolidine), (S)-CH₂OH substituent | — | m.p. = 160° C.<br>MH⁺ = 535.5<br>t = 5.93 |
| 86 | -OMe | -nBu | —CON(piperidine-4-yl)-N(piperidine), (R,S)-OH substituent | — | m.p. = 170° C.<br>MH⁺ = 577.5<br>t = 6.80 |

TABLE 7-continued (Ia)

| Compound No. | R₁ | R₂ | R₃ | Salt | Characterization |
|---|---|---|---|---|---|
| 87 | -OMe | -nPr | —CONHCH₂-[pyrrolidine-2-yl, N-Et], R,(S) | — | m.p. = 158° C.<br>MH⁺ = 507.5<br>t = 6.76 |
| 88 | -OMe | -nPr | —CONHCH₂-[pyrrolidine-2-yl, N-Et], (S) | — | m.p. = 102° C.<br>MH⁺ = 507.4<br>t = 6.68 |
| 89 | -OMe | -nPr | —CONHCH₂-[pyrrolidine-2-yl, N-Et], (R) | — | m.p. = 160° C.<br>MH⁺ = 507.4<br>t = 6.79 |
| 90 | -OMe | -nBu | —CON(piperidine)-NH(CH₂)₂OH | — | MH⁺ = 537.5<br>t = 6.67 |
| 91 | -OMe | -nBu | —CONHCH₂-[pyrrolidine-2-yl, N-Et], (S) | — | m.p. = 208° C.<br>MH⁺ = 521.5<br>t = 7.30 |
| 92 | -OMe | -nBu | —CONHCH₂-[pyrrolidine-2-yl, N-Et], (R) | — | m.p. = 132° C.<br>MH⁺ = 521.3<br>t = 7.04 |
| 93 | -OMe | -Et | —CON(piperidine)-NH(CH₂)₂NHCOMe | — | MH⁺ = 550.4<br>t = 6.30 |
| 94 | -OMe | -Et | —CON(piperidine)-NH(CH₂)₂OH | — | MH⁺ = 509.4<br>t = 6.28 |
| 95 | -OMe | -Et | —CONH(CH₂)₂-N(pyrrolidine) | — | m.p. = 170° C.<br>MH⁺ = 479.5<br>t = 6.44 |
| 96 | -OMe | -Et | —CONH(CH₂)₂NH₂ | 2HCl | MH⁺ = 425.4<br>t = 6.32 |
| 97 | -OMe | -Et | —CONH(CH₂)₂NEt₂ | 2HCl | m.p. = 130° C. dec<br>MH⁺ = 481.4<br>t = 6.55 |

TABLE 7-continued

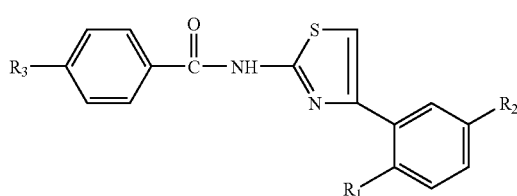

(Ia)

| Compound No. | R$_1$ | R$_2$ | R$_3$ | Salt | Characterization |
|---|---|---|---|---|---|
| 98 | -OMe | -Et | —CON(piperidine-4-)N(Me)(CH$_2$)$_2$OH | — | m.p. = 146° C. MH$^+$ = 523.5 t = 6.29 |
| 99 | -OMe | -Et | —CONH(CH$_2$)$_2$NHCOMe | — | m.p. > 260° C. MH$^+$ = 467.4 t = 8.04 |
| 100 | -OMe | -nBu | —CON(piperidine-4-)NHCH$_2$THP | — | m.p. = 177° C. MH$^+$ = 591.4 t = 5.95 |
| 101 | -OMe | -Et | —CONHCH$_2$-(S)-(1-Et-pyrrolidin-2-yl) | 2HCl | MH$^+$ = 493.5 t = 6.59 |
| 102 | -OMe | -nBu | —CON(piperidine-4-)-(R)-(3-OH-pyrrolidin-1-yl) | 2HCl | m.p. = 187° C. MH$^+$ = 535.4 t = 6.12 |
| 103 | -OMe | -nBu | —CON(piperidine-4-)-(3-OH-azetidin-1-yl) | 2HCl | MH$^+$ = 549.5 t = 6.75 |
| 104 | -OMe | -nBu | —CON(piperidine-4-)-(S)-(3-MeCONH-pyrrolidin-1-yl) | — | m.p. = 207° C. MH$^+$ = 604.4 t = 6.74 |
| 105 | -OMe | -nBu | —CON(piperidine-4-)NH(CH$_2$)$_2$OH | 2HCl | MH$^+$ = 537.4 t = 6.69 |
| 106 | -OMe | -nBu | —CON(piperidine-4-)-(pyrrolidin-1-yl) | — | MH$^+$ = 547.4 t = 6.83 |
| 107 | -OMe | -nBu | —CON(piperidine-4-)-(pyrrolidin-1-yl) | 2HCl | MH$^+$ = 547.3 t = 6.93 |
| 108 | -OMe | -nBu | —CONHCH$_2$-(pyrrolidin-2-yl) | 2HCl | m.p. = 196° C. MH$^+$ = 493.3 t = 6.84 |

TABLE 7-continued (Ia)

| Compound No. | R₁ | R₂ | R₃ | Salt | Characterization |
|---|---|---|---|---|---|
| 109 | -OMe | -nBu | —CON⟨bicyclic⟩NH (1S, 4S) | 2HCl | m.p. = 192° C.<br>MH⁺ = 492.4<br>t = 6.65 |
| 110 | -OMe | -nBu | —CON(piperidine-4-yl)-morpholine | — | MH⁺ = 563.3<br>t = 6.84 |
| 111 | -OMe | -nBu | —CON(piperazine)-Me | — | m.p. = 180° C.<br>MH⁺ = 494.3<br>t = 6.80 |
| 112 | -OMe | -nBu | —CON(piperidine-4-yl)-NH(CH₂)₂—NHCOMe | — | MH⁺ = 578.4<br>t = 6.80 |
| 113 | -OMe | -nBu | —CON(piperidine-4-yl)-piperidine with CONH₂ | — | m.p. = 150° C.<br>MH⁺ = 604.4<br>t = 6.91 |
| 114 | -OEt | -Et | —CON(piperidine-4-yl)-pyrrolidine (S) NHCOMe | — | m.p. = 153° C.<br>MH⁺ = 590.4<br>t = 6.41 |
| 115 | -OMe | -nBu | —CON(piperidine-4-yl)-spirocyclic lactam | — | MH⁺ = 630.4<br>t = 6.74 |
| 116 | -OEt | -Et | —CONH(piperidine-3-yl) | 2HCl | m.p. = 171° C.<br>MH⁺ = 479.4<br>t = 6.57 |
| 117 | -OEt | -Et | —CON(piperidine-4-yl)-NHTHP | — | m.p. = 171° C.<br>MH⁺ = 563.4<br>t = 6.50 |
| 118 | -OMe | -nBu | —CON(pyrrolidine) (S) CH₂—N(pyrrolidine) | — | MH⁺ = 547.4<br>t = 7.18 |

TABLE 7-continued

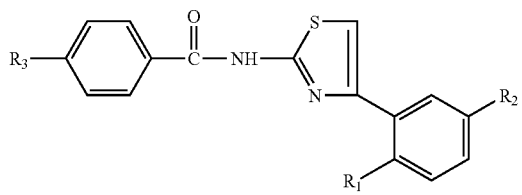

(Ia)

| Compound No. | R$_1$ | R$_2$ | R$_3$ | Salt | Characterization |
|---|---|---|---|---|---|
| 119 | -OEt | -Et | —CON⟨pyrrolidine(S)⟩—CH$_2$—N⟨pyrrolidine⟩ | 2HCl | MH$^+$ = 533.4<br>t = 6.75 |
| 120 | -OMe | -nBu | —CON⟨piperidine⟩—N⟨pyrrolidine⟩(R)-NHCOMe | — | m.p. = 200° C. dec<br>MH$^+$ = 604.5<br>t = 6.65 |
| 121 | -OEt | -Et | —CON⟨piperidine⟩—N⟨azetidine⟩—OH | — | m.p. = 136° C.<br>MH$^+$ = 535.3<br>t = 6.37 |
| 122 | -OEt | -Et | —CONHCH$_2$—⟨pyrrolidine NH⟩ (R, S) | 2HCl | m.p. = 145° C.<br>MH$^+$ = 479.3<br>t = 6.52 |
| 123 | -OEt | -Et | —CON⟨piperidine⟩—N⟨pyrrolidine⟩(R)-OH | — | m.p. = 134° C.<br>MH$^+$ = 549.3<br>t = 6.34 |
| 124 | -OMe | -nBu | —CON⟨piperidine⟩—N⟨azetidine⟩ | — | MH$^+$ = 533.4<br>t = 6.91 |
| 125 | -OEt | -Et | —CONHCH$_2$—⟨pyrrolidine N-Et⟩ (S) | 2HCl | m.p. = 136° C.<br>MH$^+$ = 507.4<br>t = 6.75 |
| 126 | -OMe | -nBu | —CON⟨piperidine⟩—N⟨pyrrolidine⟩(S)-CF$_3$CONH | — | MH$^+$ = 658.3<br>t = 7.14 |
| 127 | -OMe | -nBu | —CON⟨piperidine⟩—N⟨pyrrolidine⟩(R,S)-MeCONMe | 2HCl | MH$^+$ = 618.4<br>t = 6.79 |
| 128 | -OMe | -nBu | —CON⟨piperidine⟩—NH(CH$_2$)$_2$CONH$_2$ | 2HCl | MH$^+$ = 564.6<br>t = 6.69 |

TABLE 7-continued
(Ia)
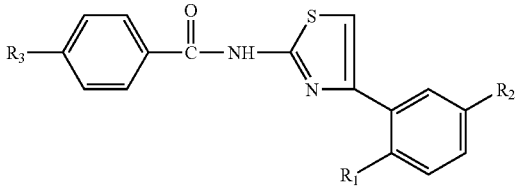
| Compound No. | R₁ | R₂ | R₃ | Salt | Characterization |
|---|---|---|---|---|---|
| 129 | -OEt | -Et | 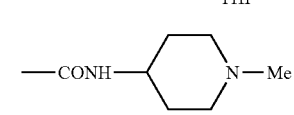 | — | m.p. = 170° C.<br>MH⁺ = 563.4<br>t = 6.74 |
| 130 | -OMe | -nBu | 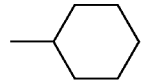 | — | m.p. = 222° C.<br>MH⁺ = 507.3<br>t = 6.80 |
| 131 | -OEt | 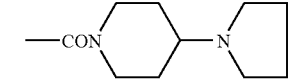 | 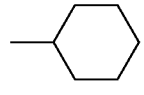 | — | m.p. = 143° C.<br>MH⁺ = 487.5<br>t = 7.53 |
| 132 | -OEt | 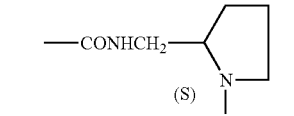 | 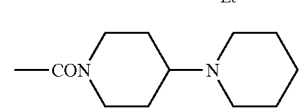 | — | m.p. = 97° C.<br>MH⁺ = 561.4<br>t = 7.74 |
| 133 | -OMe | -nBu | 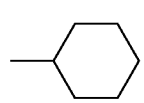 | — | m.p. = 188° C.<br>MH⁺ = 561.4<br>t = 6.99 |
| 134 | -OMe | 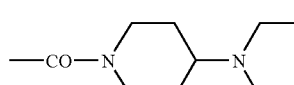 | 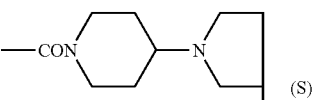 | — | m.p. = 192° C.<br>MH⁺ = 573.4<br>t = 7.16 |
| 135 | -OEt | -Et | 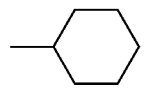 | 2HCl | MH⁺ = 590.3<br>t = 6.49 |
| 136 | -OMe | 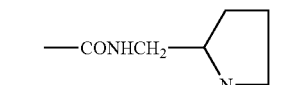 | 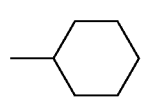 | 2HCl | MH⁺ = 519.3<br>t = 7.03 |
| 137 | -OMe | 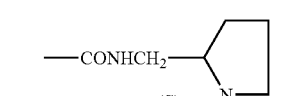 |  | — | m.p. = 104° C.<br>MH⁺ = 547.3<br>t = 7.18 |
| 138 | -OMe | -nBu | 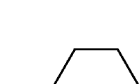 | 2HCl | MH⁺ = 494.3<br>t = 6.96 |
| 139 | -OEt | 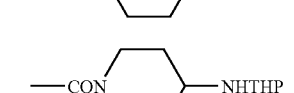 | 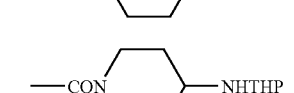 | 2HCl | MH⁺ = 617.3<br>t = 7.32 |

TABLE 7-continued (Ia)

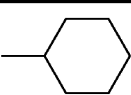

| Compound No. | R₁ | R₂ | R₃ | Salt | Characterization |
|---|---|---|---|---|---|
| 140 | -OMe | 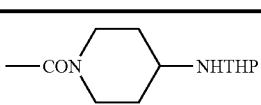 | —CON⟨piperidine⟩—NHTHP | 2HCl | MH⁺ = 603.3<br>t = 7.03 |
| 141 | -OMe | -nBu | —CON⟨piperidine⟩—NHTHP | — | MH⁺ = 563.4<br>t = 6.42 |
| 142 | -OMe | -nBu | —CON⟨piperidine⟩—N(Me)-THP | — | MH⁺ = 591.3<br>t = 6.84 |
| 143 | -OMe | -nBu | —CON⟨piperidine⟩—N(nPr)-THP | — | MH⁺ = 619.4<br>t = 7.07 |
| 144 | -OMe | 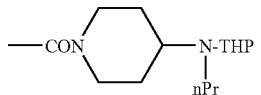 | —CONHCH₂—⟨(R,S) N-Et pyrrolidine⟩ | — | m.p. = 134° C.<br>MH⁺ = 533.3<br>t = 7.03 |
| 145 | -OMe | -nBu | —CONH—⟨piperidine⟩NH | 2HCl | MH⁺ = 493.3<br>t = 6.81 |
| 146 | -OMe | -nPr | —CON⟨piperidine⟩—N⟨pyrrolidine⟩ | — | m.p. = 163° C.<br>MH⁺ = 533.3<br>t = 6.56 |
| 147 | -OMe | -nBu | —CONH—⟨piperidine⟩N-THP | — | m.p. ≅ 170° C.<br>MH⁺ = 577.3<br>t = 6.82 |
| 148 | -OMe | 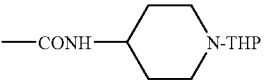 | —CON⟨piperidine⟩—NH-THP | 2HCl | m.p. ≅ 180° C.<br>MH⁺ = 589.3<br>t = 6.76 |
| 149 | -OMe | -nHex | —CON⟨piperidine⟩—NH-THP | 2HCl | MH⁺ = 605.3<br>t = 7.35 |
| 150 | -OMe | 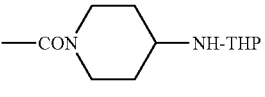 | —CON⟨piperidine⟩—N⟨(R) pyrrolidine, HNCOMe⟩ | — | m.p. = 164° C. dec<br>MH⁺ = 630.4<br>t = 6.97 |

TABLE 7-continued (Ia)

| Compound No. | R₁ | R₂ | R₃ | Salt | Characterization |
|---|---|---|---|---|---|
| 151 | -OMe | -nBu | —CON⟩–⟨N⟩ (R) tBuOCONH | — | m.p. = 104° C. MH⁺ = 662.3 t = 7.33 |
| 152 | -OMe | -nBu | —CON⟩–⟨N⟩ (R) NH₂ | 3HCl | m.p. = 188° C. MH⁺ = 561.9 t = 5.82 |
| 153 | -OMe | -nBu | —CON⟩–⟨N⟩ (R) NHCOEt | — | m.p. = 128° C. MH⁺ = 618.3 t = 6.84 |
| 154 | -OMe | -nBu | —CON⟩–⟨N⟩ (R) NHCHO | — | m.p. = 148° C. MH⁺ = 590.3 t = 6.73 |
| 155 | -OMe | cyclohexyl | —CON⟩–⟨N⟩ (S) CH₂OH | 2HCl | MH⁺ = 603.3 t = 7.08 |
| 156 | -OMe | -nBu | —CONHCH₂–(2-piperidinyl) | — | m.p. = 182° C. MH⁺ = 507.4 t = 6.89 |
| 157 | -OMe | -nPr | —CON⟩–⟨N⟩ (R) HNCOMe | — | m.p. = 230° C. MH⁺ = 590.3 t = 6.39 |
| 158 | -OMe | -nPr | —CON⟩–⟨N⟩ (R) CH₂OH | — | m.p. = 226° C. MH⁺ = 563.2 t = 6.51 |
| 159 | -OMe | -nBu | —CON⟩(endo)–NHTHP | — | m.p. = 94° C. dec MH⁺ = 603.3 t = 6.86 |

TABLE 7-continued

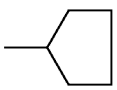

(Ia)

| Compound No. | R₁ | R₂ | R₃ | Salt | Characterization |
|---|---|---|---|---|---|
| 160 | -OMe | 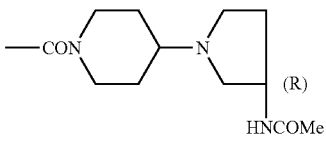 | 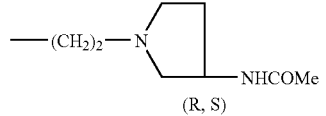  —CON(piperidine)-N(pyrrolidine)(R)-HNCOMe | — | m.p. = 148° C.<br>MH⁺ = 616.3<br>t = 6.66 |
| 161 | -OMe | -nBu | —(CH₂)₂—N(pyrrolidine)(R,S)-NHCOMe | — | m.p. = 112° C.<br>MH⁺ = 521.4<br>t = 6.98 |
| 162 | -OMe | -Et | —(CH₂)₃NEt₂ | 2HCl | MH⁺ = 452.5<br>t = 6.76 |
| 163 | -OMe | -Et | —(CH₂)₃—N(pyrrolidine)(S)-CH₂OMe | — | MH⁺ = 494.5<br>t = 6.95 |
| 164 | -OMe | -nBu | —(CH₂)₂—N(pyrrolidine)(R,S)-OH | — | MH⁺ = 480.4<br>t = 7.18 |
| 165 | -OMe | -nBu | —(CH₂)₂—N(pyrrolidine)(R,S)-NMe₂ | — | MH⁺ = 507.5<br>t = 6.25 |
| 166 | -OMe | -Et | —(CH₂)₃—N(pyrrolidine)(S)-NHCOMe | — | MH⁺ = 507.6<br>t = 6.62 |
| 167 | -OMe | -nBu | —(CH₂)₂—N(pyrrolidine)(S)-CH₂OH | — | MH⁺ = 494.4<br>t = 7.76 |
| 168 | -OMe | -Et | —(CH₂)₃—N(pyrrolidine)(R)-OH | — | MH⁺ = 466.4<br>t = 6.57 |

TABLE 7-continued

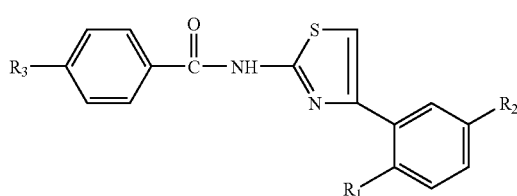

(Ia)

| Compound No. | $R_1$ | $R_2$ | $R_3$ | Salt | Characterization |
|---|---|---|---|---|---|
| 169 | -OMe | -Et | —(CH$_2$)$_2$—N[pyrrolidine-3-NHCOMe] (R, S) | — | MH$^+$ = 493.5<br>t = 6.93 |
| 170 | -OMe | -Et | —(CH$_2$)$_2$—N[pyrrolidine-3-OH] (R, S) | — | MH$^+$ = 452.4<br>t = 6.94 |
| 171 | -OMe | -Et | —(CH$_2$)$_3$NH(CH$_2$)$_2$OH | — | m.p. = 140° C. dec<br>MH$^+$ = 440.4<br>t = 7.11 |
| 172 | -OMe | -Et | —(CH$_2$)$_3$NH-THP | 2HCl | MH$^+$ = 480.5<br>t = 6.54 |
| 173 | -OMe | -Et | —(CH$_2$)$_3$—N[pyrrolidine-2-CH$_2$OH] (R) | — | MH$^+$ = 480.4<br>t = 6.49 |
| 174 | -OMe | -Et | —(CH$_2$)$_3$—N[pyrrolidine] | 2HCl | MH$^+$ = 450.5<br>t = 6.54 |
| 175 | -OMe | -Et | —(CH$_2$)$_3$—N[azetidine-3-OH] | 2HCl | MH$^+$ = 452.4<br>t = 6.35 |
| 176 | -OMe | -nBu | [4-methylpiperidine-NH] | 2HCl | m.p. = 173° C.<br>MH$^+$ = 450.4<br>t = 7.18 |
| 177 | -OMe | -nBu | —(CH$_2$)$_3$—N[azetidine-3-OH] | — | MH$^+$ = 480.4<br>t = 7.13 |
| 178 | -OMe | -nBu | —(CH$_2$)$_3$—N[pyrrolidine-3-OH] (R) | — | MH$^+$ = 494.4<br>t = 7.04 |
| 179 | -OMe | -nBu | —(CH$_2$)$_3$—N[pyrrolidine-3-NHCOMe] (S) | — | MH$^+$ = 535.4<br>t = 6.99 |

TABLE 7-continued

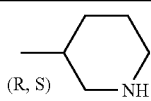
(Ia)

| Compound No. | R₁ | R₂ | R₃ | Salt | Characterization |
|---|---|---|---|---|---|
| 180 | -OMe | -nBu | 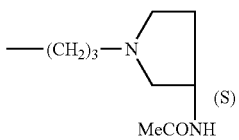 (R, S) | 2HCl | m.p. = 220° C.<br>MH⁺ = 450.4<br>t = 7.19 |
| 181 | -OEt | -Et | —(CH₂)₃— (S)<br>MeCONH | — | MH⁺ = 521.4<br>t = 6.63 |
| 182 | -OMe | -nBu | —(CH₂)₃NH-THP | — | m.p. = 150° C.<br>MH⁺ = 508.4<br>t = 7.10 |
| 183 | -OMe | -nBu | —CH₂——NH-THP | — | m.p. = 80° C. dec<br>MH⁺ = 563.4<br>t = 5.80 |
| 184 | -OMe | -nBu | —CH₂——NH-THP | — | m.p. = 80° C. dec<br>MH⁺ = 577.3<br>t = 5.94 |
| 185 | -OMe | -Et | —CH₂NHCH₂—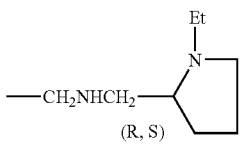 (R, S) | 2HCl | m.p. = 163° C. dec<br>MH⁺ = 479.4<br>t = 6.14 |
| 186 | -OMe | -nBu | 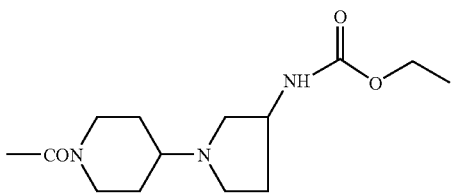 | HCl | m.p. = 178° C.<br>MH⁺ = 634<br>t = 7.03 |
| 187 | -OMe | -nBu | 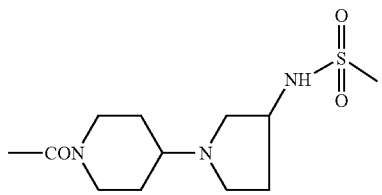 | — | m.p. = 125° C.<br>MH⁺ = 640<br>t = 6.88 |
| 188 | -OMe | -nBu | 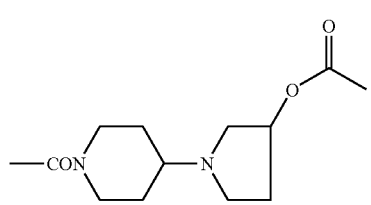 | — | m.p. = 99° C.<br>MH⁺ = 605<br>t = 6.92 |

TABLE 7-continued

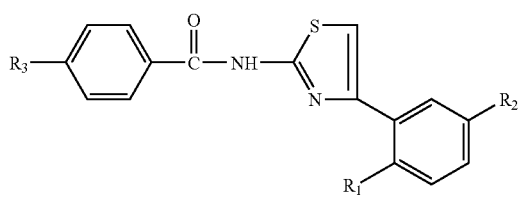
(Ia)

| Compound No. | R₁ | R₂ | R₃ | Salt | Characterization |
|---|---|---|---|---|---|
| 189 | -OMe | -nBu | —CON⟨piperidine-4-yl⟩NH—[(S)-1-acetylpyrrolidin-3-yl] | — | MH⁺ = 604<br>t = 6.68 |
| 190 | -OMe | -OnPr | —CH₂NH-(tetrahydropyran-4-yl) | — | m.p. = 210° C. |
| 191 | -OMe | —F | —O(CH₂)₂NEt₂ | HCl | m.p. = 228° C. |
| 192 | -OMe | -nHex | —O(CH₂)₂NEt₂ | HCl | MH⁺ = 510<br>t = 7.73 |
| 193 | -OEt | -nHex | —O(CH₂)₂NEt₂ | HCl | m.p. = 182° C.<br>MH⁺ = 524<br>t = 8.05 |
| 194 | -OMe | 1-adamantyl | —O(CH₂)₂NEt₂ | HCl | MH⁺ = 560<br>t = 7.93 |
| 195 | -OEt | -nPr | —O(CH₂)₂NEt₂ | — | MH⁺ = 482<br>t = 7.11 |
| 196 | -OMe | —CF₂CF₃ | —O(CH₂)₂NEt₂ | — | MH⁺ = 544<br>t = 6.79 |
| 197 | -OMe | cyclohexyl | —CON⟨piperidine-4-yl⟩N-[(R)-3-(Boc-amino)pyrrolidin-1-yl] | — | MH⁺ = 688<br>t = 7.53 |
| 198 | -OMe | -nBu | —CON⟨piperidine-4-yl⟩N-[(R)-3-(propionyloxy)pyrrolidin-1-yl] | — | m.p. = 158° C.<br>MH⁺ = 619<br>t = 7.09 |
| 199 | -OMe | cyclohexyl | —CON⟨piperidine-4-yl⟩N-[(R)-3-aminopyrrolidin-1-yl] | — | MH⁺ = 588<br>t = 6.06 |

TABLE 7-continued
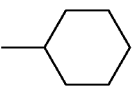
(Ia)
| Compound No. | R₁ | R₂ | R₃ | Salt | Characterization |
|---|---|---|---|---|---|
| 200 | -OMe | 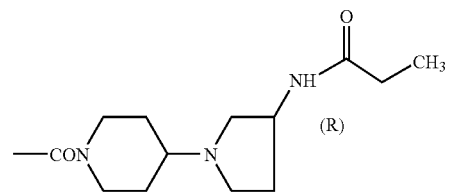 | 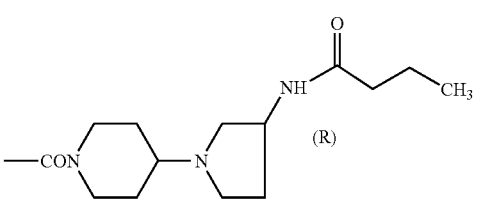 | — | MH⁺ = 643<br>t = 7.06 |
| 201 | -OMe | -nBu | 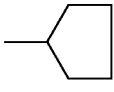 | — | MH⁺ = 632<br>t = 7.01 |
| 202 | -OMe | 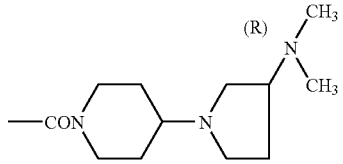 | 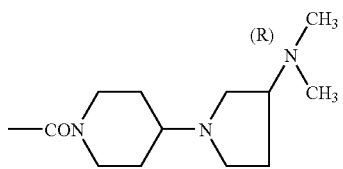 | — | MH⁺ = 602<br>t = 5.94 |
| 203 | -OMe | -nPr | 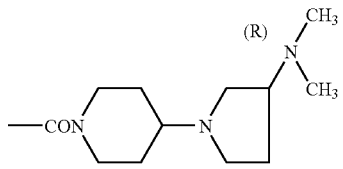 | — | MH⁺ = 576<br>t = 5.64 |
| 204 | -OMe | -nBu | 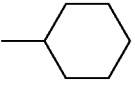 | — | MH⁺ = 590<br>t = 5.91 |
| 205 | -OMe | 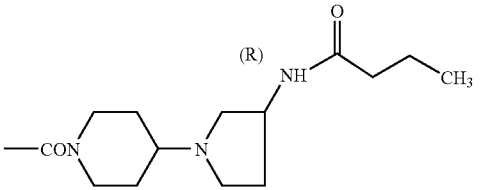 | (shown at left: cyclohexyl)<br>—CON⟨piperidine⟩—N⟨pyrrolidine, (R)⟩—NH—C(O)—CH₂CH₃ | — | MH⁺ = 658<br>t = 7.28 |

TABLE 7-continued
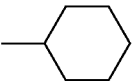
(Ia)
| Compound No. | R₁ | R₂ | R₃ | Salt | Characterization |
|---|---|---|---|---|---|
| 206 | -OEt | 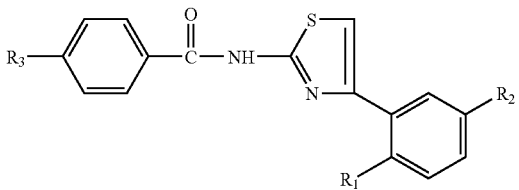 | 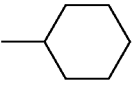 | — | m.p. = 156° C.<br>MH⁺ = 644<br>t = 7.33 |
| 207 | -OMe | 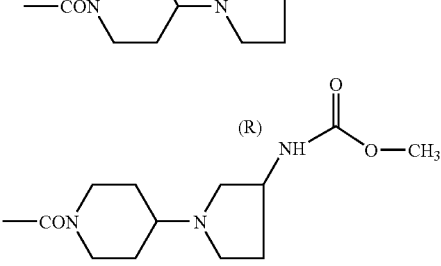 | 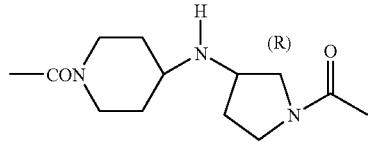 | — | m.p. = 121° C.<br>MH⁺ = 646<br>t = 7.24 |
| 208 | -OMe | -nBu | 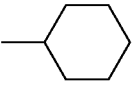 | — | m.p. = 158° C.<br>MH⁺ = 604<br>t = 6.78 |
| 209 | -OEt | 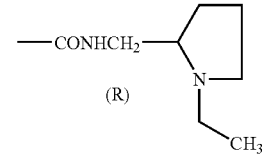 | 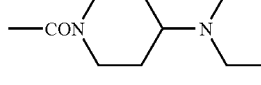 | — | MH⁺ = 561<br>t = 7.77 |
| 210 | -OEt | -Et | 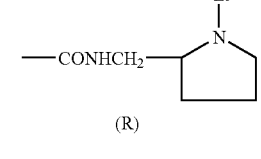 | — | m.p. = 125° C.<br>MH⁺ = 533<br>t = 6.53 |
| 211 | -OEt | -Et | 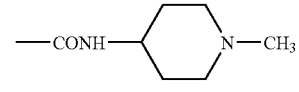 | — | m.p. = 151° C.<br>MH⁺ = 507<br>t = 6.75 |
| 212 | -OEt | -Et | —CONH—⟨N-piperidine⟩—CH₃ | — | m.p. = 230° C.<br>MH⁺ = 493<br>t = 6.69 |
| 213 | -OMe | -nBu | 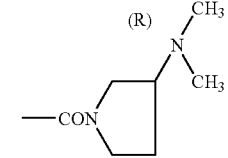 | — | m.p. = 97° C.<br>MH⁺ = 507<br>t = 6.76 |

TABLE 7-continued
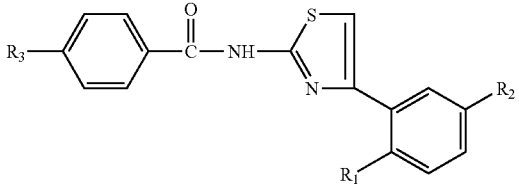
(Ia)
| Compound No. | R₁ | R₂ | R₃ | Salt | Characterization |
|---|---|---|---|---|---|
| 214 | -OMe | -nBu | 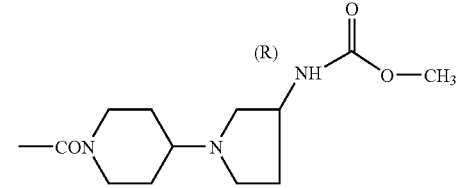 | — | m.p. = 230° C.<br>MH⁺ = 479<br>t = 6.84 |
| 215 | -OMe | -nBu | 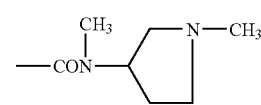 | — | m.p. = 112° C.<br>MH⁺ = 620<br>t = 6.89 |
| 216 | -OMe | -nBu | 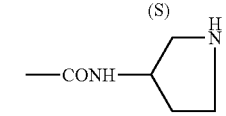 | — | m.p. = 195° C.<br>MH⁺ = 507<br>t = 6.23 |
| 217 | -OMe | -nBu | 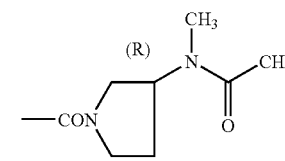 | — | m.p. = 221° C.<br>MH⁺ = 479<br>t = 6.79 |
| 218 | -OMe | -nBu | 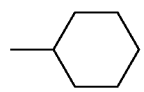 | — | m.p. = 142° C.<br>MH⁺ = 535<br>t = 9.04 |
| 219 | -OMe | 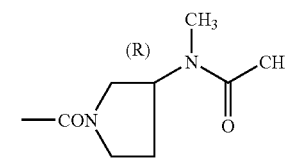 | 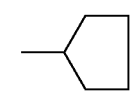 | — | m.p. = 190° C.<br>MH⁺ = 561<br>t = 9.8 |
| 220 | -OMe | 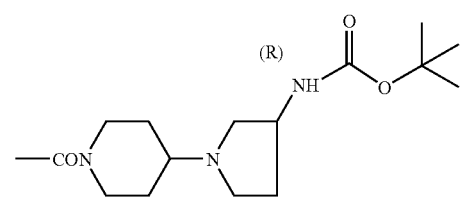 | | — | m.p. = 172° C.<br>MH⁺ = 674<br>t = 7.38 |

TABLE 7-continued

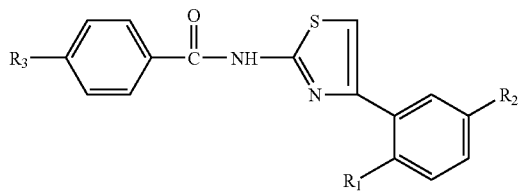

(Ia)

| Compound No. | R₁ | R₂ | R₃ | Salt | Characterization |
|---|---|---|---|---|---|
| 221 | -OMe | -nHex | (R) -CON-pyrrolidine-N(CH₃)C(O)CH₃ | — | m.p. = 124° C.<br>MH⁺ = 563<br>t = 9.96 |
| 222 | -OEt | cyclohexyl | (R) -CON-piperidine-N-pyrrolidine-NHC(O)OC(CH₃)₃ | — | m.p. = 176° C.<br>MH⁺ = 702<br>t = 7.98 |
| 223 | -OMe | cyclopentyl | (R) -CON-piperidine-N-pyrrolidine-NH₂ | — | m.p. = 189° C.<br>MH⁺ = 574<br>t = 5.16 |
| 224 | -OEt | cyclohexyl | (R) -CON-piperidine-N-pyrrolidine-NH₂ | — | m.p. = 161° C.<br>MH⁺ = 602<br>t = 6.39 |
| 225 | -OMe | cyclohexyl | (R) -CON-piperidine-N-pyrrolidine-NHC(O)OCH₂CH₃ | — | m.p. = 144° C.<br>MH⁺ = 660<br>t = 7.37 |
| 226 | -OEt | cyclohexyl | (R) -CON-piperidine-N-pyrrolidine-NHC(O)OCH₂CH₃ | — | m.p. = 136° C.<br>MH⁺ = 674<br>t = 7.59 |
| 227 | -OEt | cyclohexyl | (R) -CON-piperidine-N-pyrrolidine-NHC(O)CH₂CH₂CH₃ | — | m.p. = 131° C.<br>MH⁺ = 672<br>t = 7.52 |

TABLE 7-continued
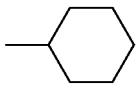
| Compound No. | R₁ | R₂ | R₃ | Salt | Characterization |
|---|---|---|---|---|---|
| 228 | -OEt | 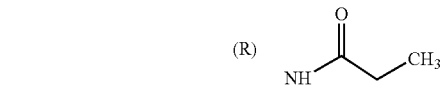 | 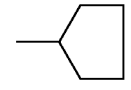 | — | m.p. = 152° C.<br>MH⁺ = 658<br>t = 7.47 |
| 229 | -OMe | 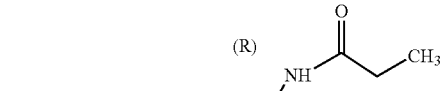 | 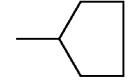 | — | m.p. = 163° C.<br>MH⁺ = 630<br>t = 7.16 |
| 230 | -OMe | 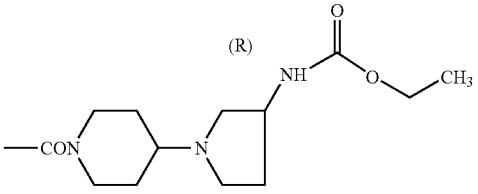 | 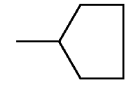 | — | m.p. = 136° C.<br>MH⁺ = 646<br>t = 7.09 |
| 231 | -OMe | 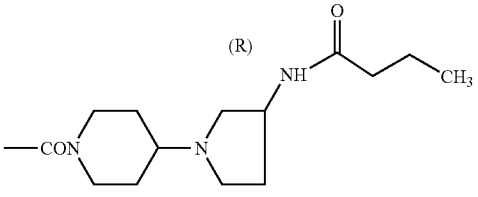 | 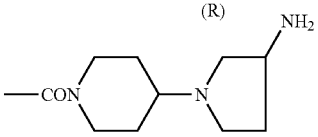 | — | m.p. = 182° C.<br>MH⁺ = 643<br>t = 7.29 |
| 232 | -OEt | -nBu | 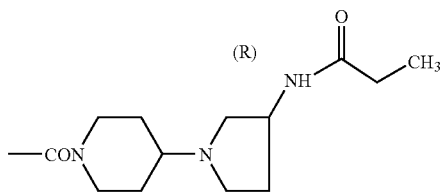 | — | m.p. = 138° C.<br>MH⁺ = 576<br>t = 6.06 |
| 233 | -OEt | -nBu |  | — | m.p. = 126° C.<br>MH⁺ = 632<br>t = 7.12 |

TABLE 7-continued
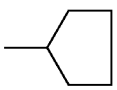
(Ia)
| Compound No. | R₁ | R₂ | R₃ | Salt | Characterization |
|---|---|---|---|---|---|
| 234 | -OEt | 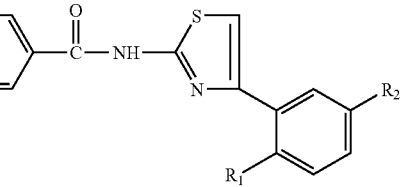 | 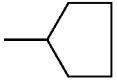 | — | m.p. MH⁺ = 644<br>t = 7.33 |
| 235 | -OEt | 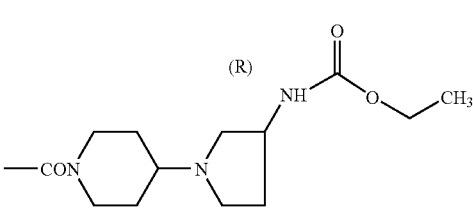 | 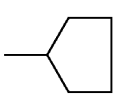 | — | m.p. MH⁺ = 660<br>t = 7.51 |
| 236 | -OEt | 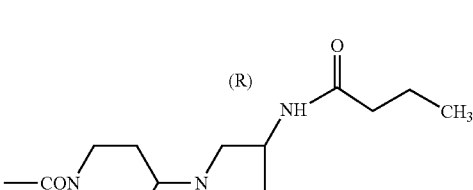 | 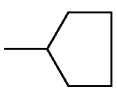 | — | m.p. = 105° C.<br>MH⁺ = 658<br>t = 7.27 |
| 237 | -OEt | 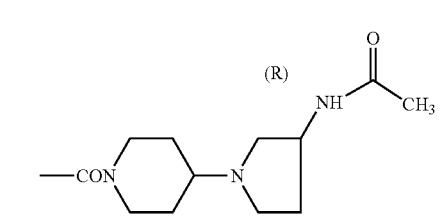 | 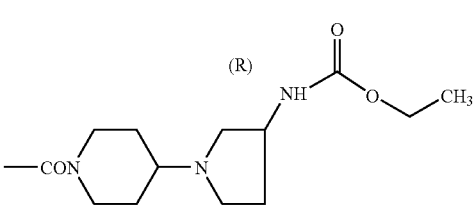 | — | m.p. = 121° C.<br>MH⁺ = 630<br>t = 7.04 |
| 238 | -OEt | -nBu | 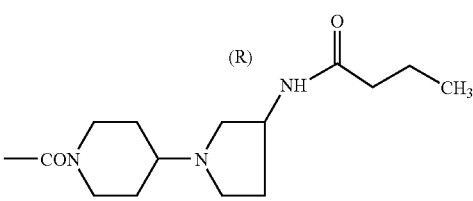 | — | m.p. = 102° C.<br>MH⁺ = 648<br>t = 7.48 |
| 239 | -OEt | -nBu |  | — | m.p. = 129° C.<br>MH⁺ = 646<br>t = 7.42 |

TABLE 7-continued

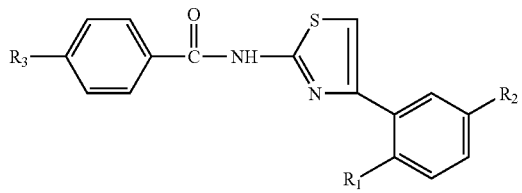

(Ia)

| Compound No. | R₁ | R₂ | R₃ | Salt | Characterization |
|---|---|---|---|---|---|
| 240 | -OMe | -nBu | (R) piperidine-pyrrolidine with NH-cyclopropanecarboxamide | — | m.p. = 124° C. MH⁺ = 630 t = 7.59 |
| 241 | -OMe | -nBu | (R) piperidine-pyrrolidine with NH-isobutyramide | — | m.p. = 135° C. MH⁺ = 632 t = 7.62 |
| 242 (4.1.2.) | -OMe | -OnPr | 4-oxopiperidine | — | m.p. = 196° C. |
| 243 (4.1.6.) | -OMe | cyclohexyl | 4-oxopiperidine | — | m.p. = 186° C. |
| 244 (4.1.7.) | -OEt | cyclohexyl | 4-oxopiperidine | — | m.p. = 236° C. |
| 245 | -OMe | cyclohexyl | (R) piperidine-pyrrolidine with NH-isobutyramide | — | m.p. = 154° C. |
| 246 | -OMe | cyclohexyl | (R) piperidine-pyrrolidine with NH-cyclopropanecarboxamide | — | m.p. = 158° C. |
| 247 | -OEt | -nBu | (R) piperidine-pyrrolidine with NH-isobutyramide | — | m.p. = 116° C. |

TABLE 7-continued
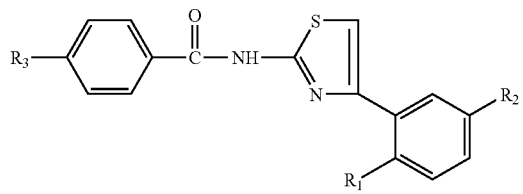
(Ia)
| Compound No. | R₁ | R₂ | R₃ | Salt | Characterization |
|---|---|---|---|---|---|
| 248 | -OEt | -nBu | 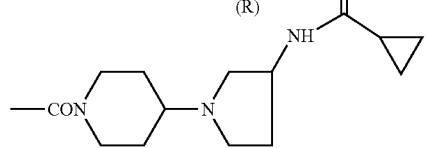 | — | m.p. = 118° C. |
| 249 | -OEt | 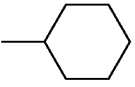 | 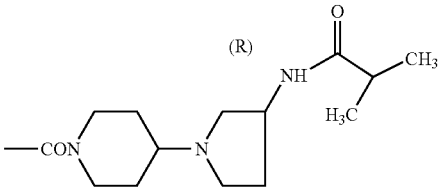 | — | m.p. = 135° C. |
| 250 | -OEt | 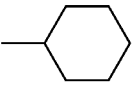 | 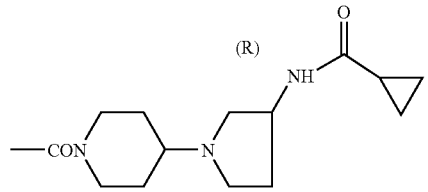 | — | m.p. = 141° C. |
| 251 | -OMe | -nBu | 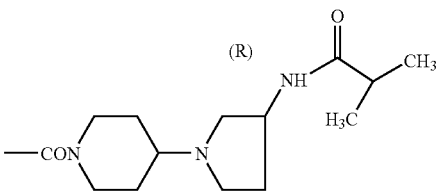 | — | m.p. = 119° C. |
| 252 | -OMe | -nBu | 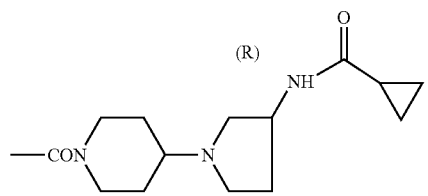 | — | m.p. = 109° C. |
| 253 | -OMe | -nBu | 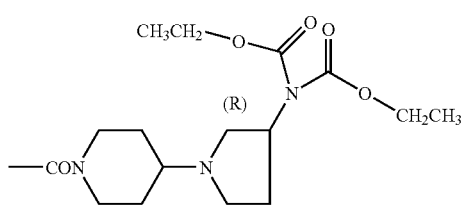 | HCl | m.p. = 148° C. |

TABLE 7-continued (Ia)

| Compound No. | R₁ | R₂ | R₃ | Salt | Characterization |
|---|---|---|---|---|---|
| 254 | -OMe | -nBu | (R) piperidine-pyrrolidine with N(CH₃)COCH₃ | — | m.p. = 118° C. |
| 255 | -OMe | -nBu | (S) piperidine-pyrrolidine with NH-CO-O-ethyl | HCl | m.p. = 176° C. |

NMR spectrum: Compound 1: 0.98 ppm:t:3H, 1.24 ppm:t:6H, 1.72 ppm:sext:2H, 3.1-3.3 ppm:m:4H, 3.4-3.6 ppm:m:2H, 3.8-4.0 ppm:m:5H, 4.50 ppm:t:2H, 6.87 ppm:dd:1H; 7.04 ppm:d:1H; 7.16 ppm:d:2H, 7.7-7.8 ppm:m:2H, 8.16 ppm:d:2H, 10.6 ppm:bs:1H; 12.5 ppm:bs:1H.

NMR spectrum: Compound 33: 1.00 ppm:t:3H, 1.26 ppm:t:6H, 1.74 ppm:sext:2H, 2.9-3.5 ppm:m:8H, 3.8-4.0 ppm:m:5H, 6.88 ppm:dd:1H; 7.04 ppm:d:1H; 7.5 ppm:d:2H, 7.7-7.8 ppm:m:2H, 8.14 ppm:d:2H.

NMR spectrum: Compound 67: 0.80 ppm:t:3H, 0.95-1.95 ppm:m:12H, 2.45 ppm:t:2H, 2.55-4.4 ppm:m:13H, 6.95 ppm:d:1H; 7.05 ppm:dd:1H; 7.45 ppm:d:2H, 7.65 ppm:s:1H; 7.90 ppm:s:1H; 8.1 ppm:d:2H.

NMR spectrum: Compound 69: 1.1 ppm:t:3H, 1.15-1.90 ppm:m:4H, 2.20-4.50 ppm:m:17H, 6.95 ppm:d:1H; 7.05 ppm:dd:1H; 7.45 ppm:d:2H, 7.60 ppm:s:1H; 7.95 ppm:s:1H; 8.1 ppm:d:2H, 12.65 ppm:bs:1H.

NMR spectrum: Compound 70: 0.85-1.95 ppm:m:11H, 2.30-4.4 ppm:m:15H, 6.95 ppm:d:1H; 7.05 ppm:dd:1H; 7.40 ppm:d:2H, 7.60 ppm:s:1H; 7.90 ppm:s:1H; 8.1 ppm:d:2H.

The compounds according to the invention underwent pharmacological tests to determine their modulatory effect on the activity of the chemokine receptors.

Chemokines are low molecular weight proteins belonging to the family of pro-inflammatory cytokines and are involved in the chemotaxis of leukocytes and endothelial cells. Chemokines control many biological processes and are associated with inflammatory disorders appearing during conditions of stress, during injury or infection; modulation of the effects of chemokines makes it possible to prevent or treat pathologies such as asthma, arthritis, allergies, autoimmune diseases, atherosclerosis or angiogenesis (C. D. Paavola et al., J. Biol. Chem., 1998, 273, (50), 33157-33165).

Among the chemokines that may be distinguished are hMCP-1 (human monocyte chemotactic protein), which belongs to the group of CC chemokines and whose actions are mediated by the CCR2b receptor.

The inhibitory activity of the compounds according to the invention on cells expressing the human CCR2b receptor was measured. The concentration of natural agonist hMCP-1 that inhibits 50% ($IC_{50}$) of the activity of the CCR2b receptor is 0.57 nM. The compounds according to the invention have an $IC_{50}$ value generally of less than 0.1 µM.

For example, compound 12 has an $IC_{50}$ value of 0.081 µM; compound 244 has an $IC_{50}$ value of 0.088 µM; compound 203 has an $IC_{50}$ value of 0.093 µM.

The inhibition of chemotaxis was also measured on human THP-1 monocytes (sold by DSMZ-Germany) using a technique adapted from that described by A. Albini et al., Cancer Res., 1987, 47, 3239-3245. Under these conditions, hMCP-1 has an $IC_{50}$ value of 6 nM. The compounds according to the invention have an $IC_{50}$ value generally of less than 1 µM.

The inhibition of chemotaxis by the compounds according to the invention is a sign of their antagonist activity on the chemokine receptors and in particular CCR2b.

It is thus seen that the compounds according to the invention are antagonists of the effect of chemokines, in particular of hMCP-1.

The inhibitory activity of the compounds according to the invention on PBMCs (peripheral blood mononuclear cells) infected with the HIV-1 Bal virus was also measured, according to a technique adapted from that described by V. Dolle et al., J. Med. Chem., 2000, 43, 3949, 3962. According to this technique, the PMBCs are infected with HIV-1 Bal and the test compounds are then added to the culture medium for 5 days. At the end of this exposure, the content of reverse transcriptase, which is correlated with the level of viral replication in the cells, is measured in the supernatant.

Under these conditions, AZT, a reference molecule which inhibits viral replication, has an $IC_{50}$ value of less than 0.1 µM. The compounds according to the invention also have $IC_{50}$ values generally of less than 0.1 µM. For example, compound 104 showed an $IC_{50}$ value of 0.063 µM.

The compounds according to the invention may thus be used for the preparation of medicinal products, in particular medicinal products that are antagonists of the effect of chemokines.

Thus, according to another of its aspects, a subject of the present invention is medicinal products comprising a compound of formula (I), or an addition salt thereof with a pharmaceutically acceptable acid, or alternatively a hydrate or a solvate.

These medicinal products find their therapeutic use especially in the prevention and treatment of various pathologies such as:

acute and chronic immunoinflammatory diseases and syndromes, for instance atherosclerosis, restenosis, chronic pulmonary diseases, in particular COPD (chronic obstructive pulmonary disease); respiratory distress syndrome; bronchial hyperactivity; colitis; silicosis; fibrotic pathologies, pulmonary fibrosis and cystic fibrosis; viral or bacterial infections, AIDS, meningitis, malaria, leprosy, tuberculosis, herpes and cytomegalovirus infections; septic shock, septicaemia and endotoxic shock; graft rejection; bone pathologies such as osteoporosis and osteoarthritis; conjunctivitis; atypic or contact dermatitis; eczema, glomerulonephritis; pancreatitis; ulcerative colitis, autoimmune diseases, for instance rheumatoid arthritis, multiple sclerosis, amyotrophic lateral sclerosis, Crohn's disease, lupus erythematosus, scleroderma and psoriasis; Parkinson's disease; Alzheimer's disease; diabetes; cachexia; obesity;

the treatment of pain, in particular neuropathic and inflammatory pain;

allergic diseases, for instance allergic respiratory diseases, asthma, rhinitis, pulmonary hypersensitivity and delayed hypersensitivity;

diseases and disorders in which angiogenic processes are involved, for instance cancers (intratumoral angiogenesis) and retinal diseases (age-related macular degeneration: ARMD);

cardiac pathologies: haemodynamic shock; cardiac ischaemia; post-ischaemic reinfusion attack; myocardial infarction, coronary thrombosis, cardiac insufficiency and angina pectoris.

According to another of its aspects, the present invention relates to pharmaceutical compositions comprising, as active principle, a compound according to the invention. These pharmaceutical compositions contain an effective dose of at least one compound according to the invention, or a pharmaceutically acceptable salt, a hydrate or solvate of the said compound, and also at least one pharmaceutically acceptable excipient.

The said excipients are chosen according to the pharmaceutical form and the desired mode of administration, from the usual excipients known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or the possible salt, solvate or hydrate thereof, may be administered in unit administration form, as a mixture with standard pharmaceutical excipients, to man and animals for the prophylaxis or treatment of the above disorders or diseases.

The appropriate unit administration forms comprise oral-route forms such as tablets, soft or hard gel capsules, powders, granules and oral solutions or suspensions, sublingual, buccal, intratracheal, intraoccular and intranasal administration forms, forms for inhalation, topical, transdermal, subcutaneous, intramuscular or intravenous administration forms, rectal administration forms and implants. For topical application, the compounds according to the invention may be used in creams, gels, ointments or lotions.

By way of example, a unit administration form of a compound according to the invention in the form of a tablet may comprise the following components:

| | |
|---|---|
| Compound according to the invention | 50.0 mg |
| Mannitol | 223.75 mg |
| Sodium croscaramellose | 6.0 mg |
| Maize starch | 15.0 mg |
| Hydroxypropylmethylcellulose | 2.25 mg |
| Magnesium stearate | 3.0 mg |

Via the oral route, the dose of active principle administered per day may be up to 0.1 to 1000 mg/kg, in one or more dosage intakes.

There may be particular cases in which higher or lower doses are suitable; such doses do not depart from the context of the invention. In usual practice, the dosage that is appropriate for each patient is determined by a doctor according to the mode of administration, the weight and the response of the said patient.

According to another of its aspects, the present invention also relates to a method for treating the pathologies indicated above, which comprises the administration, to a patient, of an effective dose of a compound according to the invention, or a pharmaceutically acceptable salt, hydrate or solvate thereof.

What is claimed is:

1. A compound of the formula (IIe),

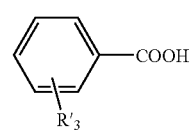

(IIe)

or a $(C_1-C_4)$ aliphatic ester or benzyl ester of a compound of formula (IIe), where the phenyl portion of the benzyl portion of the benzyl ester is unsubstituted, or substituted with a methoxy group, wherein:

R'$_3$ represents —CO-G-A,
A represents a group NR$_5$R$_6$;
G represents a group

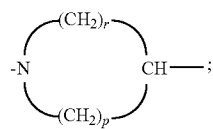

R$_5$ represents, a hydrogen atom and R$_6$ represents a tetrahydropyranyl, group;
r represents 2;
p represents 2;
or R'$_3$ represents a precursor of R'$_3$ as defined above in which any amine or hydroxyl functions on R'$_3$ that may be present are protected.

2. A benzoic acid compound of the formula

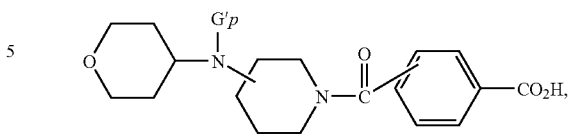

or a (C$_1$-C$_4$) alkyl ester or benzyl ester of such benzoic acid compound, where the phenyl portion of the benzyl portion of the benzyl ester is unsubstituted, or substituted with a methoxy group,
wherein: G'p represents hydrogen or a protecting group for nitrogen selected from the group consisting of Boc, Fmoc, benzyloxycarbonyl, benzyl and (C$_1$-C$_4$)alkanoyl.

* * * * *

UNITED STATES PATENT AND TRADEMARK OFFICE
CERTIFICATE OF CORRECTION

PATENT NO. : 7,777,041 B2
APPLICATION NO. : 12/360568
DATED : August 10, 2010
INVENTOR(S) : Pierre Carayon et al.

It is certified that error appears in the above-identified patent and that said Letters Patent is hereby corrected as shown below:

In column 5, line 46, delete "(CH$_2$)," and insert -- (CH$_2$)$_s$ --, therefor.

In column 14, line 5, below "a2):" insert -- SCHEME 5a --.

In column 24, line 26-36, delete " 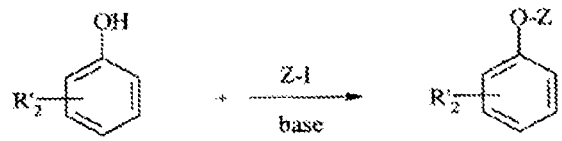 " and insert -- 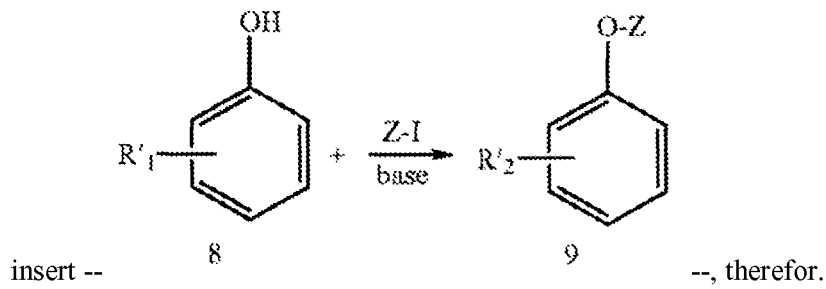 --, therefor.

Signed and Sealed this
Twenty-second Day of May, 2012

David J. Kappos
*Director of the United States Patent and Trademark Office*

CERTIFICATE OF CORRECTION (continued)
U.S. Pat. No. 7,777,041 B2

In column 24, line 41-51, delete " 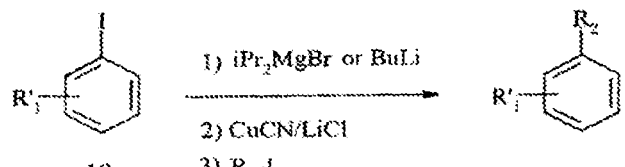 " and insert -- 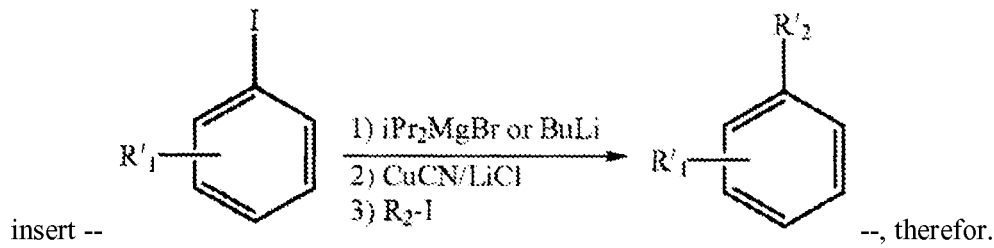 --, therefor.

In column 28, line 16, delete "R$_1$," and insert -- R$_1$ --, therefor.

In column 32, line 41, delete "purifed" and insert -- purified --, therefor.

In column 35, line 45-50, delete " 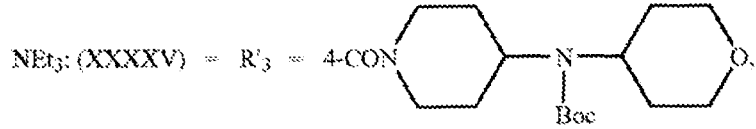 "

and insert --  --, therefor.

In column 36, line 60-66, delete " 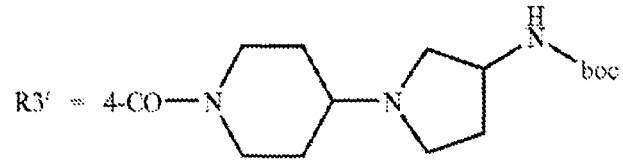 "

and insert -- 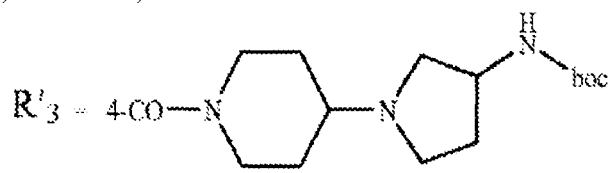 --, therefor.

In column 45, line 50-60, delete " 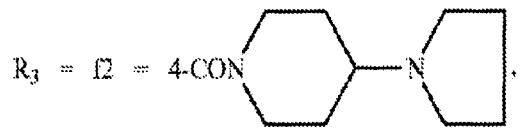 "
and insert -- 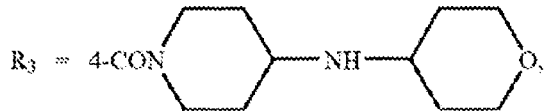 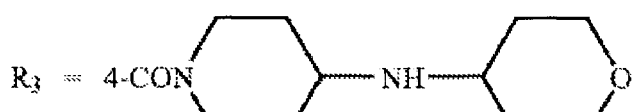 --, therefor.
In column 49, line 43-54, delete " 
and insert -- --, therefor.

CERTIFICATE OF CORRECTION (continued)
U.S. Pat. No. 7,777,041 B2

In column 54, line 9-14, delete "2HCl: $R_1$ = 2-OMe; $R_2$ = 5-OnPr; $R_3$ = $a_1$ = 4-O—($CH_2)_2$—N, (I)" and insert -- 2HCl: $R_1$ = 2-OMe; $R_2$ = 5-OnPr; $R_3$ = $a_1$ = 4-O—($CH_2)_2$—N (I) --, therefor.

In column 59-60, line 2, compound 15, delete "$MH^{+=}$ 511.4" and insert -- $MH^+$ = 511.4 --, therefor.

In column 65-66, line 1, compound 44, delete "-OMe" and insert -- -OEt --, therefor.

In column 65-66, line 1, compound 44, above "$MH^+$= 468.4" insert -- F= 180° C --.

In column 65-66, line 1, compound 53, delete "—($CH_2)_2NEt_2$" and insert -- —O($CH_2)_2NEt_2$ --, therefor.

In column 67-68, line 1, compound 55, delete "—$OCHEt_2$" and insert -- —$CHEt_2$ --, therefor.

In column 67-68, line 1, compound 55, delete "—($CH_2)_2NEt_2$" and insert -- —O($CH_2)_2NEt_2$ --, therefor.

In column 67-68, line 1, compound 63, delete "-OMe" and insert -- OnPr --, therefor.

In column 67-68, line 1, compound 64, delete "-OnPr" and insert -- OMe --, therefor.

In column 67-68, line 1-3, compound 65, delete " m.p. = 199° C.$MH^+$ = 577.5 t = 6.83 " and insert -- m.p. = 199°C. $MH^+$ = 577.5 t = 6.83 --, therefor.

CERTIFICATE OF CORRECTION (continued)
U.S. Pat. No. 7,777,041 B2

In column 67-68, line 1, compound 67, delete "-NMR" and insert -- —  --, therefor.

In column 85-86, line 1, compound 158, delete " 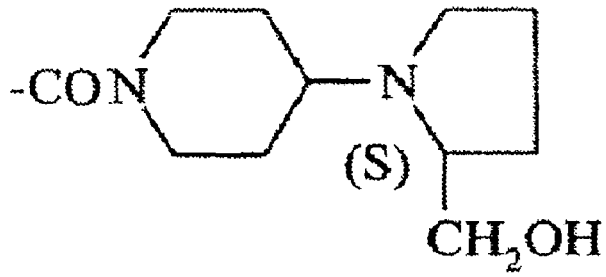 insert -- 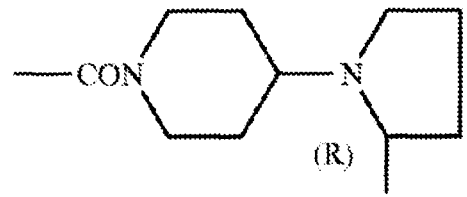 and --, therefor.

In column 91-92, line 1, compound 186, delete " 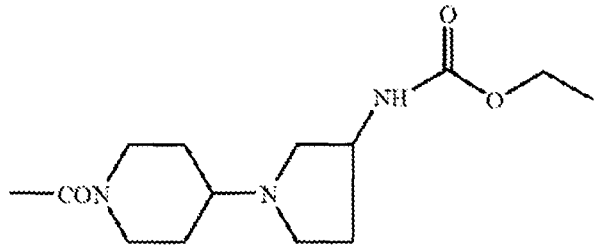 and insert -- 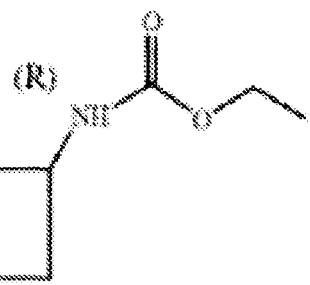 --, therefor.

In column 91-92, line 1, compound 187, delete " 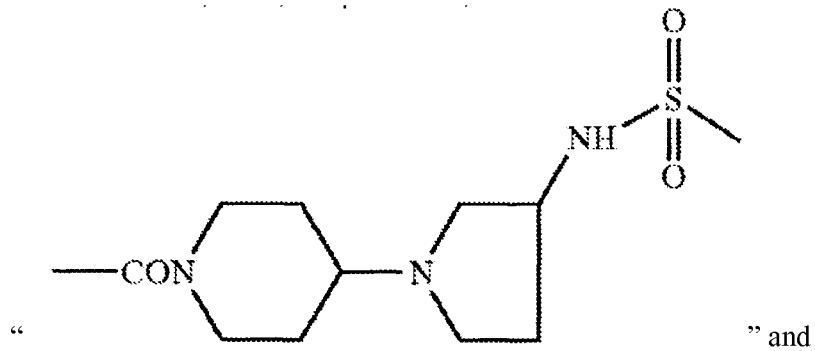 " and insert -- 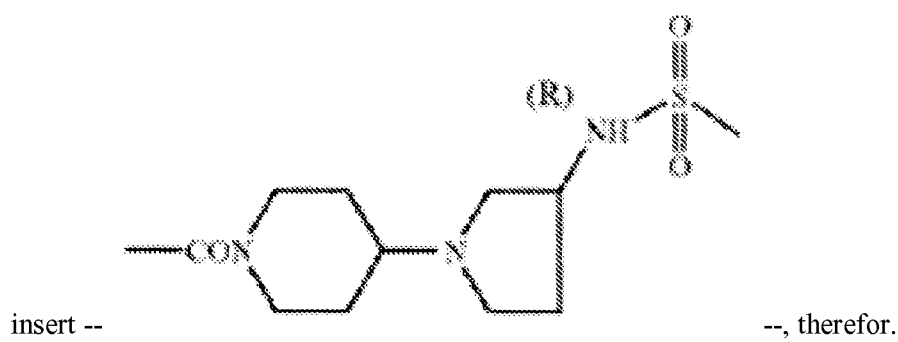 --, therefor.
In column 91-92, line 1, compound 188, delete " 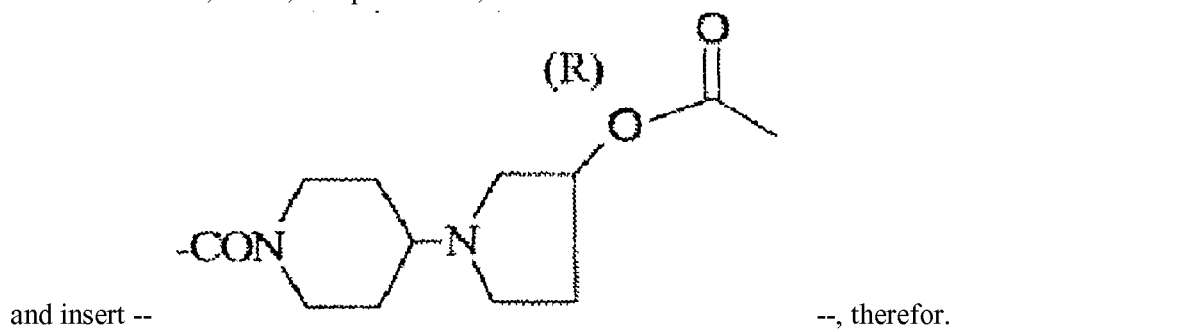 " and insert -- 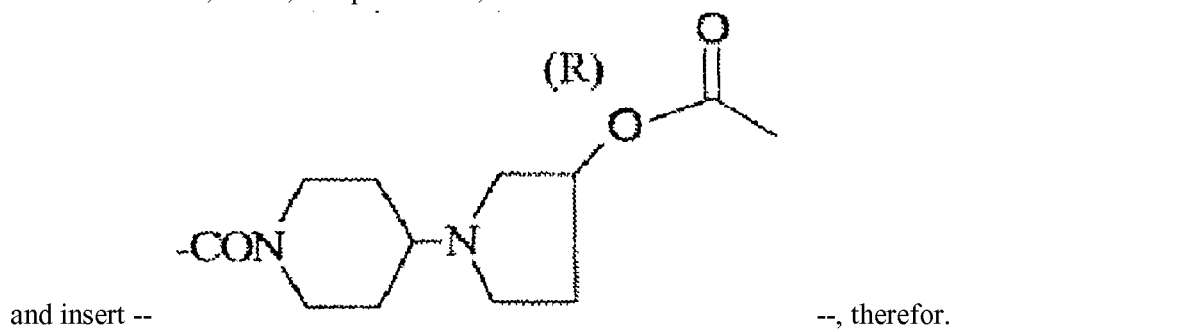 --, therefor.
In column 114, line 18, delete "intraoccular" and insert -- intraocular --, therefor.
In column 114, line 32, delete "croscaramellose" and insert -- croscarmellose --, therefor.
In column 115, line 12, in claim 1, delete "represents," and insert -- represents --, therefor.

In column 115, line 12-13, in claim 1, delete "tetrahydropyranyl," and insert -- tetrahydropyranyl --, therefor.